United States Patent
Irminger-Finger et al.

(10) Patent No.: US 9,599,624 B2
(45) Date of Patent: Mar. 21, 2017

(54) BARD1 ISOFORMS IN LUNG AND COLORECTAL CANCER AND USE THEREOF

(75) Inventors: Irmgard Irminger-Finger, Geneva (CH); Yong-Qiang Zhang, Beijing (CN)

(73) Assignees: HOPITAUX UNIVERSITAIRES DE GENEVE, Geneva (CH); UNIVERSITE DE GENEVE, Geneva (CH)

( * ) Notice: Subject to any disclaimer, the term of this patent is extended or adjusted under 35 U.S.C. 154(b) by 0 days.

(21) Appl. No.: 13/817,013

(22) PCT Filed: Aug. 17, 2011

(86) PCT No.: PCT/IB2011/053635
§ 371 (c)(1),
(2), (4) Date: Feb. 14, 2013

(87) PCT Pub. No.: WO2012/023112
PCT Pub. Date: Feb. 23, 2012

(65) Prior Publication Data
US 2013/0149711 A1    Jun. 13, 2013

Related U.S. Application Data

(60) Provisional application No. 61/374,370, filed on Aug. 17, 2010.

(30) Foreign Application Priority Data

Apr. 6, 2011   (CH) .......................................... 621/11

(51) Int. Cl.
*G01N 33/68* (2006.01)
*C12Q 1/68* (2006.01)
*C07K 16/40* (2006.01)
*C12N 9/00* (2006.01)
*G01N 33/574* (2006.01)

(52) U.S. Cl.
CPC ......... *G01N 33/6884* (2013.01); *C07K 16/40* (2013.01); *C12N 9/93* (2013.01); *C12Q 1/6886* (2013.01); *C12Y 603/02* (2013.01); *G01N 33/57419* (2013.01); *G01N 33/57423* (2013.01); *G01N 33/6893* (2013.01); *G01N 2333/4703* (2013.01)

(58) Field of Classification Search
CPC ....... G01N 33/57419; G01N 33/57423; C12N 5/0693; C12N 15/1135; C12N 2330/10; C12Q 1/6886; C12Q 1/6827
See application file for complete search history.

(56) References Cited

U.S. PATENT DOCUMENTS

2004/0234959 A1*  11/2004  Gautier et al. .................... 435/6

FOREIGN PATENT DOCUMENTS

| WO | 98/12327 | 3/1998 |
|---|---|---|
| WO | 03/051920 | 6/2003 |
| WO | 2008/119802 | 10/2008 |

OTHER PUBLICATIONS

Yang et al (Chinese Journal of Obstetrics and Gynecology, 2008, 49:680-684; english translation pp. 1-17).*
Li et al (Cancer Research, 2007, 67:11876-11885).*
Irminger-Finger et al. (The Journal of Cell Biology, 1998, 143:1329-1339).*
Gautier et al. (Cancer Research, 2000, 60:6895-6900).*
Irminger-Finger, I., et al. "Identification of oncogenic BARD1 isoforms in lung cancer." Proceedings of the Annual Meeting of the American Association for Cancer Research. Apr. 22, 2009;50:208. Abstract #3335.
Bianco, A., et al. "Distinct BARD1 isoforms expressed in lung cancer potential targets for treatment." European Respiratory Society Annual Congress. Berlin, Germany. Oct. 7, 2008. Abstract #3006.
Zhang, Y.Q., et al. "BARD1: an independent predictor of survival in non-small cell lung cancer." Int J Cancer. Jul. 1, 2012;131(1):83-94. Epub Dec. 21, 2011.

* cited by examiner

*Primary Examiner* — Julie Wu
(74) *Attorney, Agent, or Firm* — Rothwell, Figg, Ernst & Manbeck, P.C.

(57) ABSTRACT

The present invention relates to new BARD1 isoforms specific to lung cancer and colorectal cancer, a method for detecting thereof and a method for treating and/or preventing lung cancer and colorectal cancer.

14 Claims, 34 Drawing Sheets

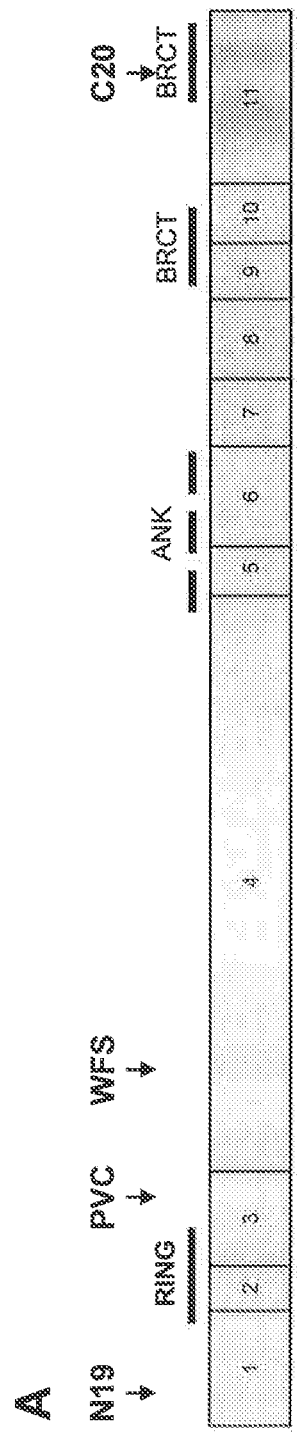

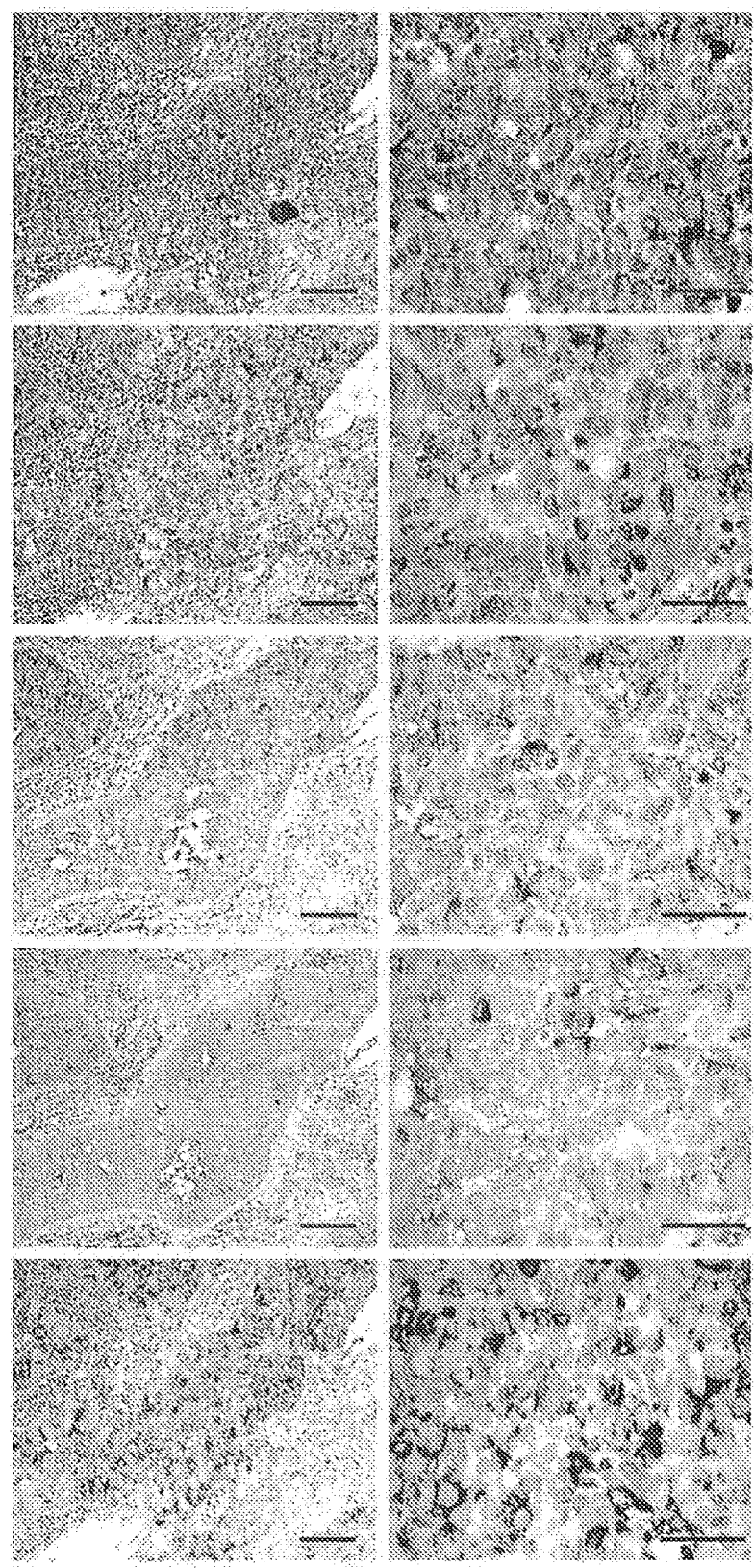

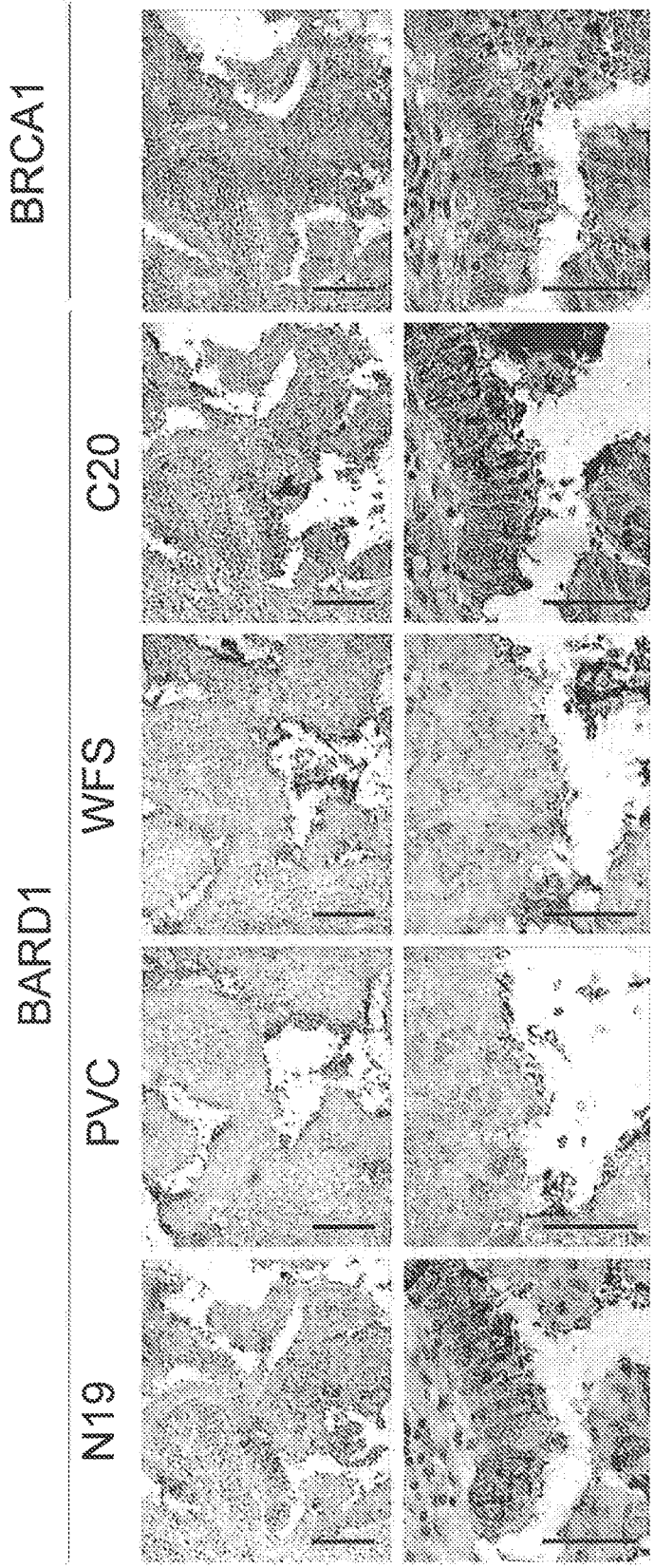

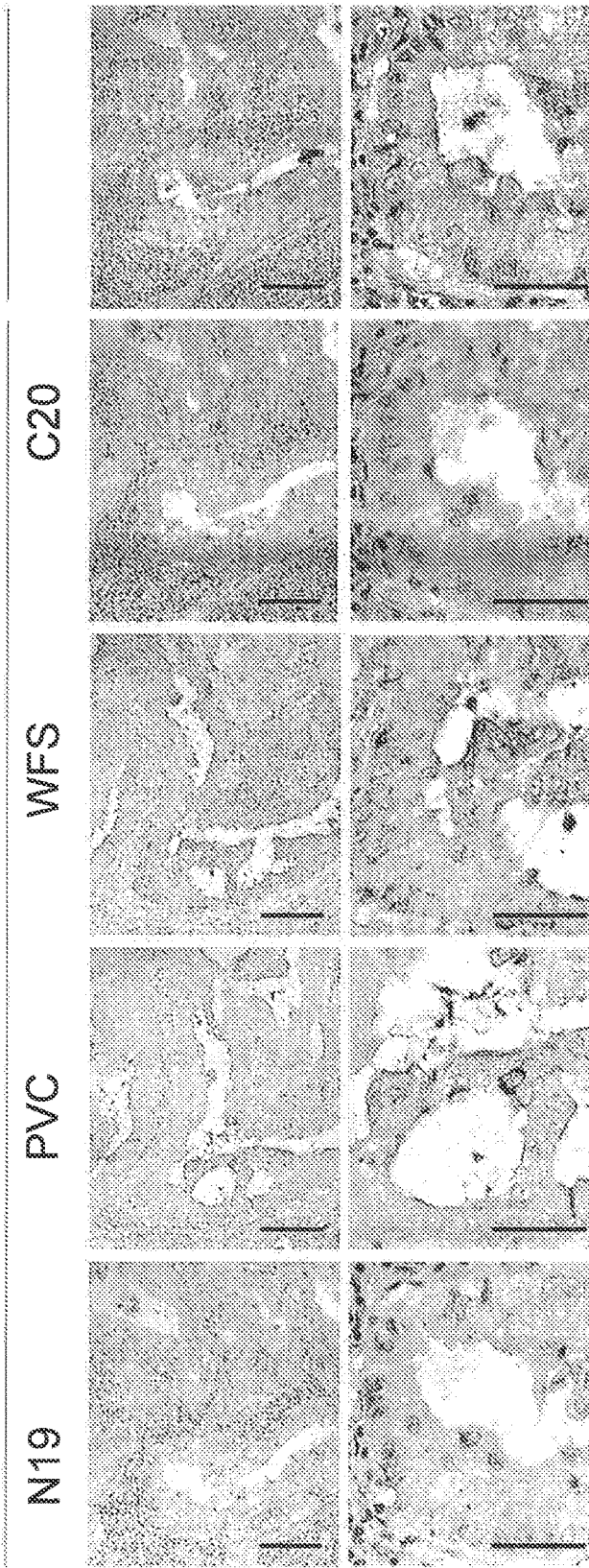

Figure 1E

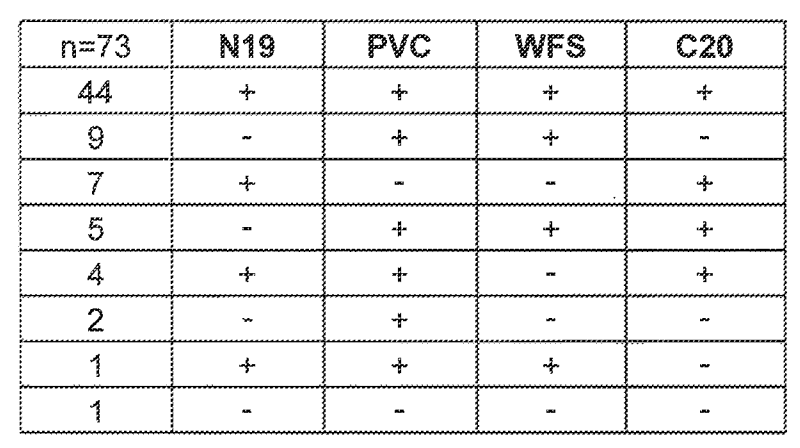

| n=73 | N19 | PVC | WFS | C20 |
|---|---|---|---|---|
| 44 | + | + | + | + |
| 9 | - | + | + | - |
| 7 | + | - | - | + |
| 5 | - | + | + | + |
| 4 | + | + | - | + |
| 2 | - | + | - | - |
| 1 | + | + | + | - |
| 1 | - | - | - | - |

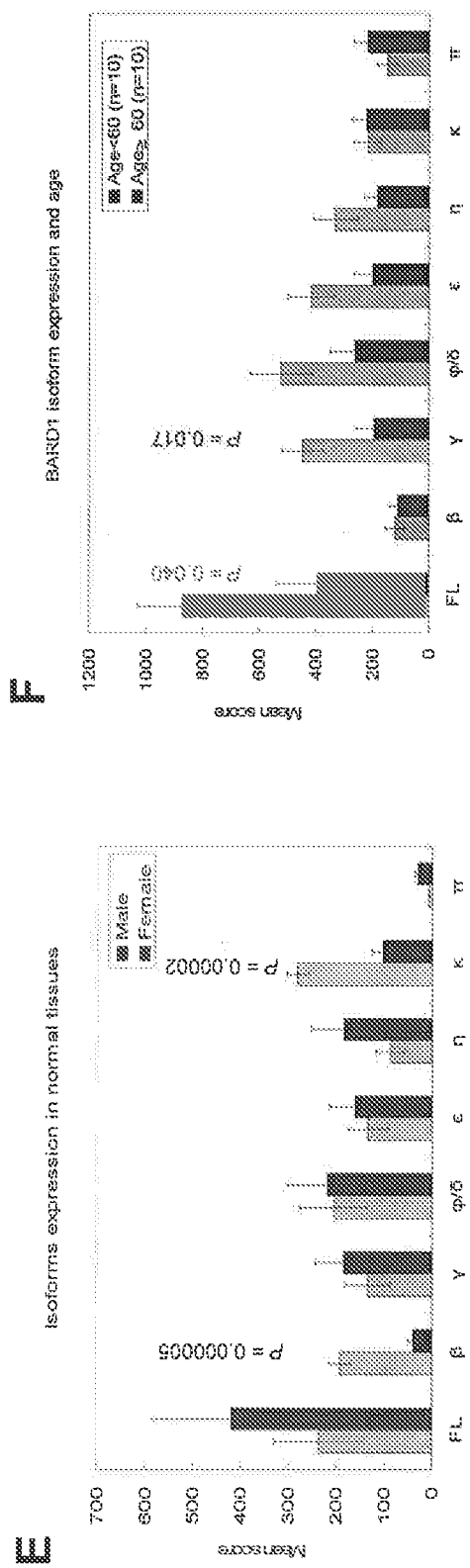

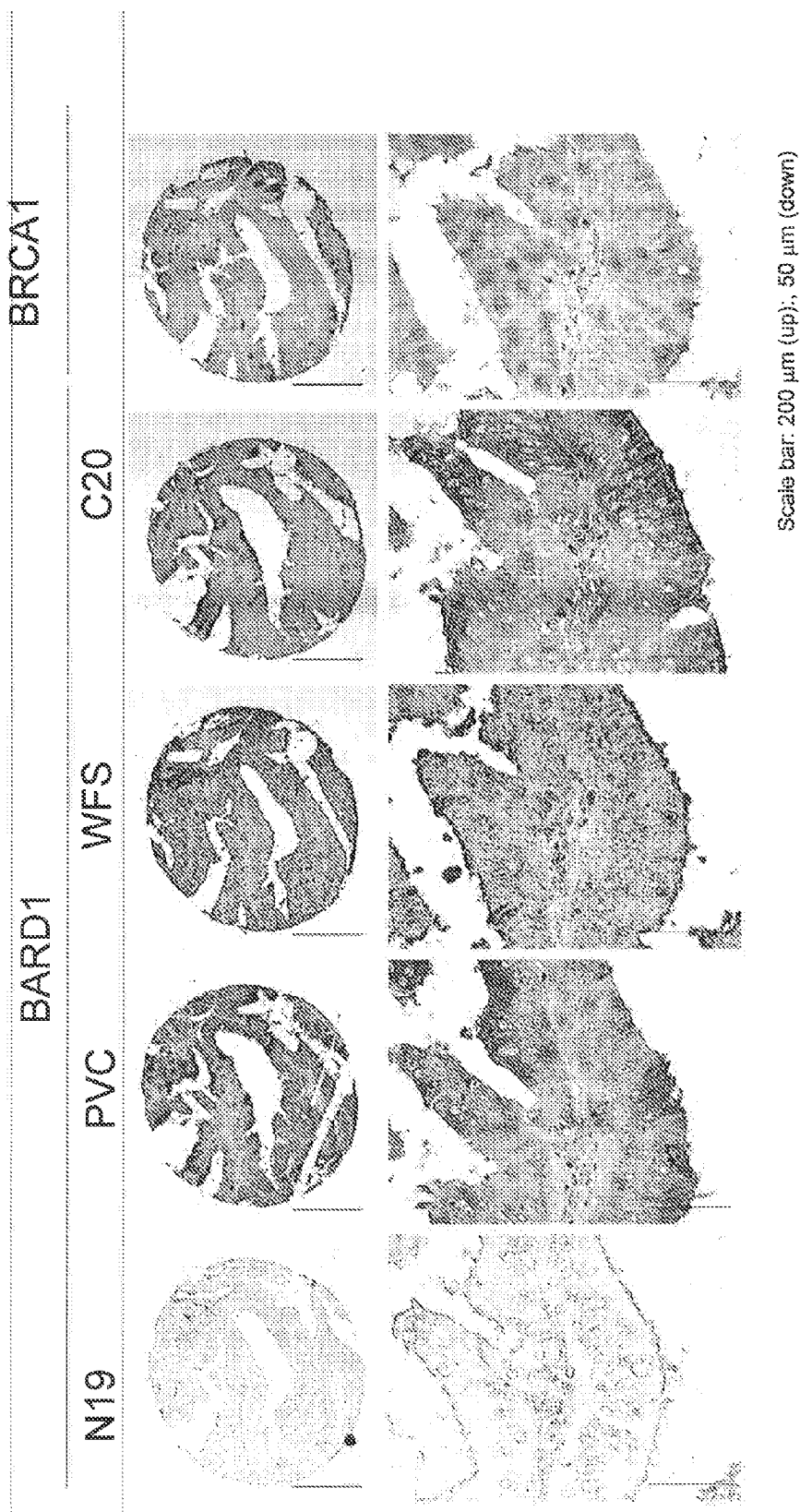

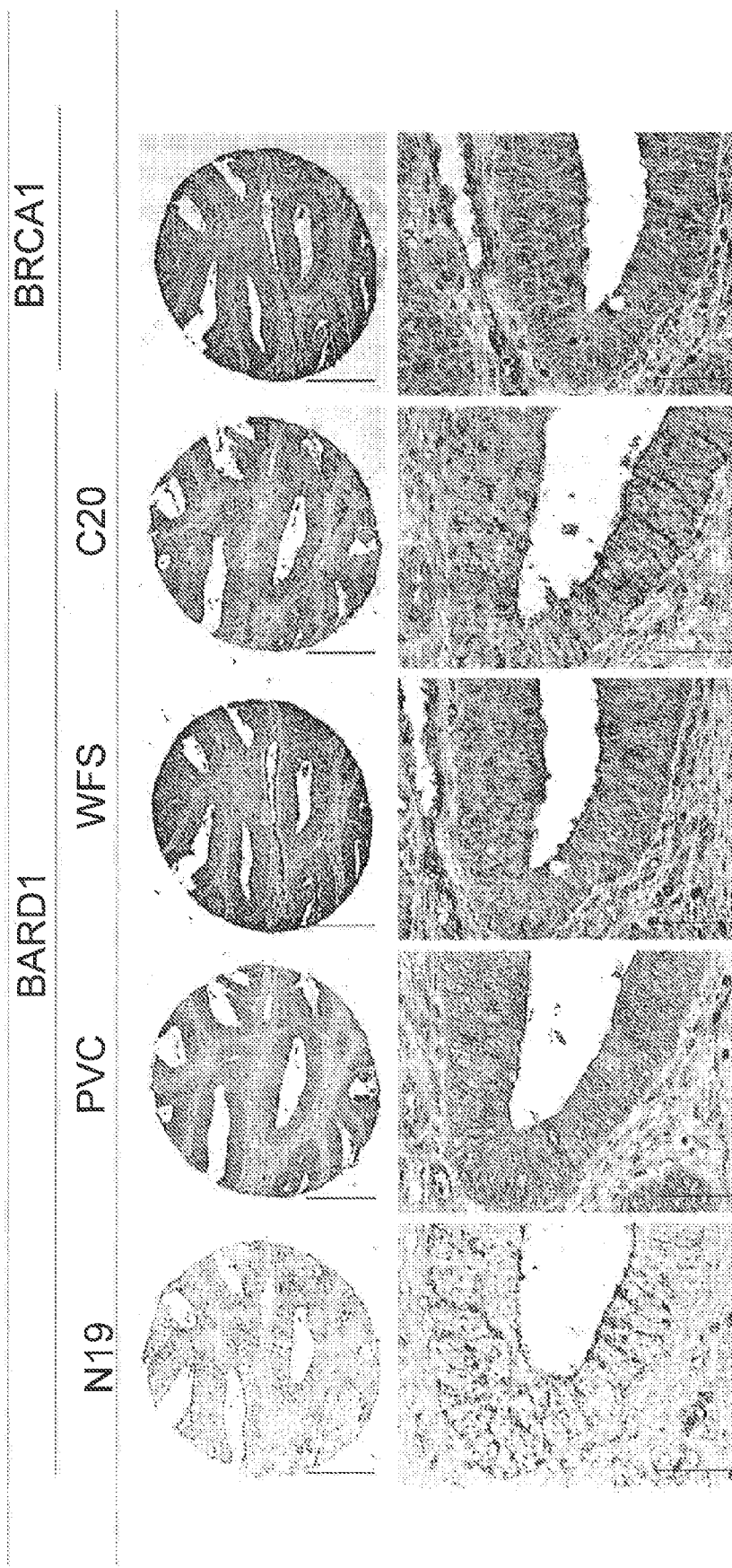

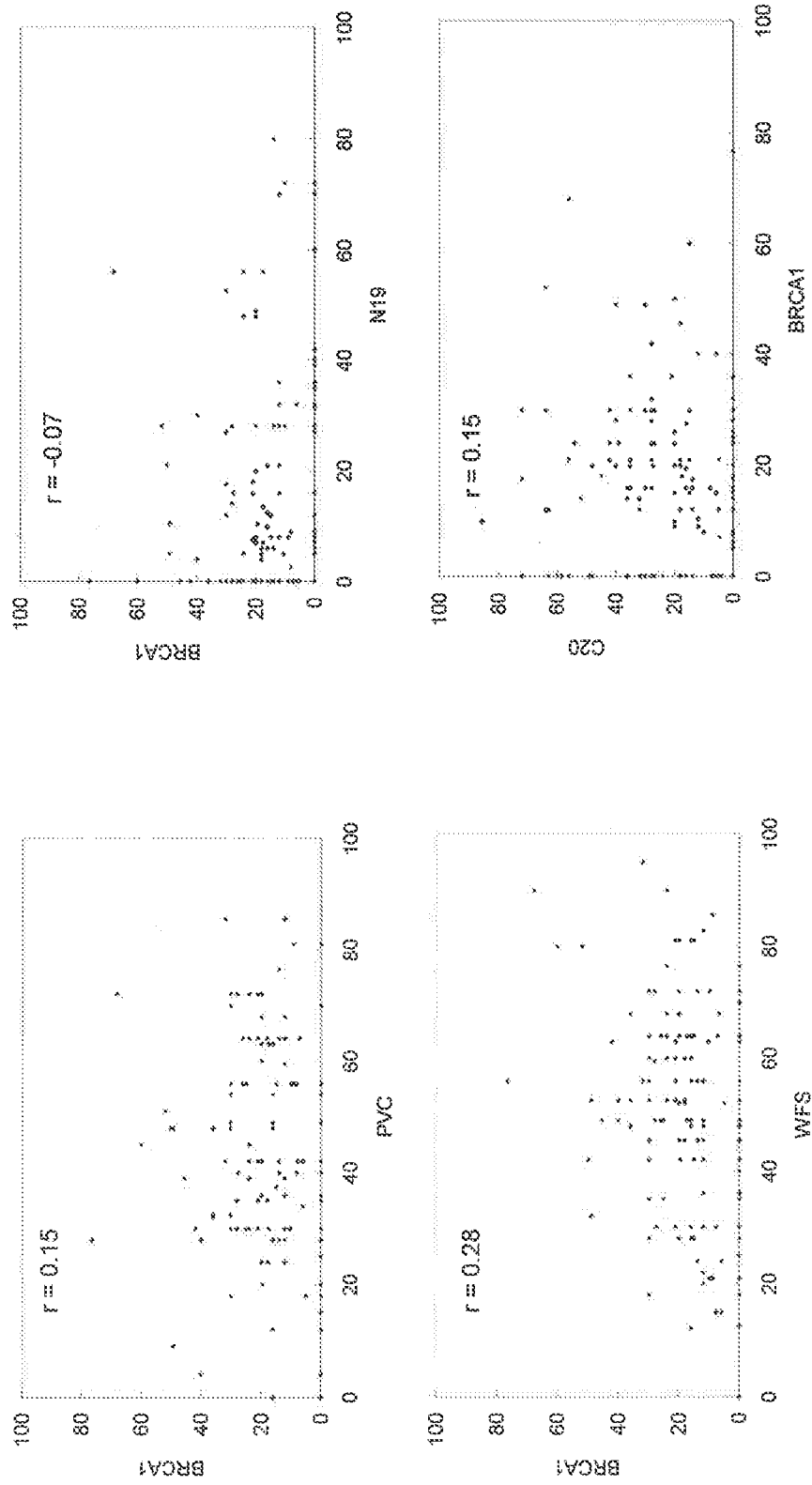

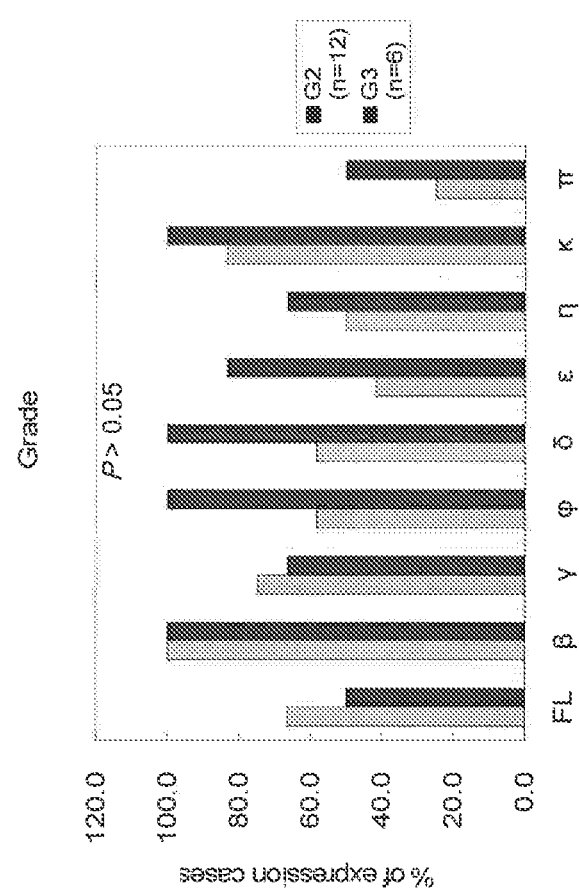

BARD1 ISOFORMS IN LUNG AND COLORECTAL CANCER AND USE THEREOF

The present application is §371 application of PCT/IB2011/053635, filed Aug. 17, 2011, which claims priority to Swiss Application No. 00621/11, filed Apr. 6, 2011, and U.S. Provisional Application No. 61/374,370, filed Aug. 17, 2010. The entire disclosure of each of the foregoing applications is incorporated by reference herein.

Incorporated herein by reference in its entirety is the Sequence Listing being concurrently submitted via EFS-Web as an ASCII text file named SequenceListing.txt, created Feb. 6, 2013, and having a size of 84,853 bytes.

FIELD OF THE INVENTION

The present invention relates to new BARD1 isoforms specific to lung cancer and colorectal cancer, a method for detecting thereof and a method for treating and/or preventing lung cancer and colorectal cancer.

BACKGROUND OF THE INVENTION

Lung cancer is the leading cause of cancer death worldwide. Treatment methods other than surgery are not very efficient and lead to resistance. Thus, insights into the etiology of lung cancer and its progression are urgently needed. Colorectal cancer is another leading cause of cancer-related death and the fourth most common cancer worldwide. The survival and prognosis of colorectal cancer patients depends on the stage of the tumor at the time of diagnosis. Early stages of colorectal cancer can be curable. Unfortunately, over 57% have regional or distant spread of the disease at the time of diagnosis. Despite significant investment and advances in the management of cancer, the five-year survival is only 15% for advanced stage colorectal cancer patients.

Recently, many groups have addressed the mechanisms that drive lung cancer by comparing protein, RNA, and microRNA in tumours with healthy tissue. Besides TP53, the most frequently deleted or mutated gene in lung cancer, components of the p53-ARF pathway are also consistently deleted, mutated, or epigenetically modified. As to the colorectal cancer, the challenges are to understand the molecular basis, and to determine factors that initiate the development, and drive the progression. The molecular events involved in colorectal cancer onset and metastatic progression have only been partially clarified. Recent studies have revealed the potential use of molecular and biochemical markers in colorectal cancer to predict outcome and response to chemotherapy, like MLH1, MSH2, β-Catenin, and p53.

Molecular profiles are emerging as predictive and prognostic parameters in non-small-cell lung cancer (NSCLC), including genes involved in DNA damage repair, such as ERCC1, RRM1, and BRCA1. The upregulated expression of the breast cancer predisposition gene, BRCA1 was proposed as prognostic and predictive marker for response to treatment in NSCLC. Concerning colorectal cancer, the studies of the BRCA1 are mainly limited in colorectal cancer risk and BRCA1 mutations. Several studies attempted to correlate BRCA1 mutations and colorectal cancer risk, but without any clear conclusions. Based on the current limited available evidence, BRCA mutation carriers should be regarded as at high risk for colorectal cancer. However the specific role of BRCA1 expression in colorectal cancer is unclear.

BRCA1 is expressed in many proliferating tissues and acts as a tumour suppressor in DNA repair pathways and cell cycle control. BRCA1 protein stability and function depend on its interaction with BARD1 (BRCA1 associated RING domain protein 1). The BRCA1-BARD1 heterodimer has E3 ubiquitin ligase activity, thus controlling the stability of key target proteins through ubiquitination. BARD1 is also involved in p53-dependent apoptosis, which is deficient in most lung cancers. BARD1 stabilizes p53 and promotes its phosphorylation, and expression of BARD1 is required for proper p53 functioning in signalling towards apoptosis. Thus, BARD1 plays a dual role in tumour suppression, as a binding partner of both BRCA1 and p53. Several studies have shown that BARD1 is upregulated during mitosis, transcriptionally by E2F and posttranslationally by phosphorylation, and importantly, that it is essential for mitosis. According to other studies, both BRCA1 and BARD1 were shown to interact with hMSH2, a gene commonly associated with hereditary nonpolyposis colorectal cancer (HNPCC) and mutations of hMSH2 appear to account for approximately 30-40% of HNPCC. Defects in the BRCA1-hMSH2 signalling process lead to increased susceptibility to tumorigenesis.

WO 98/12327 (Board of Regents, the University of Texas System) discloses several genes, identified in screening assays based upon binding to the breast cancer protein, BRCA1. One of these genes is termed BARD1, a RING protein that interacts with BRCA1 and is envisioned for use in various cancer-related diagnostic and therapeutic methods, particularly those connected with breast, ovarian and uterine cancer.

WO 2008/119802 (Université de Genève) discloses that in gynecological cancers, deletion-bearing isoforms of BARD1 are overexpressed and aberrantly localized to the cytoplasm, and their expression correlated with poor prognosis in breast and ovarian cancer. Structural analysis of these isoforms showed that they lacked the regions that interact with BRCA1 or induce apoptosis. These isoforms are specific to gynecological cancers and are termed as isoforms α, β, η, γ, ε, φ, δ and θ.

Due to the severity and incurability of lung and colorectal cancers, there is still a need to develop an effective detecting method which would allow the identification of these cancers and further allow development of effective methods and compositions for treatment or prevention thereof. The main problem is that to date, no efficient methods or strategies have been developed to overcome this problem.

SUMMARY OF THE INVENTION

The present invention provides a method for detecting the presence of a BARD1 isoform specific to lung cancer and colorectal cancer in a biological sample obtained from a subject comprising the step of detecting in said sample at least one of the BARD1 isoforms specific to lung cancer and colorectal cancer selected from the group comprising isoform π comprising SEQ ID NO: 1, a biologically active fragment thereof, or a sequence having at least 95% homology to SEQ ID NO: 1, and isoform κ comprising SEQ ID NO:2, a biologically active fragment thereof, or a sequence having at least 95% homology to SEQ ID NO:2, wherein the presence of said BARD1 isoforms specific to lung cancer and colorectal cancer in a sample from said subject is an indication that said subject is afflicted with lung cancer and/or colorectal cancer, has an increased risk of lung cancer and/or colorectal cancer, and/or has a risk of recurrence after a treatment for lung cancer and/or colorectal cancer.

The present invention further provides an isolated and/or purified polypeptide comprising SEQ ID NO: 1, a biologically active fragment thereof, or a sequence having at least 95% homology to SEQ ID NO: 1 for use as a biomarker in the method of claims 1 to 6 and an isolated and/or purified polypeptide comprising SEQ ID NO:2, a biologically active fragment thereof, or a sequence having at least 95% homology to SEQ ID NO: 2 for use as a biomarker in the method of claims 1 to 6.

Another object of the present invention is a peptide selected from the group comprising SEQ ID NOs: 13 to 80 for use in a method for detecting the presence of BARD1 isoforms of the present invention.

A further object of the present invention is a kit for detecting the presence of BARD1 isoforms specific to lung cancer and colorectal cancer in a sample obtained from a subject, comprising
- at least one polynucleotide primer or probe wherein said polynucleotide primer or probe is specific for a polynucleotide that encodes at least one of the BARD1 isoforms comprising amino acid sequences selected from the group comprising SEQ ID NOs: 1-7, 105-106, biologically active fragments thereof, and/or sequences having at least 95% homology to SEQ ID NOs: 1-7, 105-106, and/or
- combination of antibodies or fragments thereof that specifically binds to different epitopes of at least one of the BARD1 isoforms comprising amino acid sequences selected from the group comprising SEQ ID NOs: 1-7, 105-106, biologically active fragments thereof, or sequences having at least 95% homology to SEQ ID NOs: 1-7, 105-106, and/or
- at least one peptide selected from the group comprising SEQ ID NOs: 13 to 80.

The present invention also relates to a method for discriminating lung cancer and colorectal cancer from gynecological cancers, said method comprising the step of detecting in a biological sample obtained from a subject at least one of the BARD1 isoforms specific to lung cancer and colorectal cancer selected from the group comprising
- isoform π comprising SEQ ID NO: 1, a biologically active fragment thereof, or a sequence having at least 95% homology to SEQ ID NO: 1, and
- isoform κ comprising SEQ ID NO:2, a biologically active fragment thereof, or a sequence having at least 95% homology to SEQ ID NO: 2.
- wherein the presence of said BARD1 isoforms specific to lung cancer and colorectal cancer is an indication for lung cancer and/or colorectal cancer.

Additionally the present invention relates to antibody, recombinant siRNA and modulator of the biological activity of the BARD1 isoforms of the present invention for use in a method for treating and/or preventing lung cancer and colorectal cancer.

Figure 1F:
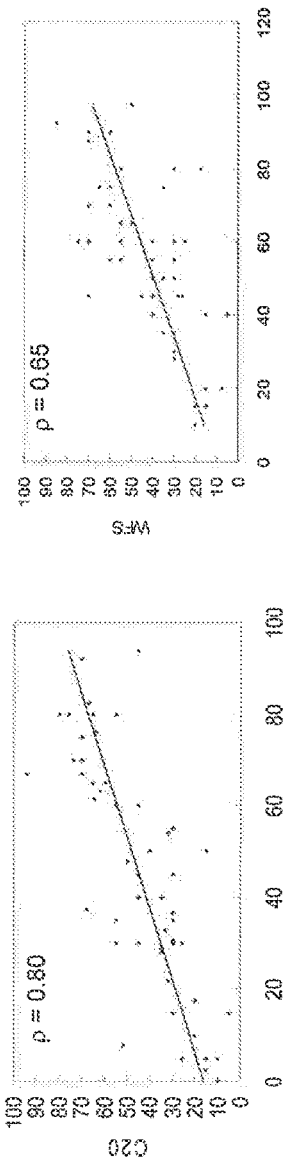
FIG. 1 shows BARD1 expression in NSCLC. Immunohistochemistry was performed on 100 NSCLC cases with BARD1 antibodies N19, C20, PVC, WFS, and BRCA1. (A) Schematic presentation of BARD1 exons (1-11) with protein motifs indicated above as RING finger (RING), ankyrin repeats (ANK), and BRCT domains. Approximate positions of epitopes recognized by the various antibodies are designated (N19, PVC, WFS, C20). (B-D) Examples of immunohistochemical staining using BARD1 antibodies and BRCA1 antibody. BARD1 N19 and C20 showed cytoplasmic granular staining, and sometimes colocalized to the same cells or regions. BARD1 PVC and WFS staining was cytoplasmic or diffusely nuclear and cytoplasmic. BRCA1 staining colocalized with BARD1 N19 staining (B). Examples of no or little staining with PVC and WFS(C) and negligible staining with N-19 and C20 (D) are shown. Scale bar are indicated (upper panels=200 μm; lower panels=100 μm). (E) Observed staining of 73 of 100 NSCLC cases probed with all four N19, PVC, WFS, and C20. "+" indicates positive staining, "−" indicates negative staining. Positive staining with all four antibodies was the most frequent expression pattern. (F) Pairwise comparison of BARD1 N19, PVC, WFS, and C20 staining BARD1 N19 and C20 and PVC and WFS were strongly correlated. Weak or no correlation was observed between N19 and PVC, N19 and WFS, C20 and PVC, C20 and WFS.
Figure 1F:
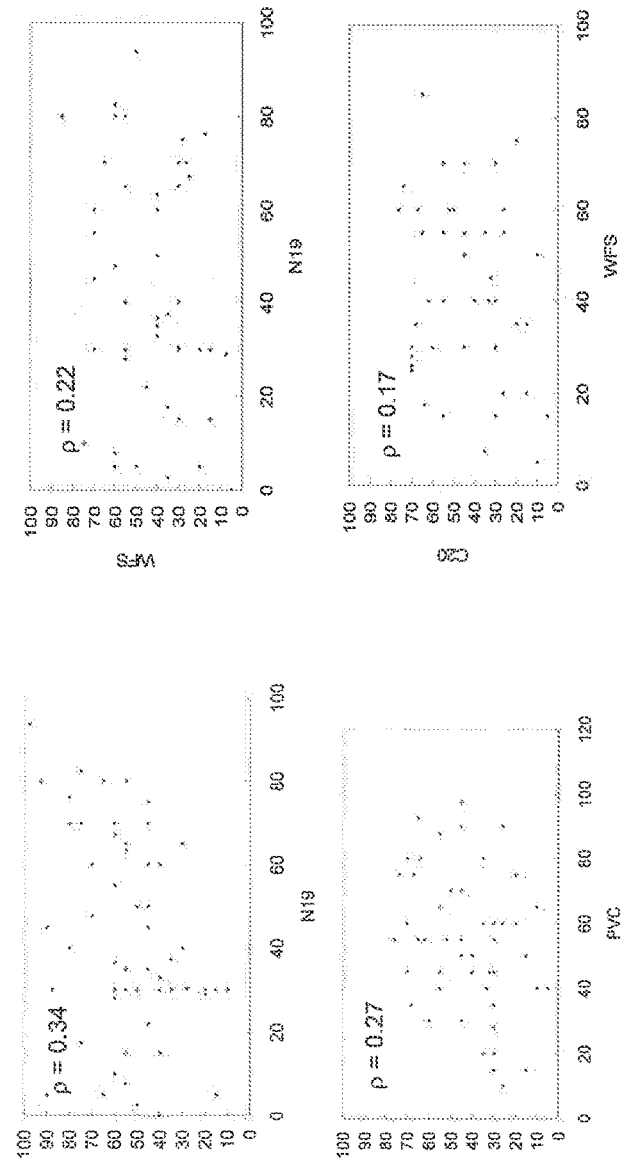

RT-PCR was performed with primers amplifying the entire BARD1 coding region or regions comprising exons 1-4, or 1-6. GAPDH was amplified as control RT-PCR. Molecular size markers (M) are shown on the left. Presumed FL BARD1 and differentially spliced isoforms are indicated on the right. (A) BARD1 RNA expression in normal lung tissue. RT-PCR performed on lung biopsies of individuals with benign lung diseases (see Methods section) shows absence of BARD1 expression in most samples and amplification of individual isoforms (γ, δ, η) in 5 cases of 8. (B) Amplification of FL BARD1 and/or truncated isoforms using forward primer in exon 1, and reverse primer in exon 11 or exon 4. Examples of pairs of normal peri-tumour (N) and tumour (T) tissue are shown for tissues from male and female patients. Presumed FL BARD1 and differentially spliced isoforms are indicated on the right. Normal and tumour tissues express the same pattern of isoforms. (C) Amplification of exons 1 to 6 was performed to distinguish FL BARD1, β, and novel isoforms κ and π. Isoform π is specifically expressed in tumours, but not or weakly in normal tissues. (D) Expression of Estrogen Receptor α, determined by RT-PCR, was found in most cases. Similar expression levels were found in normal and tumour, in male and female samples. (E) Structure of known BARD1 isoforms and lung cancer specific novel forms isoform κ and π. Schematic exon (1 to 11) structure of FL BARD1 and protein features (RING, ANK, BRCT) and nuclear localization signals (NLS) and positions of primers are indicated. Schematic presumed protein structures of isoforms are shown below in grey, noncoding exons in white, and alternative open reading frames (β, γ and η) in light grey dots (points). Novel isoform κ is shown with deletion of exon 3 and presumed translation start (ATG) within exon 4. Novel isoform π is designed with deletion within exon 4, and known BARD1 mutations and polymorphisms that map within this region are indicated. Designated names of isoforms are shown on the left, size (amino acids) and molecular weights (MW) on the right side.

Figure 5:
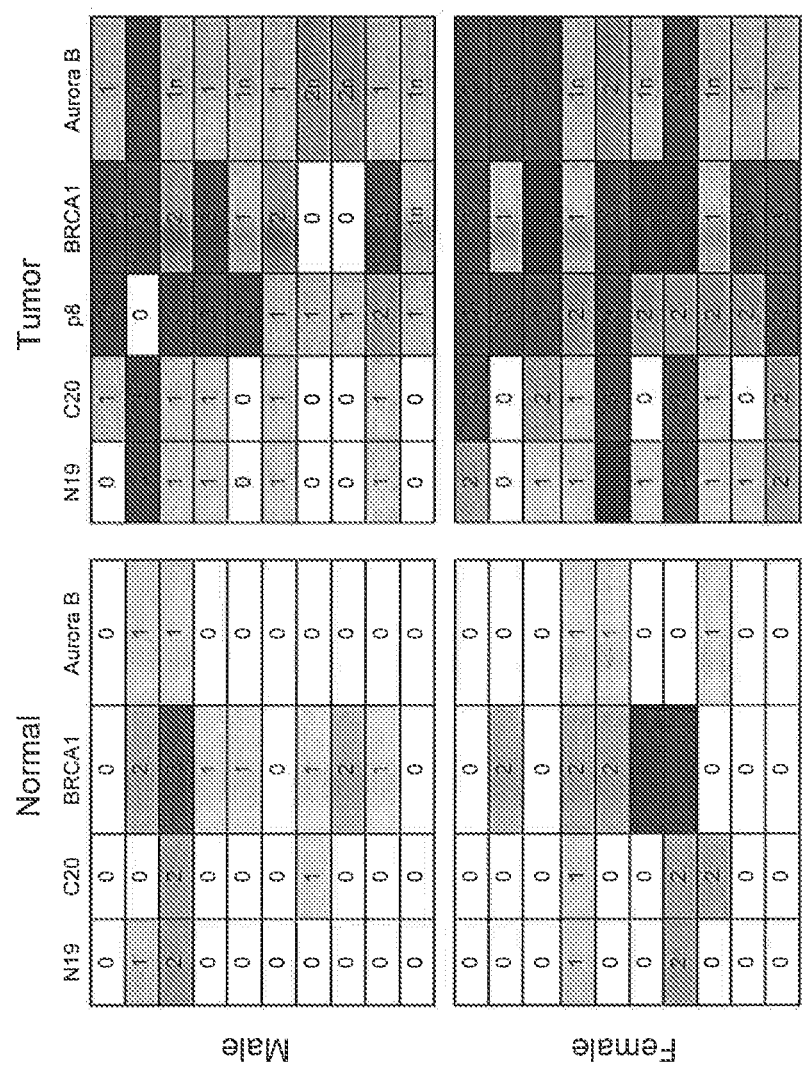

FIG. 5 shows comparison of BARD1, BRCA1 and Aurora B expression morphologically normal peri-tumour (left) and in tumour tissues (right) of female and male NSCLC patients. BARD1 (N19 and C20) and C-terminal-specific antibody p8, BRCA1, and Aurora B antibody staining was used for immunohistochemistry. Denotation n=nuclear staining.

Figure 6:
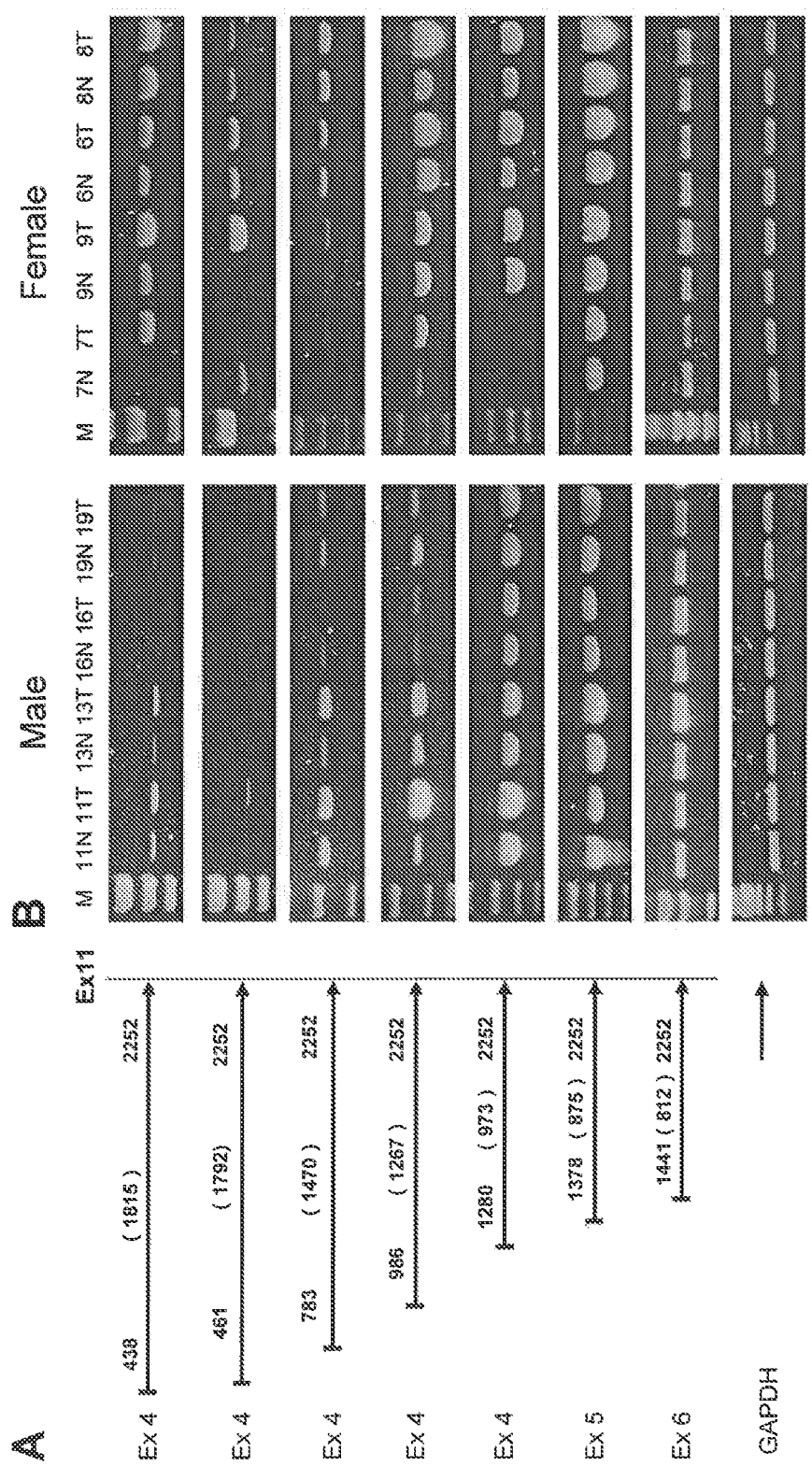

FIG. 6 shows alternative splicing and/or transcription initiation within exon 4. (A) Diagram of various fragments of BARD1 amplified with forward primers within exon (Ex) 4, exon 5, and exon 6 (on the left), and reverse primer in exon 11 (on the right). Position of primers and expected size of amplified band is marked in parentheses (bp). (B) Amplification of BARD1 transcripts in human lung tumour tissues (T) and adjacent normal peri-tumour tissues (N) of male (left panel) and female (right panel) NSCLC patients with primers indicated in A are shown. Note that amplification with primers within exon 4 is variable in different samples, but all samples can be amplified with primers in exon 5 or exon 6. Variations in BARD1 mRNA and protein expression might be due to alternatively spliced or differential initiation of transcription in this region.

Figure 7:
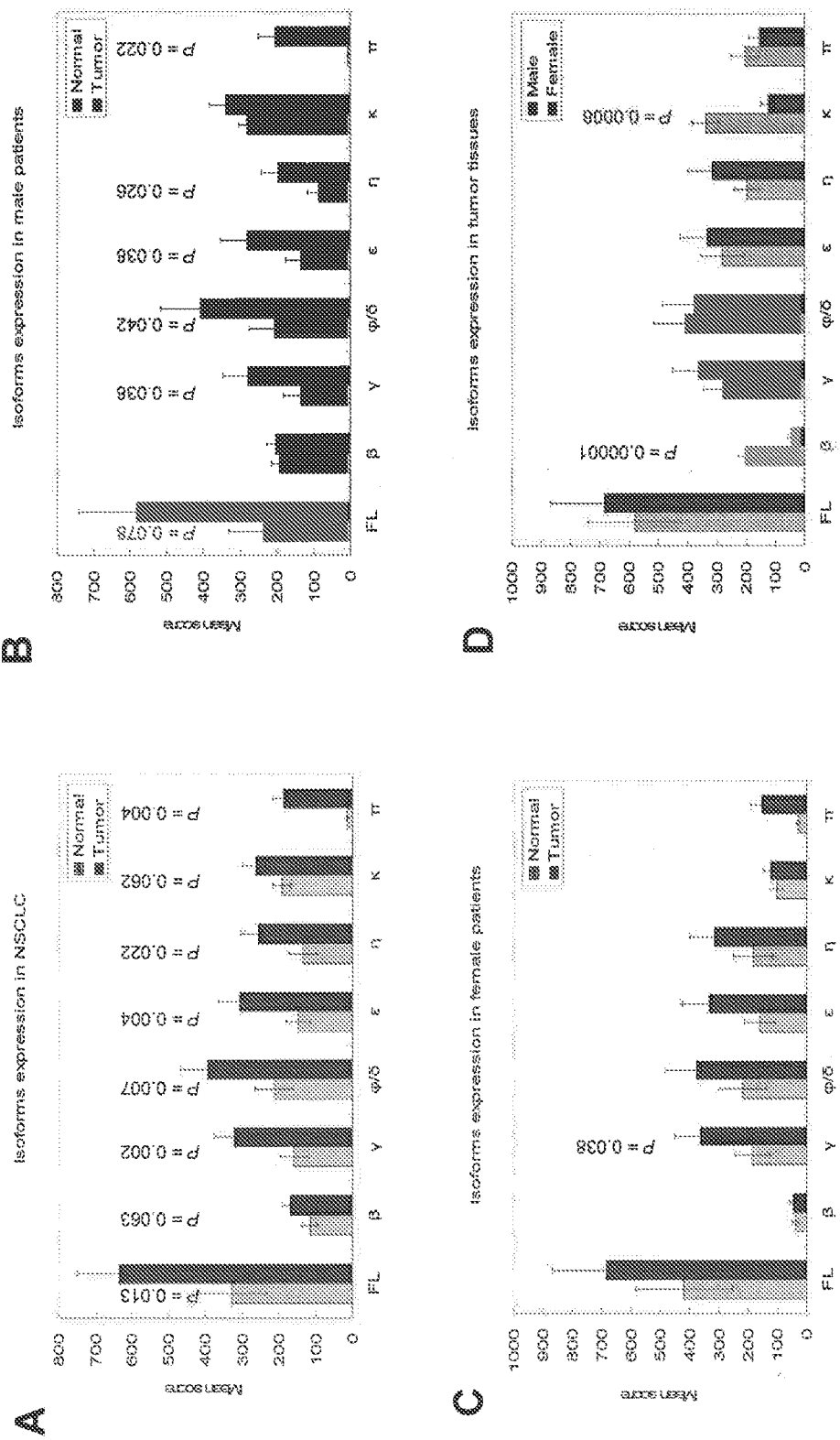

FIG. 7 shows comparison and correlation of BARD1 mRNA isoform expression in tumour (Tumour) and peri-tumour (Normal) tissues of female and male patients. FL BARD1 and BARD1 isoforms of 20 pairs of tumour/morphologically normal tissue samples, including 10 males and 10 females, were scored and are presented. Expression was quantified with ImageJ software (see Methods section). The results are shown in the figures as means±SE (standard error) of values. (A) Comparison of FL BARD1 and isoforms in peri-tumour and tumour tissues. All forms are upregulated in tumours with statistical significance, with exception of isoform β and κ. (B-C) FL BARD1 and BARD1 isoforms are more abundant in tumour than in peri-tumour tissues, in both males (B) and females (C). (D/E) Comparison of BARD1 expression between male and female in tumour tissues (D) and in normal tissues (E). BARD1 isoform β and κ are more expressed in tissues from males than females in tumour and peri-tumour tissues. This is statistically significant. FL BARD1 and BARD1 isoforms γ, ε, and η may be more expressed in tissues from females than from males, in tumour and peri-tumour tissues, but this is not statistically significant. (F) Comparison of FL BARD1 and isoforms in young (<60 years) and old (>60 years) patients groups. FL BARD1 and isoform γ are up regulated in young (<60 years) patients. This is statistically significant.

Figure 8:
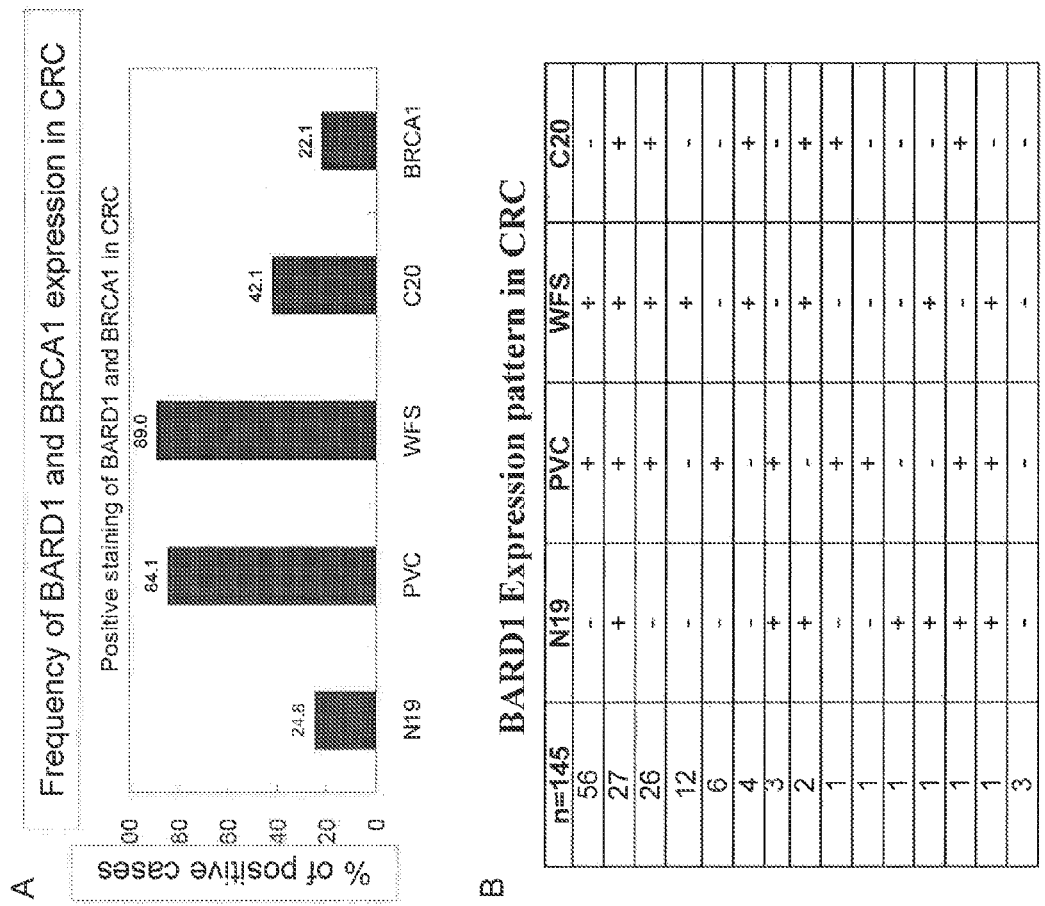

FIG. 8 shows examples of immunohistochemistry of BARD1 and BRCA1 expression in colorectal cancer. Immunohistochemistry was performed on samples of 148 colorectal cancer cases with BARD1 antibodies N19, C20, PVC, WFS, and BRCA1. All samples were presented as tissue microarray with tetramerous for each of the cases. One hundred and forty-five samples were eligible for analysis after immunohistochemistry assay.

(A) Frequency of positive staining cases with antibodies for BARD1 and BRCA1. Positive staining rates for each of the four antibodies were variable. BARD1 N19 and C20 stainings were less frequent, as well as BRCA1 staining. BARD1 PVC and WFS positive stainings were observed in most of the colorectal cancer cases. (B) BARD1 expression pattern in colorectal cancer. Expression patterns were obtained with four BARD1 antibodies based on positive (+) and negative (−) staining for each of the cases. PVC and WFS positive, but N19 and C20 negative staining was the most frequent expression pattern, "all four antibodies positive" staining was the second, N19 negative while PVC, WFS and C20 positive staining was the third most frequently observed expression pattern. (C-F) Examples of immunohistostaining using BARD1 antibodies and BRCA1 antibody. BARD1 N19 and C20 showed cytoplasmic granular staining, and co localized to the same cells or regions. BARD1 PVC and WFS staining was diffusely cytoplasmic. BRCA1 staining was granular in both cytoplasm and nucleus. Examples of positive staining with BARD1 antibodies and BRCA1 antibody (C), negligible staining with N-19 and C20 (D), positive staining with all four BARD1 antibodies (E) and negative staining with N19 (F) are shown. Scale bars are shown (upper panels=200 μm; lower panels=50 μm).

Figure 9A:
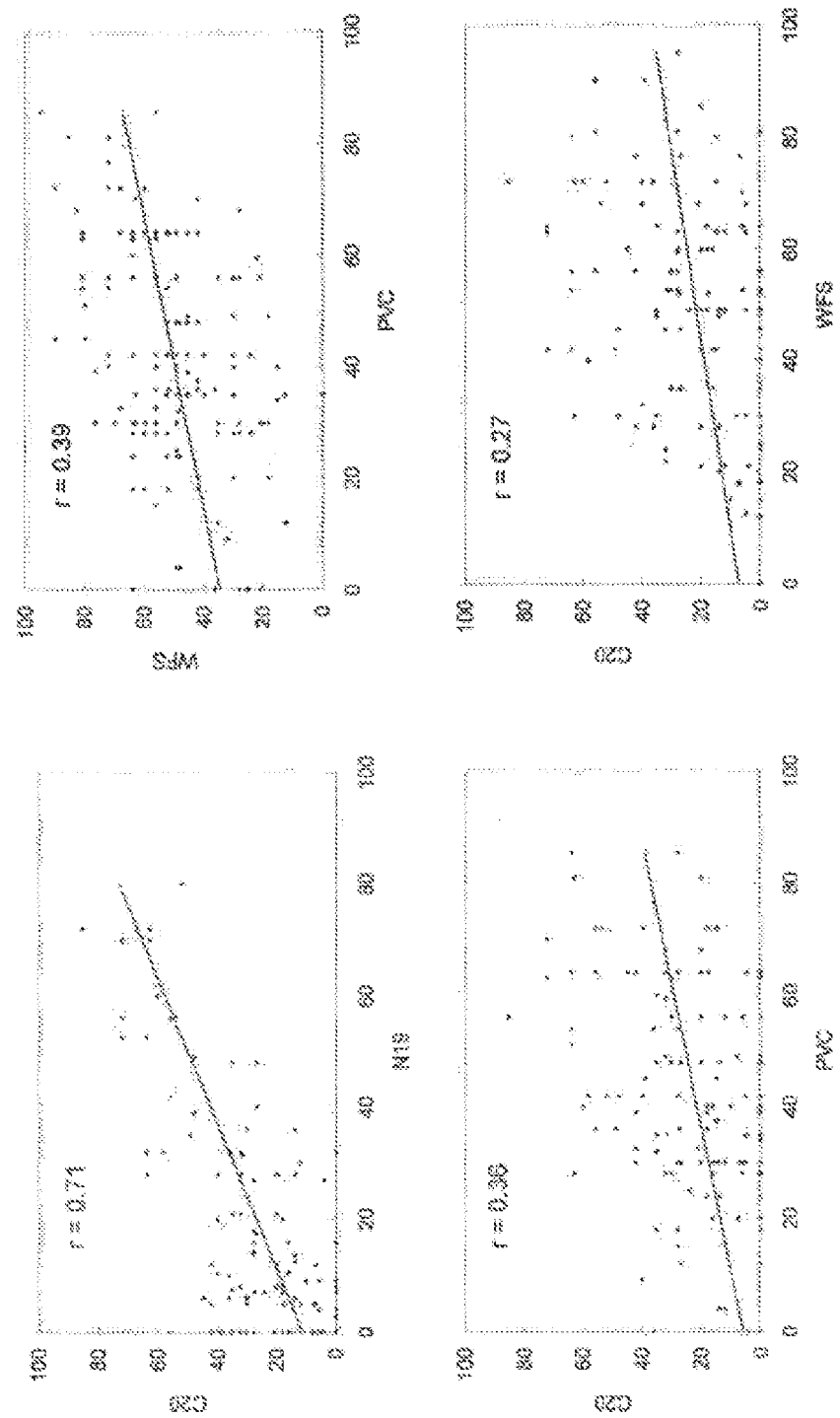
Figure 9A:
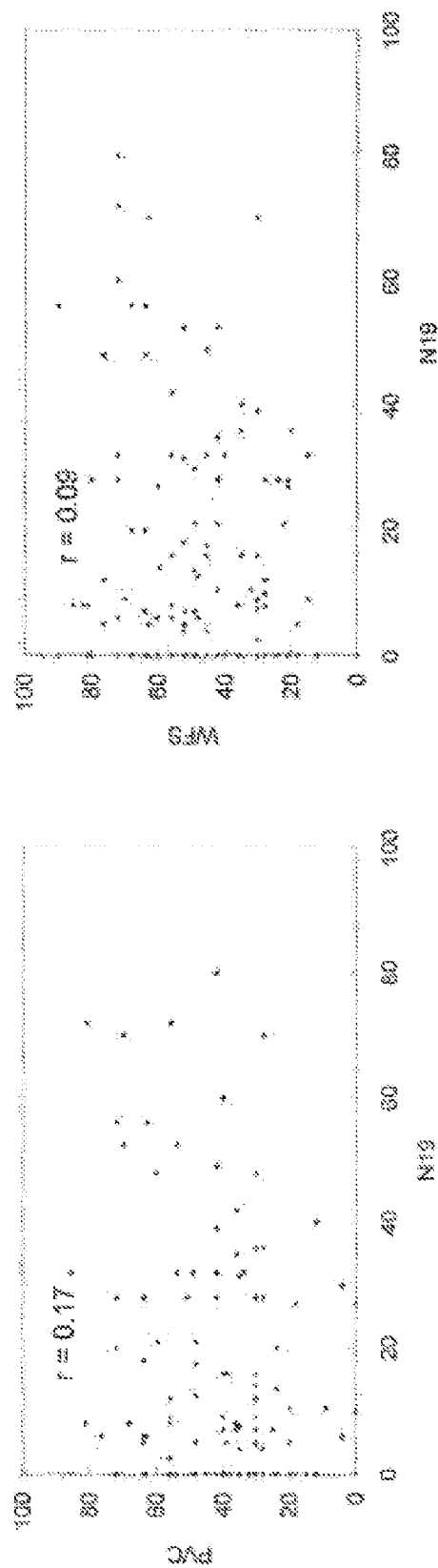

FIG. 9 shows correlation between distinct antibody staining for BARD1 and BRCA1 in colorectal cancer. (A) Correlation of BARD1 N19, PVC, WFS, and C20 staining. BARD1 N19 and C20 staining was strongly correlated, PVC and WFS, PVC and C20, and WFS and C20 staining was weakly correlated. No correlation was observed between N19 and PVC, and N19 and WFS. (B) Correlation of antibody staining of BRCA1 and BARD1. BRCA1 staining was not correlated with any staining of the four BARD1 antibodies.

Figure 10:
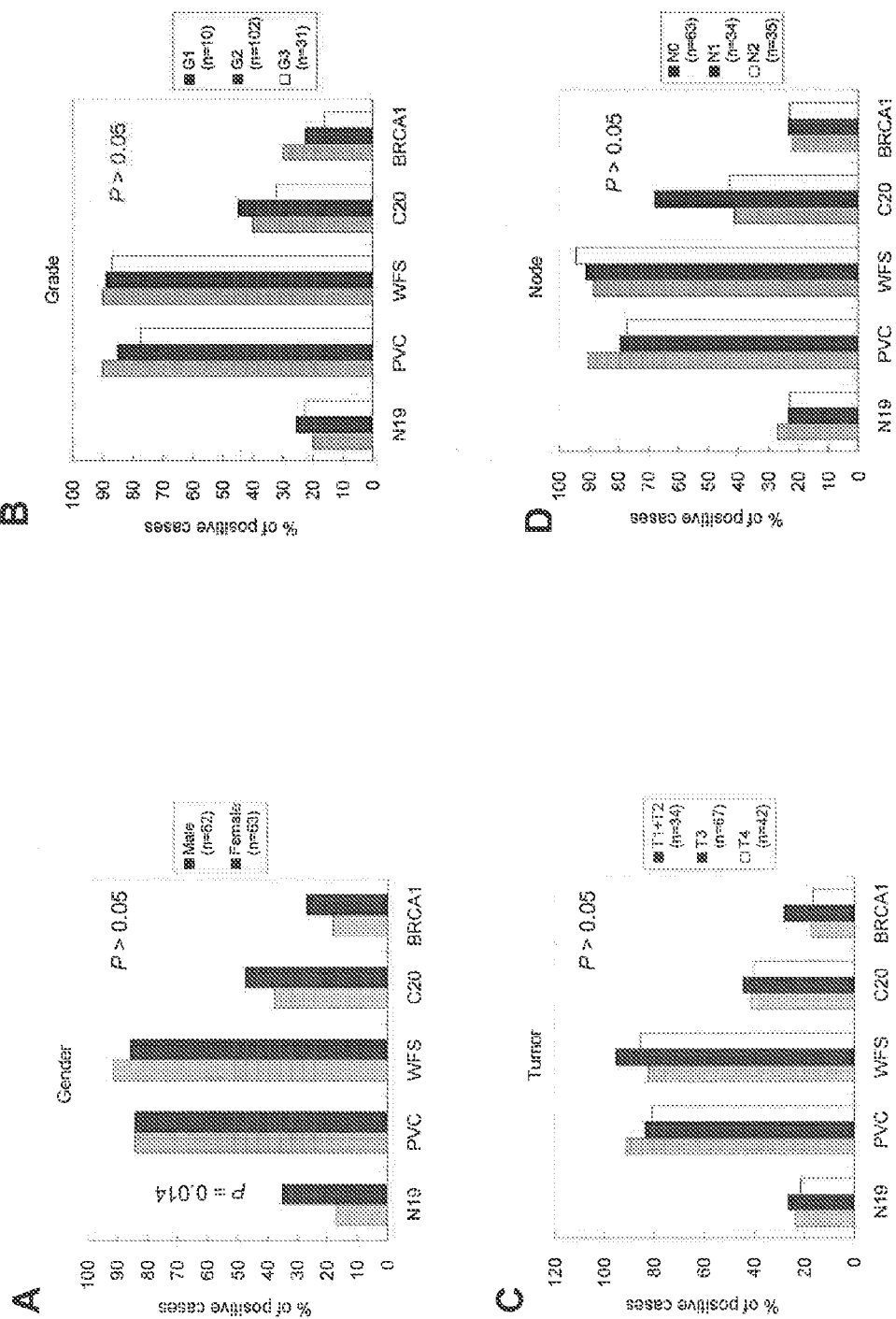
Figure 10:
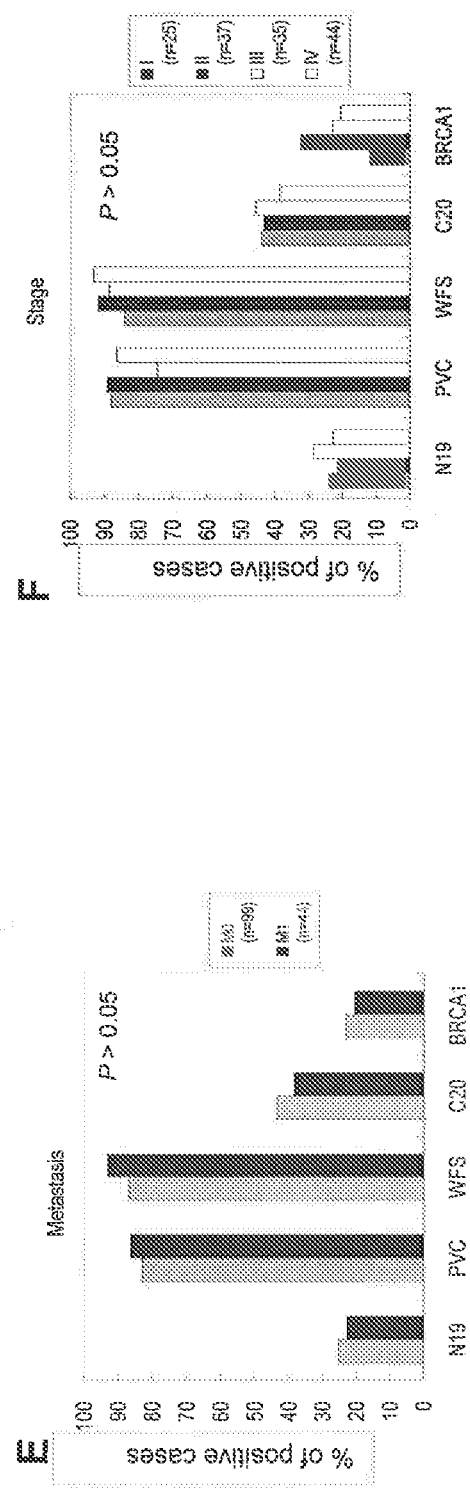

FIG. 10 shows correlation of distinct epitopes of BARD1 and BRCA1 expression with clinical variables in colorectal cancer. BARD1 N19 positive staining was more frequent in female gender (P=0.014) (A). No correlation were found between different antibodies of BARD1 and BRCA1 staining and tumour histopathological grade (Grade) (B), tumour size or nearby tissue invasion (Tumour) (C), lymph node involvement (Node) (D), distant metastases (Metastasis) (E) and tumour stage (Stage) (F). The P value is obtained by the χ2 test.

Figure 11:
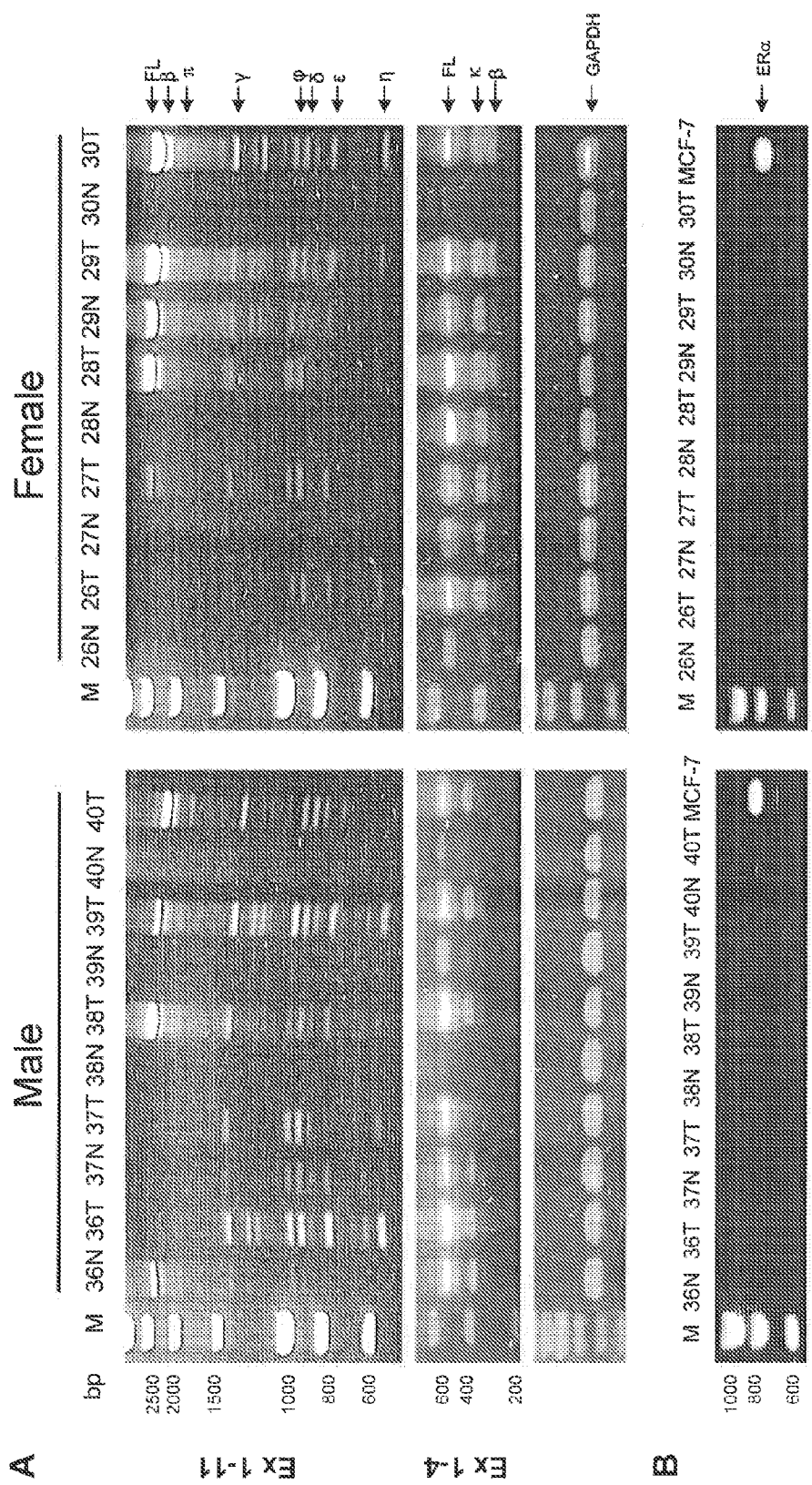

FIG. 11 shows expression and structure of BARD1 transcripts in colorectal cancer tissue (T) and normal peritumour tissue (N). (A) Amplification of FL BARD1 and/or truncated isoforms using forward primer in exon 1, and reverse primer in exon 11 (Ex 1-11) or exon 4 (Ex 1-4). As examples, pairs of peri-tumour and tumour tissues of 5 male and 5 female patients are shown. Glyceraldehyde 3-phosphate dehydrogenase (GAPDH) expression is shown for the same samples as standard. Molecular marker is shown on the left (M). Presumed FL BARD1 and truncated isoforms are indicated on the right. Peri-tumour and tumour tissues expressed different patterns of isoforms: less frequent expression in peri-tumour tissues than tumour tissues. Two novel isoforms, κ and π, also identified in NSCLC, were expressed in colorectal cancer. (B) Amplification of estrogen receptor α (ERα) in same samples, MCF-7 was used as positive control (right). No ERα expression was observed in colorectal tissues, neither in peri-tumour nor in tumour samples of males and females.

Figure 12:
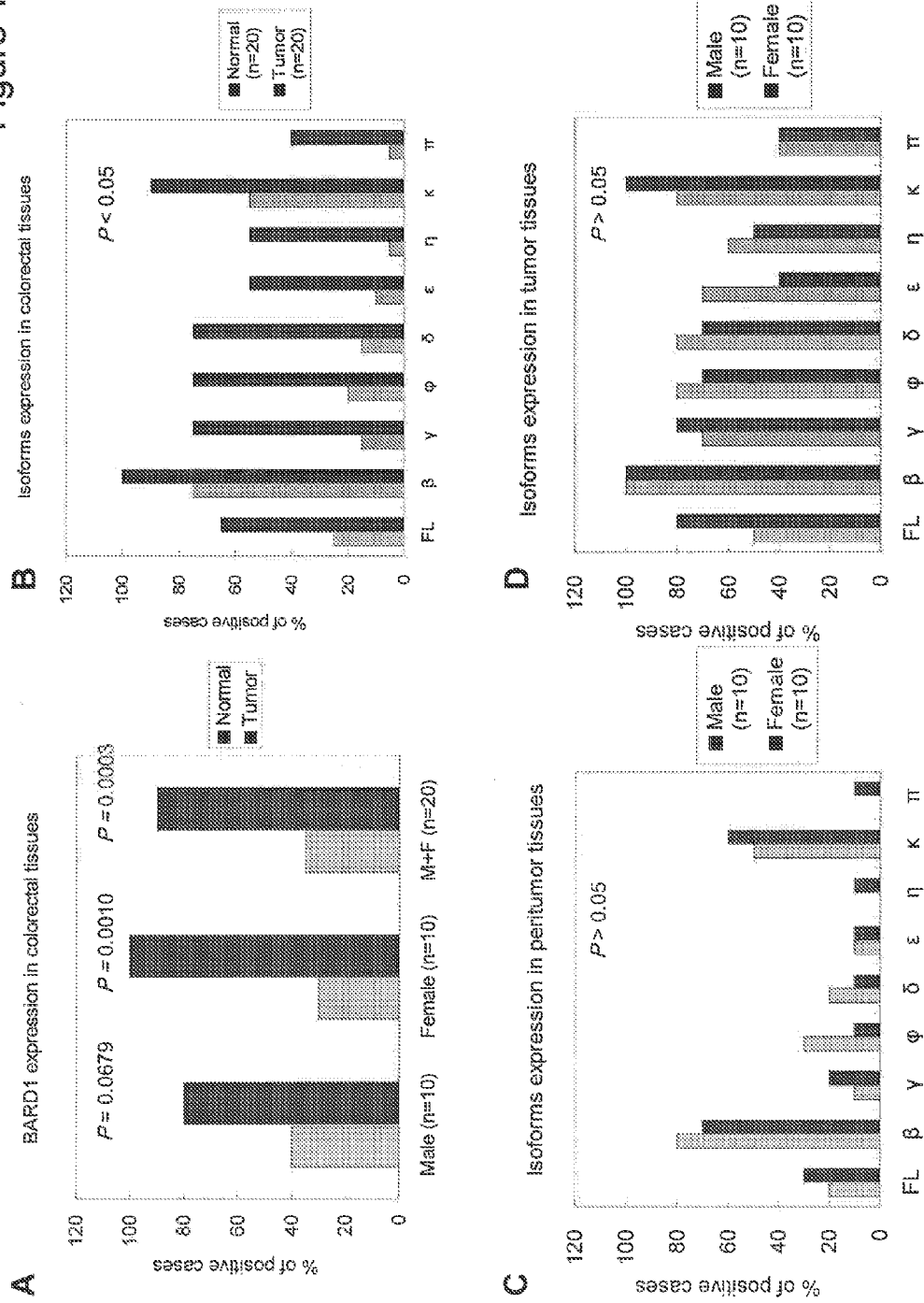

FIG. 12 shows comparison of BARD1 mRNA isoform expression in tumour (Tumour) and peri-tumour (Normal) tissues of male and female patients with colorectal cancer. FL BARD1 and BARD1 isoforms of 20 pairs of tumor/peri-tumor tissue samples of colorectal cancer, including 10 males and 10 females, were scored and are presented. Expression was quantified based on presence or absence of expression in each of the peri-tumour or tumour samples (A), and for each of the isoforms (B, C, D). (A) Comparison of BARD1 expression in peri-tumour and tumour tissues, including in males, females and in combined samples, based on absence or presence of any of the forms of BARD1. BARD1 expression was more abundant and more frequent in tissues from tumours than peri-tumours (P=0.0003), both in females (P=0.0010) and in males (P=0.0679). (B) Comparison of FL BARD1 and isoform expression in peri-tumour and tumour tissues. All forms were upregulated in tumours with statistical significance (P<0.05 for all). (C/D) Comparison of FL BARD1 and isoform expression in colorectal tissues from males and females. The expression of FL BARD1 and isoforms was similar in tissues from males and females, both in pen-tumour (C) and in tumour (D) tissues (P>0.05 for all). The P value is obtained by the χ2 test.

Figure 13:
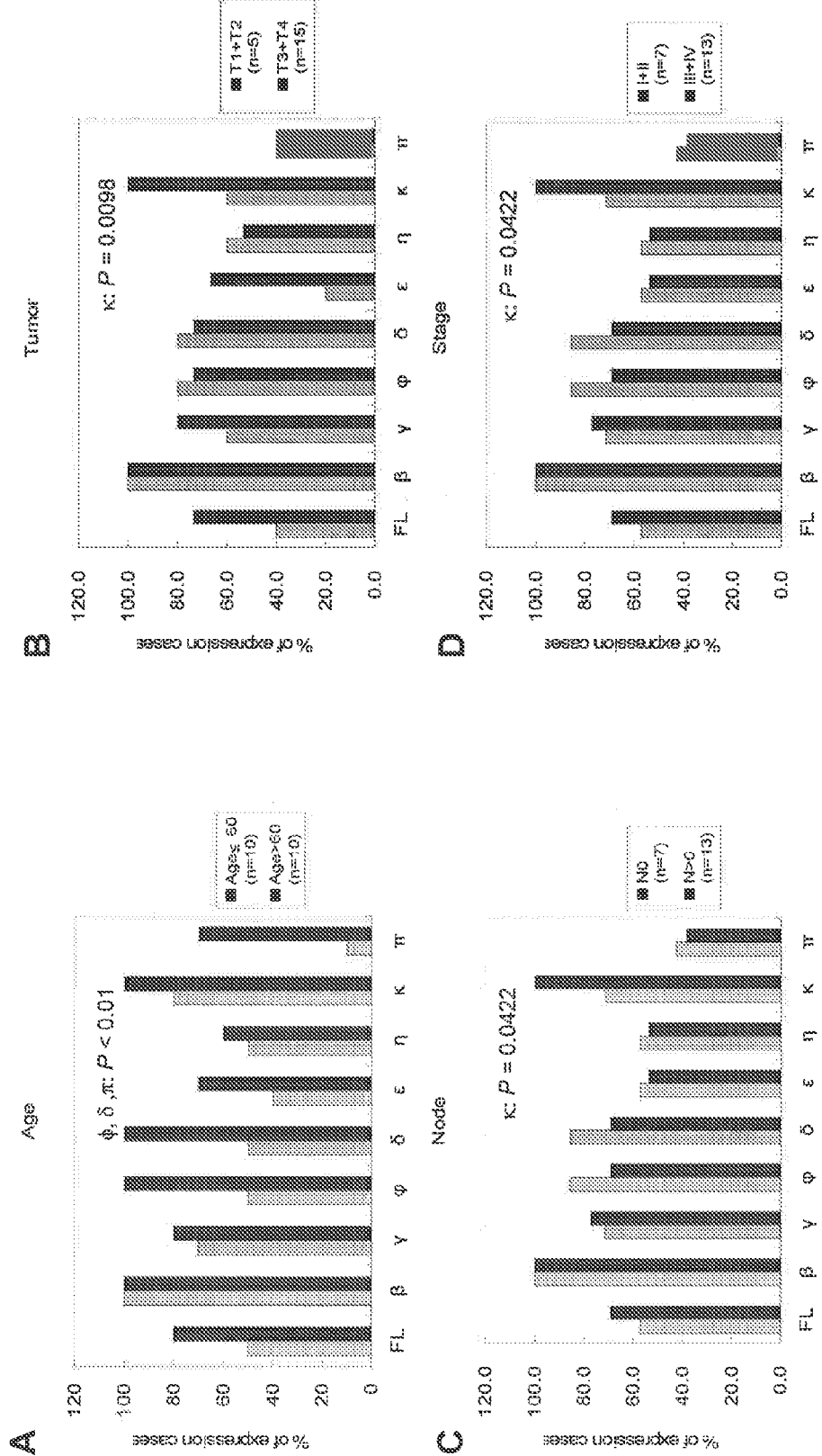

FIG. 13 shows correlation of FL BARD1 and isoforms mRNA expression with clinicopathological variables in colorectal cancer. (A) Comparison of FL BARD1 and isoform expression in younger (≤60 years) and older (>60 years) patients. FL BARD1 and all isoforms, except isoform β, were more up regulated in older than in younger patients. Specially, expression of isoforms φ, δ, and π were significantly associated with older patients (P<0.01). (B-E) Comparison of FL BARD1 and isoforms expression with primary tumor and lymph node status, and tumor stage and grade. BARD1 isoform κ expression was significantly associated with large tumor size or nearby tissue invasion (B), lymph node involvement (C), and advanced stage (stage III and IV) (D). No correlation was found between BARD1 isoforms expression and tumor histopathological grade (E). The P value is obtained by the χ2 test. Comparison for P>0.05 was not shown.

Figure 14:
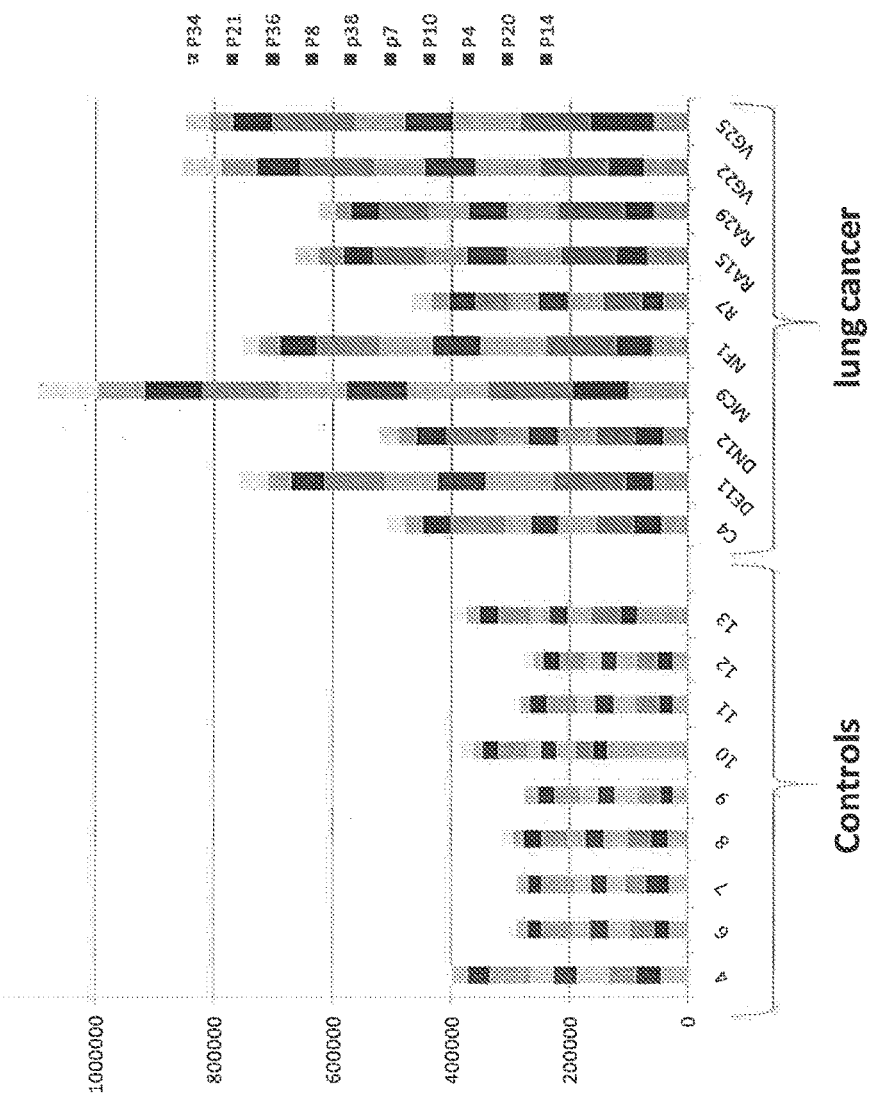

FIG. 14 shows an example of ELISA test for BARD1 isoform-specific antibodies detection in blood or serum.

Figure 15:
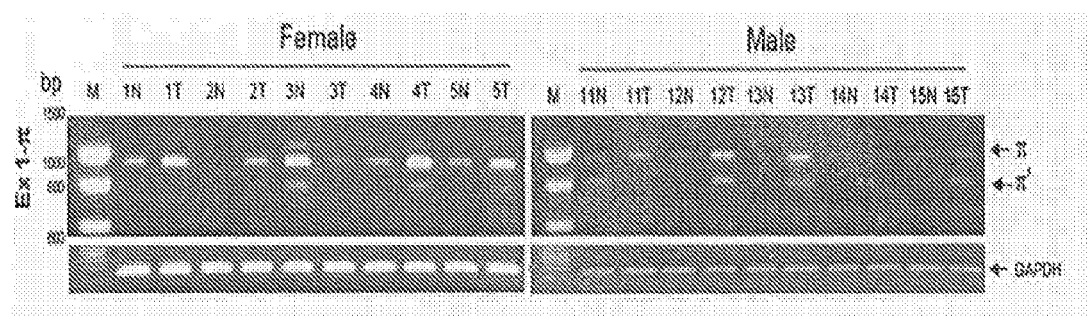

FIG. 15 shows amplification of isoform π with primers at ATG and deletion junction in π. A second isoform, π', derived from additional deletion of exon 2 is identified.

Figure 16:
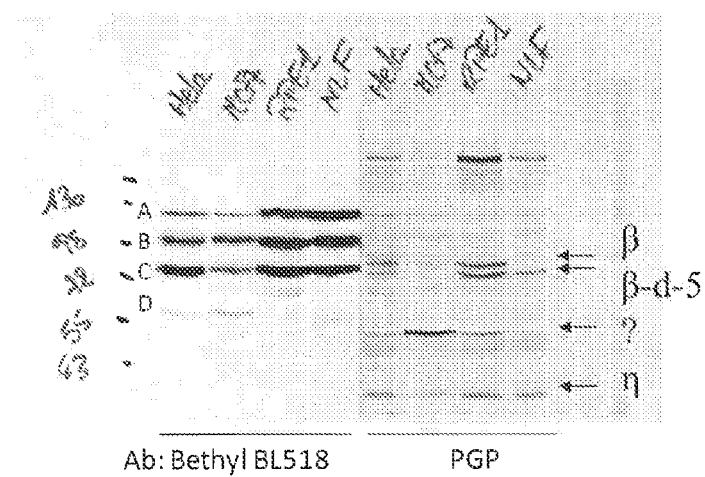

FIG. 16 shows Western blot with anti-Bard1 antibodies on HeLa, MCF7, RPE1 and NLF cells. Ab Bethyl BL518 (BL) recognizes epitopes encoded in mid exon 4. Ab PGP was generated against epitopes encoded by β-specific alternative ORF in exon 1. Recognizes BARD1 isoform β and BARD1 isoform β-d-5 (β') and BARD1 isoform η.

Figure 17:
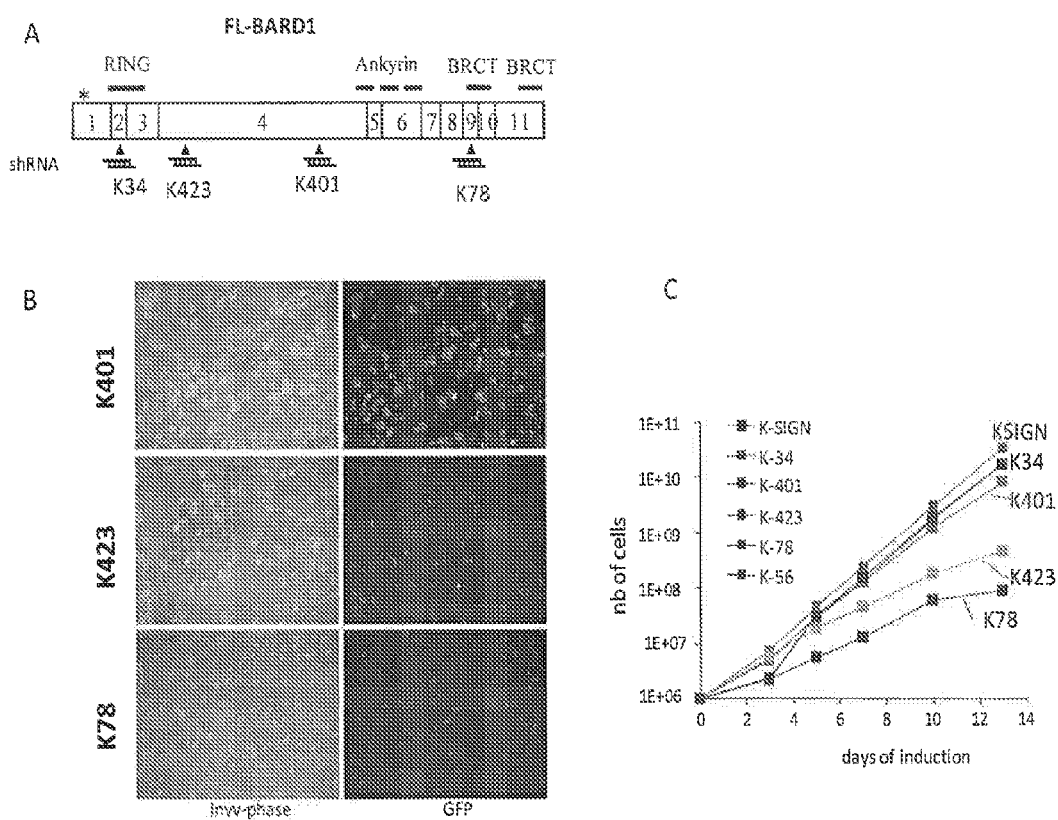

FIG. 17 shows siRNA repression of BARD1 isoforms. A) Location of siRNA target sequence. Two siRNAs in exon 4 were used, K401 and K423. K401, located within the deletion of isoform pi, K423 is upstream of deletion. B-C) K401 had less effect on growth than K423. B) siRNA expression is coupled to GFP expression. Many positive cells are growing in K401 expressing cells, few are growing in K423 expressing cells. C) Growth curves confirm that K423 represses cell growth as efficiently as previously reported K78, which targets all forms of BARD1.

Figure 18:
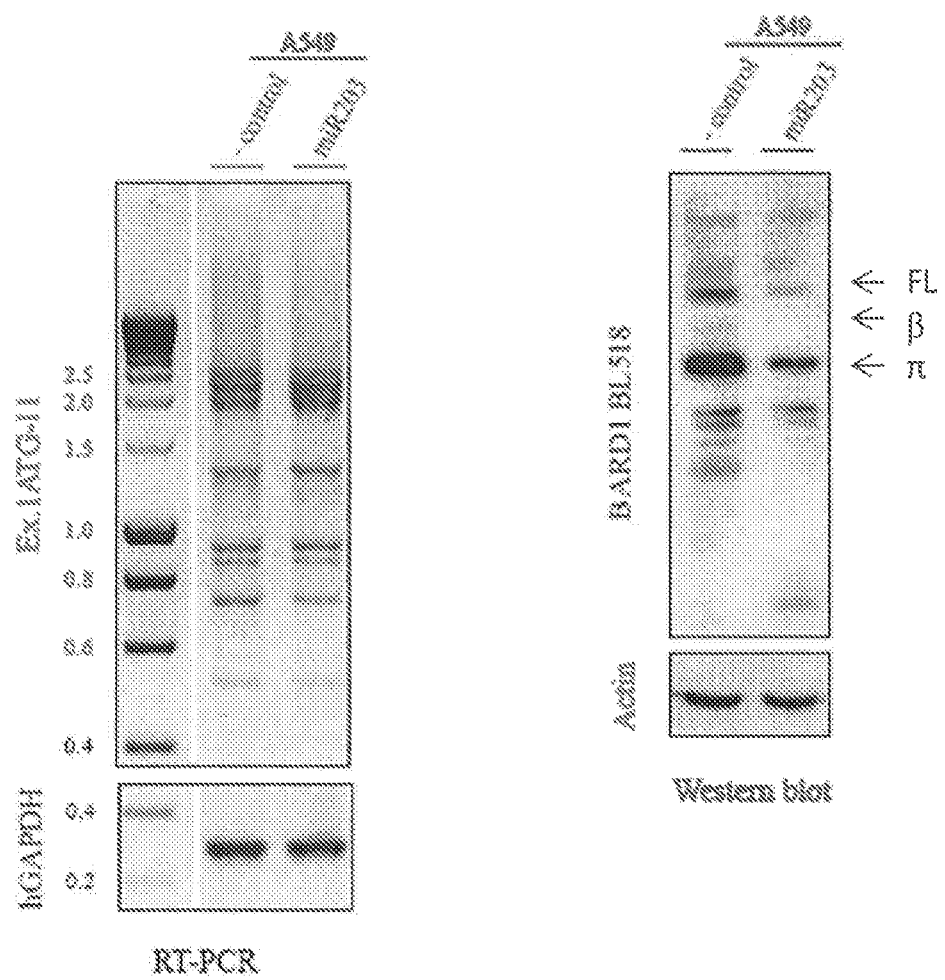

FIG. 18 shows microRNAs affect BARD1 and BARD1 isoform expression. RT-PCR shows that all forms of BARD1 are slightly repressed by miR-203. Western blot shows strong repression of FL, β and π by miR-203 overexpression.

DETAILED DESCRIPTION OF THE INVENTION

Although methods and materials similar or equivalent to those described herein can be used in the practice or testing of the present invention, suitable methods and materials are described below. All publications, patent applications, patents, and other references mentioned herein are incorporated by reference in their entirety. The publications and applications discussed herein are provided solely for their disclosure prior to the filing date of the present application. Nothing herein is to be construed as an admission that the present invention is not entitled to antedate such publication by virtue of prior invention. In addition, the materials, methods, and examples are illustrative only and are not intended to be limiting.

In the case of conflict, the present specification, including definitions, will control.

Unless defined otherwise, all technical and scientific terms used herein have the same meaning as is commonly understood by one of skill in art to which the subject matter herein belongs. As used herein, the following definitions are supplied in order to facilitate the understanding of the present invention.

The term "comprise" is generally used in the sense of include, that is to say permitting the presence of one or more features or components.

As used in the specification and claims, the singular form "a", "an" and "the" include plural references unless the context clearly dictates otherwise. For example a BARD1 isoform means at least one BARD1 isoform.

As used herein the term "isoform" is any of several different forms of the same protein, such as BARD1 protein in the present invention. Different forms of a protein, such as BARD1, may be produced from related genes, or may arise from the same gene by alternative splicing. A large number of isoforms are caused by single-nucleotide polymorphisms or SNPs, small genetic differences between alleles of the same gene. These occur at specific individual nucleotide positions within a gene.

As used herein the terms "subject" or "patient" are well-recognized in the art, and, are used herein to refer to a mammal, and most preferably a human. In some embodiments, the subject is a subject in need of treatment or a subject with lung and/or colorectal cancer. However, in other embodiments, the subject can be a normal subject who has not developed lung and/or colorectal cancer symptoms or the subject who has already undergone a treatment against lung and/or colorectal cancer. The term does not denote a particular age or sex. Thus, adult and newborn subjects, whether male or female, are intended to be covered.

As used herein, the terms "peptide", "protein", "polypeptide", "polypeptidic" and "peptidic" are used interchangeably to designate a series of amino acid residues connected to the other by peptide bonds between the alpha-amino and carboxy groups of adjacent residues.

Contrary to what was expected, the Applicants have surprisingly identified in each sample from a 100 non-small cell lung cancer (NSCLC) and a 165 colorectal cancer patient cohort two new additional BARD1 isoforms besides already known isoforms α, γ, η, γ, ε, φ, δ and θ. Another surprising feature is that isoform α was absent in each sample from a 100 NSCLC and a 165 colorectal cancer patient cohort. These new isoforms were denoted κ and π. Indeed BARD1 isoforms expressed similar pattern in tumour tissues of NSCLC and colorectal cancer, they all expressed two new isoforms κ and π, which differ from BARD1 isoforms identified in gynaecological cancers (WO 2008/119802). This finding indicated that abnormal expression of BARD1 might be different in female hormone dependent and non-female hormone dependent tumour tissues.

New isoform κ carries a deletion of exon 3, Translation of exon 2 into exon 4 is not in-frame, but translation may be initiated within exon 4. The resulting protein product would be similar in antibody reactivity to isoform β.

Figure 4:
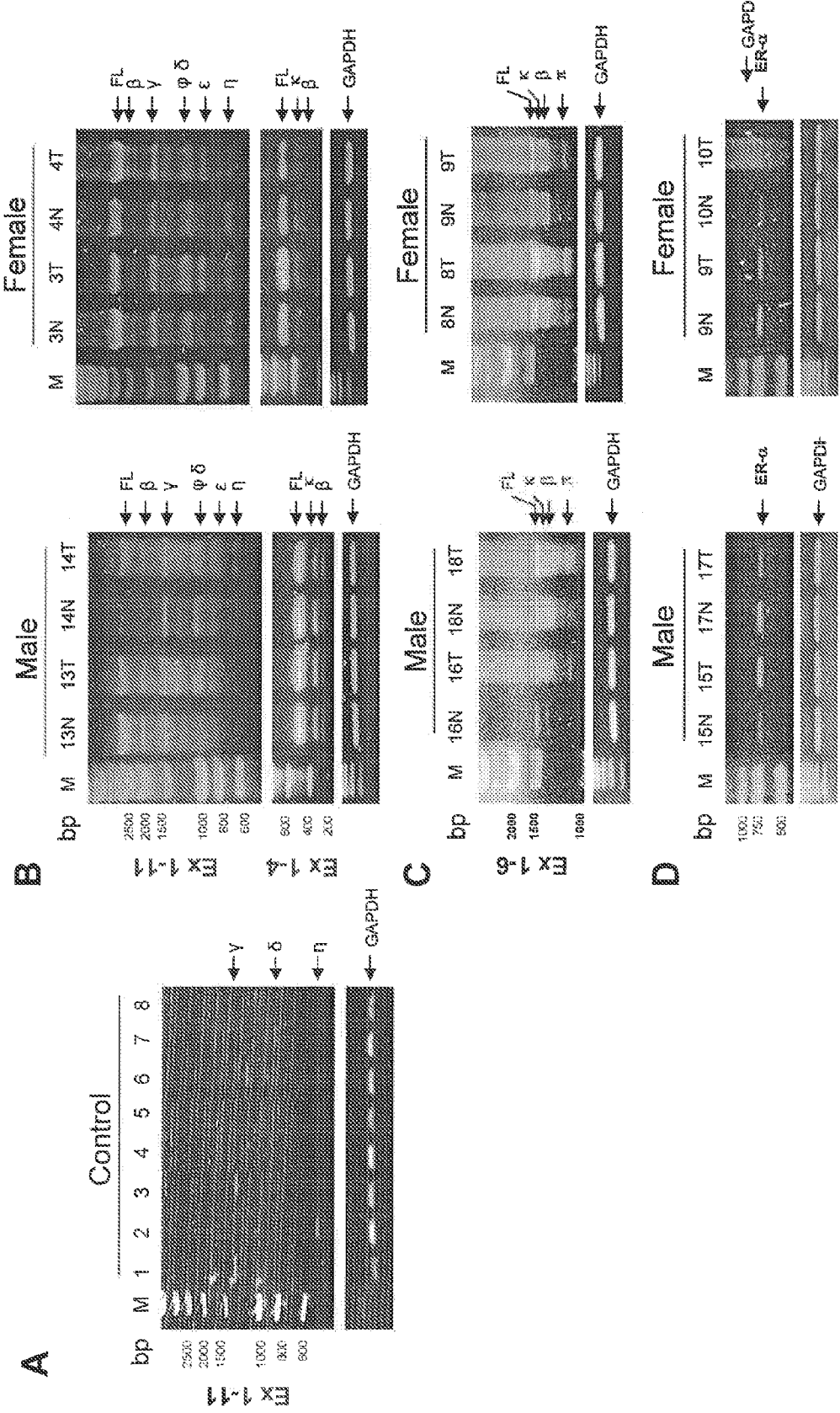
FIG. 4 shows expression and structure of BARD1 transcripts in human lung tumour and peri-tumour tissues. (A-D)
Figure 4E:
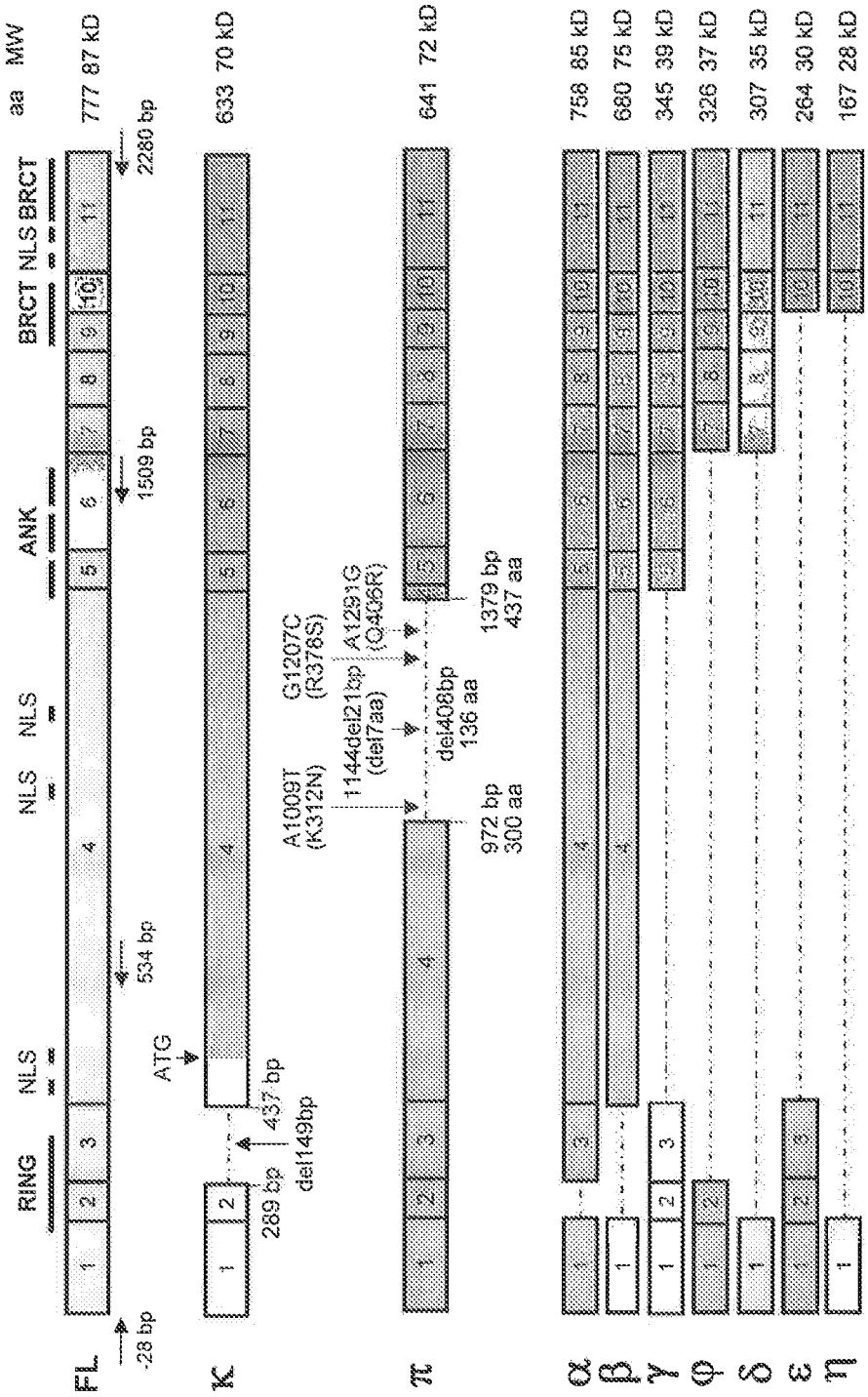

New isoform π carries a deletion of 408 bp, encoding amino acids 301 to 436 within exon 4. Translation of isoform π would result in a protein reacting with antibodies PVC and WFS, but lacking important NLSs (FIG. 4C, E and FIG. 6). Isoform π is derived from a novel splicing mechanism that generates a partial deletion of exon 4, but retains the exons 1-3 and the beginning of exon 4, thus maintaining the BRCA1 binding RING finger domain. Isoform π retains the exons 1 to 3 and the beginning of exon 4, thus the epitopes recognized by PVC and WFS, a combination of epitopes not found in any other isoform. Isoform π can be detected with antibodies PVC and WFS; these antibodies show increased staining in advanced mouse lung tumours. Thus, isoform π may be an oncogenic driver of tumour progression in NSCLC. The partial deletion of exon 4 in isoform π might be an important region, as it harbors several cancer-associated mutations and NLS (FIG. 4E), which might explain the cytoplasmic localization of PVC and WFS staining Aberrant intracellular localization could affect protein modifications, e.g. phosphorylation and protein-protein interactions.

Isoform π seems particularly important for lung cancer as it is the only isoform that is significantly up regulated in tumour tissue and is absent or only weakly expressed in peri-tumour tissue, while all other BARD1 isoforms were expressed in tumour and peri-tumour tissue alike (FIG. 4B; FIG. 7). The partial deletion of exon 4 leads to loss of an important NLS on BARD1 that might explain the cytoplasmic localization.

An additional isoform π', derived from deletion of exon 2, was co-expressed with isoform π in lung cancer and colorectal cancer.

The Applicants showed that FL BARD1 (Full Length BARD1) and spliced isoforms are expressed in tumour and normal peri-tumour tissue and might contribute to tumour initiation and progression. However, isoform π is specifically expressed in tumours and might be involved in oncogenic progression. FL BARD1 is expressed on the mRNA level, but there is no protein translation of FL BARD1. Thus on the protein level, BARD1 isoforms, but not FL BARD1, are expressed in each sample from a 100 NSCLC and a 165 colorectal cancer patient cohort. Isoform expression and localization is not correlated with BRCA1, indicating that the E3 ubiquitin ligase functions of the BRCA1-BARD1 heterodimer are jeopardized in both types of cancer. BRCA1 protein stability and localization largely depend on BARD1. Absence of FL BARD1, causing absence of the tumour suppressor functions of BRCA1-BARD1, leads to genomic instability and resistance to apoptosis. Besides this effect of loss of FL BARD1, the over expressed differentially spliced BARD1 isoforms may be drivers of tumorigenesis.

Figure 3:
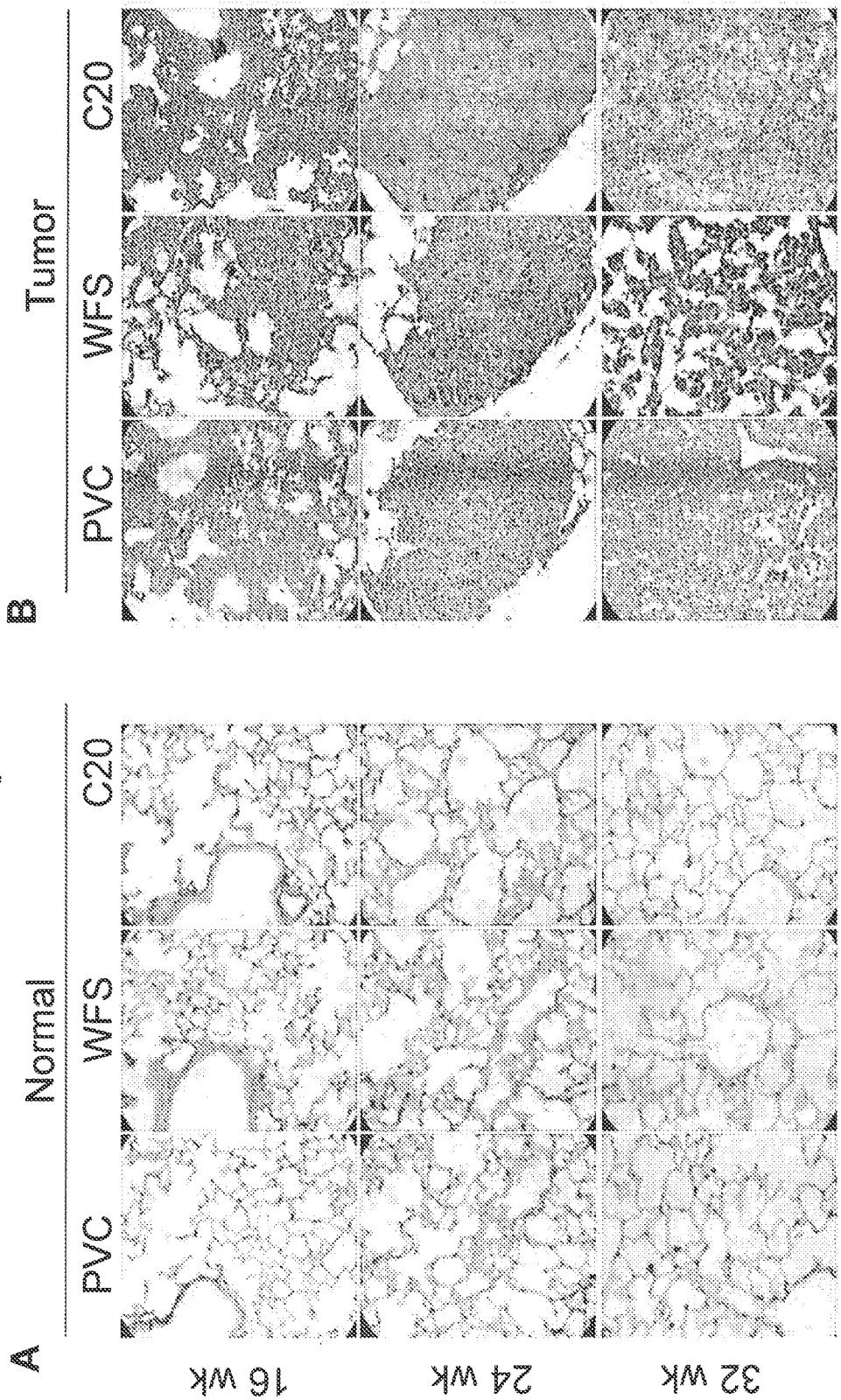
FIG. 3 shows time course of BARD1 isoform expression in experimental mouse model of induced lung cancer. (A) BARD1 expression in morphologically normal lung tissue (Normal) in urethane treated animals. BARD1 PVC and WFS epitopes were detected in some type II pneumocyte, but not in type I pneumocytes at 16 weeks (wk). All epitopes were expressed in type II and type I pneumocytes at 24 weeks and 32 weeks, and expression was upregulated from 24 weeks to 32 weeks. C20 staining was inversed to the others: strong staining at 16 weeks, week staining at 24 weeks, and almost negative at 32 weeks. (B) BARD1 expression in tumours. In tumour regions, BARD1 PVC and specifically WFS expression were upregulated from 16 to 32 weeks, while C20 expression was down-regulated from 16 to 32 weeks. (C-D) Expression pattern of BARD1 epitopes in normal (C) and tumour (D) tissues of three mice is summarized. The staining scores, percentage of positive cells, are indicated (0 indicates negative staining, 1 to 4 indicate increasing intensities and numbers of cells with positive staining).
Figure 3:
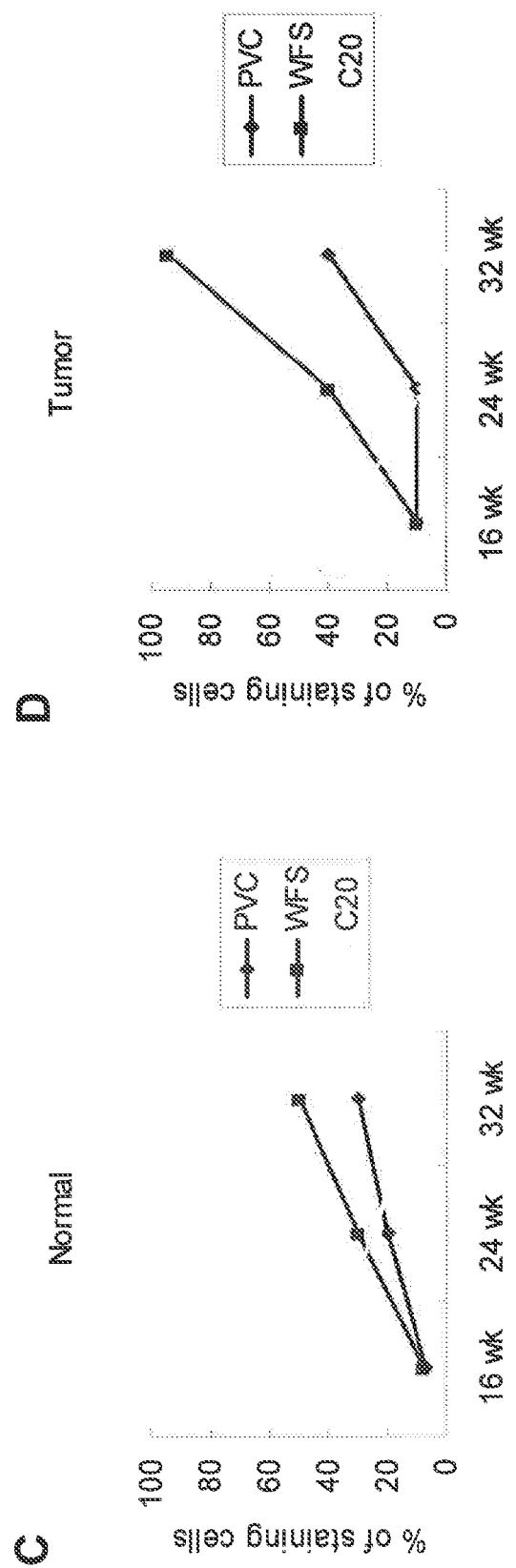

Alternative splicing is a frequently observed phenomenon in lung cancer, and has been demonstrated for a number of regulatory proteins. Splicing isoforms can be translated into aberrant protein isoforms with antagonistic functions. This has been demonstrated for two BARD1 splice variants, BARD1β and BARD1δ, which act antagonistically to FL BARD1 functions by stabilizing Aurora B and on ERα, respectively. Thus, BARD1 isoform expression in NSCLC might not merely be a bystander, but may be a driver of tumorigenesis. Indeed, the expression of epitopes mapping to exons 3 and 4, recognized by antibodies PVC and WFS, respectively, is increased in aggressive stages of lung tumours in mouse model of induced lung cancer (FIG. 3).

All lung tumour and peri-tumour tissue samples express also isoforms found in gynaecological cancers; specifically isoform δ. BARD1 isoform δ binds and stabilizes ERα, opposing the function of the BRCA1-BARD1 heterodimer. Since ERα is also expressed in all samples, BARD1 isoforms might be upregulated by estrogen and involved in estrogen signaling in lung cancer. Thus, several BARD1 isoforms seem to be associated with carcinogenesis.

As cancer cells need BARD1 or BARD1 isoforms to proliferate, BARD1 isoform expression in NSCLC and colorectal cancer is not merely a bystander, but may be a driver of tumorigenesis. Especially isoforms that express epitopes mapping to exons 3 and 4 seem to be correlated with short survival in both NSCLC and colorectal cancer. These epitopes were up regulated in invasive tumours in the mouse lung cancer model. The BARD1 isoforms expressed in NSCLC and colorectal cancer are derived from alternative splicing. For example the splicing isoforms can be translated into aberrant protein isoforms with antagonistic functions.

All lung tumour samples and peri-tumour tissue samples express ERα and isoform δ. However, there was no ERα mRNA expression in the series of colorectal cancer cases, and no differences were found between BARD1 isoforms expression and gender.

Interestingly, however, high frequency of N19 positive staining was significantly associated with female sex in colorectal cancer (P=0.014), and this finding is in line with expression of BARD1 N-terminal epitope correlated with female sex in NSCLC (the statistical significant was marginal, P=0.051). In NSCLC, high mRNA level expression of BARD1 isoforms γ, ε, and η were observed in female, while isoforms β and κ were over expressed in males. Isoforms γ and ε expression could be detected by BARD1 N19, while isoforms β, κ and η could not. Thus, protein level and mRNA level of BARD1 isoforms expression were compatible, suggesting that gender-specific BARD1 isoforms are expressed in these cancers.

BARD1 isoforms showed a different pattern of expression in tumour tissues versus peri-tumour tissues in NSCLC and colorectal cancer. In NSCLC, all isoforms, with the exception of isoform π, were expressed in peri-tumour tissue and only slightly increased in the tumour tissues, but less or no expression of any form of BARD1 was observed in control tissues obtained from benign lung disease. On the contrary, in colorectal cancer, BARD1 isoforms were more frequently expressed in tumour tissues, but not or less expressed in peri-tumour tissues. This result might be explained by diverse modulation of alternative splicing according to different cell type, in response to external stimuli or certain pathological conditions and/or the difference of ERα expression between lung and colorectal tissues.

The positive staining obtained with either PVC antibody or WFS antibody or with both of them is correlated with reduced survival of NSCLC patients. However, four antibodies positive staining pattern was significantly associated with longer survival in colorectal cancer, as well as the case for N19 positive staining; while PVC and WFS positive staining pattern was strongly correlated with shorter survival but not their positive staining individual. In fact, different expression patterns not only reflect expression of different BARD1 isoforms but also isoforms combination. According to the correlation of different epitopes of BARD1 expression, several BARD1 isoforms seem to be observed: N-terminally and C-terminally truncated form and internally deleted forms in both NSCLC and colorectal cancer, as well as additional form of loss of N-terminus in colorectal cancer. The expression pattern for four antibodies positive staining does not indicate expression of isoform π, but might reflect simultaneous expression of different isoforms of BARD1.

In fact, BARD1 isoform π expression is consistent with the epitopes recognized by PVC and WFS, a combination of epitopes not found in any other isoform. Indeed, PVC and WFS staining is cytoplasmic. Expression of PVC and WFS is clearly linked with poor prognosis in both NSCLC and colorectal cancer, PVC and WFS staining also correlated with cancer progression in the mouse lung cancer model.

Strong expression of PVC and WFS reactive epitopes, coupled with weak expression of N-terminal and C-terminal epitopes might indicate that these epitopes are blocked by steric configuration and/or protein-protein interactions. Posttranscriptional regulation or differential protein stability of FL BARD1 versus BARD1 isoforms might also account explain the absence of FL BARD1 on the protein level, while it is present on the mRNA level.

The Applicants demonstrated that BARD1 isoforms expression was common in NSCLC and colorectal cancer. Expression of these isoforms were significant associated with prognosis in NSCLC and colorectal cancer, either poor or better prognosis, and strongly suggest that BARD1 isoforms are involved in tumorigenesis, progression, and lethality. Therefore, BARD1 and isoforms thereof could be a promising diagnostic and prognostic markers, not only to identify individuals with poor prognostic potential for more aggressive treatment, but also point to a new direction for searching effective molecular targeted therapies. For example BARD1 isoforms, such as κ and π, could be targets for new strategies for lung and colorectal cancer treatment.

Detecting specific isoforms κ and π is helpful for identification of subjects with the highest risk of dying of NSCLC and colorectal cancer before and/or after potentially curative surgical treatment, since it is a critical step in selecting subjects for subsequent treatment with adjuvant chemotherapy.

The present invention provides a method for detecting the presence of a BARD1 isoform specific to lung cancer and colorectal cancer in a biological sample obtained from a subject comprising the step of detecting in said sample at least one of the BARD1 isoforms specific to lung cancer and colorectal cancer selected from the group comprising
    isoform π comprising SEQ ID NO: 1, a biologically active fragment thereof, or a sequence having at least 95% homology to SEQ ID NO: 1, and
    isoform κ comprising SEQ ID NO:2, a biologically active fragment thereof, or a sequence having at least 95% homology to SEQ ID NO:2,
    wherein the presence of said BARD1 isoforms specific to lung cancer and colorectal cancer in a sample from said subject is an indication that said subject is afflicted with lung cancer and/or colorectal cancer, has an increased risk of lung cancer and/or colorectal cancer, and/or has a risk of recurrence after a treatment for lung cancer and/or colorectal cancer.

Preferably the step of detecting comprises detecting both BARD1 isoform π comprising SEQ ID NO: 1, a biologically active fragment thereof, or a sequence having at least 95% homology to SEQ ID NO: 1, and BARD1 isoform κ comprising SEQ ID NO:2, a biologically active fragment thereof, or a sequence having at least 95% homology to SEQ ID NO:2, Also preferably the method of the invention comprises the step of detecting in said biological sample BARD1 isoform π consisting of SEQ ID NO: 1 and BARD1 isoform κ consisting of SEQ ID NO:2.

The method of the invention further comprises detecting in said biological sample at least one of the BARD1 isoforms selected from the group comprising
    isoform π' comprising SEQ ID NO:105, a biologically active fragment thereof, or a sequence having at least 95% homology to SEQ ID NO:105,
    isoform β comprising SEQ ID NO:5, a biologically active fragment thereof, or a sequence having at least 95% homology to SEQ ID NO:5,
    isoform δ comprising SEQ ID NO:6, a biologically active fragment thereof, or a sequence having at least 95% homology to SEQ ID NO:6, and
    isoform γ comprising SEQ ID NO:7, a biologically active fragment thereof, or a sequence having at least 95% homology to SEQ ID NO:7,
    isoform β' comprising SEQ ID NO:106, a biologically active fragment thereof, or a sequence having at least 95% homology to SEQ ID NO:106, Preferably the method of the invention further comprises detecting in said biological sample at least one of the BARD1 isoforms selected from the group comprising
    isoform π' comprising SEQ ID NO:105, a biologically active fragment thereof, or a sequence having at least 95% homology to SEQ ID NO:105,
    isoform β comprising SEQ ID NO:5, a biologically active fragment thereof, or a sequence having at least 95% homology to SEQ ID NO:5,
    isoform β' comprising SEQ ID NO:106, a biologically active fragment thereof, or a sequence having at least 95% homology to SEQ ID NO:106, Also preferably the method of the invention comprises the step of detecting in said biological sample BARD1 isoform π consisting of SEQ ID NO: 1, BARD1 isoform κ consisting of SEQ ID NO:2 and BARD1 isoform β consisting of SEQ ID NO:5.

In the context of the present invention "biologically active fragment" refers to regions of the BARD1 isoforms of the invention, which are necessary for normal function, for example, antagonistic functions of BARD1 isoforms. Biologically active fragments include polypeptides comprising amino acid sequences sufficiently homologous to or derived from the amino acid sequences of SEQ ID NOs: 1 to 7, 105 to 106, which include fewer amino acids than the full-length BARD1 isoforms, and exhibit at least one antagonistic activity. Typically, biologically active fragments comprise a domain or motif with at least one antagonistic activity. A biologically active fragment of BARD1 isoforms of the invention can be a polypeptide that is, for example, 10, 25, 50, 100 or more amino acid residues in length. Moreover, other biologically active fragments, in which other regions are deleted, can be prepared by recombinant techniques and evaluated for one or more of the functional activities of a native BARD1 isoforms of the invention.

For example one biological active fragment of isoform π can consist in SEQ ID NO:3, one biological active fragment of isoform κ can consist in SEQ ID NO:4 and one biological active fragment of isoform β can consist in SEQ ID NO:4.

In a further embodiment, BARD1 isoforms of the invention is a polypeptide that comprises an amino acid sequence having at least 70%, 80%, 90%, 95% or 99%, preferably 95% homology to the amino acid sequence comprising SEQ ID NOs: 1 to 7, 105 to 106 and retains the activity of BARD1 isoforms comprising SEQ ID NOs: 1 to 7, 105 to 106.

To determine the percent of homology of two amino acid sequences, the sequences are aligned for optimal comparison purposes (e.g., gaps can be introduced in the sequence of a first amino acid for optimal alignment with a second amino acid sequence). The amino acid residues at corresponding amino acid positions are then compared. When a position in the first sequence is occupied by the same amino acid residue as the corresponding position in the second sequence, then the molecules are homologous at that position. The alignment and the percent homology can be determined using any suitable software program known in the art, for example those described in CURRENT PROTOCOLS IN MOLECULAR BIOLOGY (F. M. Ausubel et al. (eds) 1987, Supplement 30, section 7.7.18). Preferred programs include the GCG Pileup program, FASTA (Pearson et al. (1988) Proc. Natl, Acad. Sci USA 85:2444-2448), and BLAST (BLAST Manual, Altschul et al., Natl. Cent. Biotechnol. Inf., Natl Lib. Med. (NCIB NLM NIH), Bethesda, Md., and Altschul et al., (1997) NAR 25:3389-3402). Another preferred alignment program is ALIGN Plus (Scientific and Educational Software, PA), preferably using default parameters. Another sequence software program that finds use is the TFASTA Data Searching Program available in the Sequence Software Package Version 6.0 (Genetics Computer Group, University of Wisconsin, Madison, Wis.).

Fragments are sequences sharing at least 40% amino acids in length with the respective sequence of the BARD1 isoforms of the present invention. These sequences can be used as long as they exhibit the same biological properties as the native sequence from which they derive, for example antagonistic activity. Preferably these sequences share more than 70%, preferably more than 80%, in particular more than 90% and the most preferably 95% amino acids in length with the respective sequence from which it derives. These fragments can be prepared by a variety of methods and techniques known in the art such as for example chemical synthesis.

The present invention also encompasses variants of BARD1 isoforms. A variant is a peptide or a polypeptide having an amino acid sequence that differs to some extent from a native sequence peptide or polypeptide, which is an amino acid sequence that varies from the native sequence by conservative amino acid substitutions, whereby one or more amino acids are substituted by another with same characteristics and conformational roles. The amino acid sequence variants possess substitutions, deletions, side-chain modifications and/or insertions at certain positions within the amino acid sequence of the native amino acid sequence. Conservative amino acid substitutions are herein defined as exchanges within one of the following five groups:

I. Small aliphatic, nonpolar or slightly polar residues: Ala, Ser, Thr, Pro, Gly II. Polar, positively charged residues: His, Arg, Lys III. Polar, negatively charged residues: and their amides: Asp, Asn, Glu, Gln IV. Large, aromatic residues: Phe, Tyr, Trp V. Large, aliphatic, nonpolar residues: Met, Leu, Ile, Val, Cys.

It is to be understood that some non-conventional amino acids may also be suitable replacements for the naturally occurring amino acids. For example Lys residues may be substituted by ornithine, homoarginine, nor-Lys, N-methyl-Lys, N,N-dimethyl-Lys and N,N,N-trimethyl-Lys. Lys residues can also be replaced with synthetic basic amino acids including, but not limited to, N-1-(2-pyrazolinyl)-Arg, 2-(4-piperinyl)-Gly, 2-(4-piperinyl)-Ala, 2-[3-(2S) pyrrolininyl]-Gly and 2-[3-(2S) pyrrolininyl]-Ala. Tyr residues may be substituted with 4-methoxy tyrosine (MeY), meta-Tyr, ortho-Tyr, nor-Tyr, 1251-Tyr, mono-halo-Tyr, di-halo-Tyr, O-sulpho-Tyr, O-phospho-Tyr, and nitro-Tyr.

Tyr residues may also be substituted with the 3-hydroxyl or 2-hydroxylisomers (meta-Tyr or ortho-Tyr, respectively) and corresponding O-sulpho- and O-phospho derivatives. Tyr residues can also be replaced with synthetic hydroxyl containing amino acids including, but not limited to 4-hydroxymethyl-Phe, 4-hydroxyphenyl-Gly, 2,6-dimethyl-Tyr and 5-amino-Tyr. Aliphatic amino acids may be substituted by synthetic derivatives bearing non-natural aliphatic branched or linear side chains CnH2n+2 where n is a number from 1 up to and including 8. Examples of suitable conservative substitutions by non-conventional amino acids are given in WO 02/064740.

Insertions encompass the addition of one or more naturally occurring or non conventional amino acid residues. Deletion encompasses the deletion of one or more amino acid residues.

Furthermore, since an inherent problem with native peptides (in L-form) is the degradation by natural proteases, the physiological active protein of the invention may be prepared in order to include D-forms and/or "retro-inverso isomers" of the peptide. Preferably, retro-inverso isomers of short parts, variants or combinations of the physiological active protein of the invention are prepared. Retro-inverso peptides are prepared for peptides of known sequence as described for example in Sela and Zisman, in a review published in FASEB J. 1997 May; 11(6):449-56. By "retro-inverso isomer" is meant an isomer of a linear peptide in which the direction of the sequence is reversed and the chirality of each amino acid residue is inverted; thus, there can be no end-group complementarity.

The invention also includes analogs in which one or more peptide bonds have been replaced with an alternative type of covalent bond (a "peptide mimetic") which is not susceptible to cleavage by peptidases. Where proteolytic degradation of the peptides following injection into the subject is a problem, replacement of a particularly sensitive peptide bond with a noncleavable peptide mimetic will make the resulting peptide more stable and thus more useful as an active substance. Such mimetics, and methods of incorporating them into peptides, are well known in the art.

Preferably the biological sample is selected from the group comprising a biopsy sample, a histology sample, lung liquids, frozen tissue sample, tumor tissue sample, feces sample, cerebrospinal fluid (CSF), circulating tumour cells (CTC) and blood sample; and preferably the subject is a human. The most preferably the biological sample is serum derived from blood sample obtained from a subject.

Detecting the presence of BARD1 isoforms of the present invention can be carried out by conventional methods such as protein immunostaining, protein immunoprecipitation, immunoelectrophoresis, immunoblotting, BCA protein assay, Western blot, spectrophotometry. The presence of BARD1 isoforms can be also detected via the presence of their corresponding mRNA by conventional methods such as Northern blot, nuclease protection assays (NPA), in situ hybridization, and reverse transcription-polymerase chain reaction (RT-PCR). Preferably the expression of BARD1 isoform-specific RNA is detected in circulating tumour cells (CTC).

In an embodiment of the present invention, the presence of BARD1 isoforms is detected by using antibodies specific to BARD1 isoforms of the invention. Preferably said antibodies are polyclonal or monoclonal antibodies or fragments thereof that specifically bind to at least one of the BARD1 isoforms comprising amino acid sequences selected from the group comprising SEQ ID NOs: 1-7, 105-106, biologically active fragments thereof, or sequences having at least 95% homology to SEQ ID NOs: 1-7, 105-106. Also preferably said antibodies are a combination of antibodies or fragments thereof that specifically bind to different epitopes of at least one of the BARD1 isoforms comprising amino acid sequences selected from the group comprising SEQ ID NOs: 1-7, 105-106, biologically active fragments thereof, or sequences having at least 95% homology to SEQ ID NOs: 1-7, 105-106. Preferably said epitopes are exons 3 and 4.

Preferably said polyclonal or monoclonal antibodies or said combination of antibodies specifically bind to at least one of the BARD1 isoforms comprising amino acid sequences selected from the group comprising SEQ ID NOs: 1 and 2, biologically active fragments thereof, or sequences having at least 95% homology to SEQ ID NOs: 1-2.

For example, antibodies which allow detection of BARD1 isoforms of the invention are the following:

N19, C20 and H300 (Santa Cruz Biotechnology, Santa Cruz, Calif.),

PVC and WSF (begin of exon 4) were generated and applied as described previously (Irminger-Finger I et al., Mol Cell 8:1255-66, 2001; Feki A et al., Oncogene 24:3726-36, 2005; Hayami R et al., Cancer Res 65:6-10, 2005; Li L et al., Int J Biochem Cell Biol 39:1659-72, 2007; Redente E F et al., Anticancer Res 29:5095-101, 2009; Fabbro M et al., J Biol Chem 277:21315-24, 2002), BL (Bethy Laboratories), JH2 and JH3 (Gautier et al. Cancer Research, 2000), PGP (Ryser et al., Cancer Research, 2000), ELS and KPD generated by Applicants MIQ (Irminger-Finger et al., JCB 1998)

The detection can be carried out by immunohistochemistry and is summarized in Table 1:

BARD1 isoform π should be positive for either N19 (or PVC, or MIQ) plus either BL (or WFS) and negative for JH2. In order to distinguish isoform π from π' (pi-d-2), this can only be done by size on Western blots.

BARD1 isoform κ should be positive for BL (or WFS) and negative for N19 (or PVC, or MIQ).

BARD1 isoform β should be positive for PGP, and either WFS or BL. In order to distinguish isoform β from β' (beta-d-5), isoform β is positive for ELS.

BARD1 isoform δ should be positive for N19 and negative for either PVC (or MIQ) and negative for BL (or WFS).

BARD1 isoform γ should be positive for N19 and either PVC (or MIQ), but negative for C20 (or KPD).

| Ab Isoform | MW(kD) | H300 | PGP | N19 | PVC | MIQ | WFS | BL | JH2 | ELS | JH3 | KPD | C20 |
|---|---|---|---|---|---|---|---|---|---|---|---|---|---|
| Exon(s) | | 1-3, 4 half | 1 alt | 1 | 3 | 3 | 4start | 4mid | 4end | 5 | 7 | 11mid | 11end |
| FL BARD1 | 95 | H300 | | N19 | PVC | MIQ | WFS | BL | JH2 | ELS | JH3 | KPD | C20 |
| alpha | 85 | H300 | | N19 | PVC | MIQ | WFS | BL | JH2 | ELS | JH3 | KPD | C20 |
| beta | 75 | H300 | PGP | — | — | — | WFS | BL | JH2 | ELS | JH3 | KPD | C20 |
| beta-D-5 | 72 | H300 | PGP | — | — | — | WFS | BL | JH2 | — | JH3 | KPD | C20 |
| kappa | 70 | H300 | | — | — | — | WFS | BL | JH2 | ELS | JH3 | KPD | C20 |
| pi | 65 | H300 | | N19 | PVC | MIQ | WFS | BL | — | ELS | JH3 | KPD | C20 |
| pi-D-2 | 62 | H300 | | N19 | PVC | MIQ | | | | ELS | JH3 | KPD | C20 |
| gama | 39 | — | | N19 | PVC | MIQ | — | — | — | — | — | — | — |
| omega | 38 | — | | — | — | — | — | — | — | ELS | JH3 | KPD | C20 |
| phi | 37 | H300 | | N19 | — | — | — | — | — | — | JH3 | KPD | C20 |
| delta | 35 | ?H300 | | N19 | — | — | — | — | — | — | JH3 | KPD | C20 |
| epsilon | 30 | H300 | | N19 | PVC | MIQ | — | — | — | — | — | KPD | C20 |
| eta | 28 | — | PGP | — | — | — | — | — | — | — | — | KPD | C20 |

Beta-D-5 is alternative name of isoform β' and pi-D-5 is alternative name for isoform π'

In another embodiment of the present invention, the presence of said BARD1 isoforms is detected by detecting the level (expression) of mRNA that encodes at least one of the BARD1 isoforms comprising amino acid sequences selected from the group comprising SEQ ID NOs: 1-7, 105-106, biologically active fragments thereof, or sequences having at least 95% homology to SEQ ID NOs: 1-7, 105-106. Preferably said mRNA encodes at least one of the BARD1 isoforms comprising amino acid sequences selected from the group comprising SEQ ID NOs: 1 and 2, biologically active fragments thereof, or a sequence having at least 95% homology SEQ ID NOs: 1-2. The expression of said mRNA is preferably carried out in vitro in circulating tumour cells (CTC) obtained from a subject.

In a further embodiment of the present invention, the presence of said BARD1 isoforms is detected by detecting the presence of autoimmune antibodies specific to BARD1 isoforms of the present invention in the blood sample obtained from the subject, preferably in serum. Preferably autoimmune antibodies are antibodies specific to BARD1 isoforms π and κ.

In the context of the present invention "autoimmune antibody" or "autoantibody" refers to a naturally occurring antibody directed to BARD1 isoforms of the invention, which the immune system of a subject recognizes as foreign proteins even though these BARD1 isoforms are actually originated in said subject. Thus these BARD1 isoforms elicit an immune response. Preferably said BARD1 isoforms are isoforms π and κ.

The autoimmune antibodies can be detected by conventional immunoassays well known in the art, for example different ELISA techniques, (either with antibody fixed on a plate surface or with the antigen fixed on the plate surface to capture the antibodies) radioimmunoassays and the like (see Immunoassay, E. Diamandis and T. Christopoulus, Academic Press, Inc., San Diego, Calif. 1996). Immunoassays for the detection of antibodies having a particular immunological specificity generally require the use of a reagent (antigen) that exhibits specific immunological reactivity with the antibody under test. Depending on the format of the assay this antigen may be immobilized on a solid support. A sample to be tested for the presence of the antibody (for example a blood sample) is brought into contact with the antigen and if antibodies of the required immunological, specificity are present in the sample they will immunologically react with the antigen, to form antibody-antigen complexes which may then be detected or quantitatively measured.

Thus according to an embodiment of the present invention, presence of BARD1 isoforms is detected by detecting the presence of autoimmune antibodies specific to said BARD1 isoforms in the blood sample obtained from the subject, wherein at least one antigen (peptide), preferably at least four antigens (peptides), selected from the group comprising SEQ ID NOs: 13-80 are used for detecting said autoimmune antibodies specific to said BARD1 isoforms. Said BARD1 isoforms are selected from the group comprising isoforms α, β, β', η, γ, ε, φ, δ, θ, π, π' and κ. Preferably said BARD1 isoforms are selected from the group comprising isoforms β, β' δ, γ, π, π' and κ. More preferably said BARD1 isoforms are selected from the group comprising isoforms β, π and κ. The most preferably said BARD1 isoforms are selected from the group comprising isoforms π and κ. The detection of autoimmune antibodies is preferably carried out in vitro on a blood sample obtained from a subject, preferably in serum.

More preferably, BARD1 isoforms are isoforms π and κ specific to lung cancer and colorectal cancer and the antigens are selected from the group comprising SEQ ID NOs: 16, 17, 18, 23, 59-67, 68, 69, 74, 75, 76-80. Most preferably the antigens are selected from the group comprising SEQ ID NOs: 16, 17, 18, 23, 68, 69, 74 and 75.

In an embodiment, the present invention provides peptide selected from the group comprising SEQ ID NOs: 13 to 80 for use in a method for detecting the presence of BARD1 isoforms of the invention.

Applicants have also discovered that the antigens selected from the group comprising SEQ ID NOs: 13-80 can also be used for detecting other cancers selected among breast cancer, ovarian cancer, prostate cancer, neuroblastoma and leukaemia, through detection of the presence of autoimmune antibodies specific to BARD1 isoforms selected from the group comprising isoforms α, β, β', η, γ, ε, φ, δ, θ, π, π' and κ. For example the antigens selected from the group comprising SEQ ID NOs: 13, 14, 15, 23, 59-67, 69, 70, 75-80 can be useful for detecting breast cancer, ovarian cancer and prostate cancer.

Thus in a further embodiment, the present invention provides peptide selected from the group comprising SEQ ID NOs: 13 to 80 for use as antigen in a method for detecting the presence of BARD1 isoforms in a biological sample obtained from a subject, wherein the presence of said BARD1 isoforms is detected by detecting the presence of autoimmune antibodies specific to said BARD1 isoforms and wherein the presence of said BARD1 isoforms in said sample is an indication that said subject is afflicted with cancer. Said BARD1 isoforms are selected from the group comprising isoforms α, β, β', η, γ, ε, φ, δ, θ, π, π' and κ.

At least one antigen should be used for detecting the presence of autoimmune antibodies specific to BARD1 isoforms. Preferably at least four antigens are used; more preferably four to ten antigens are used; the most preferably four to six antigens are used.

The antigens of the present invention can also be contacted with negative control samples (healthy control blood samples) in order to obtain a base line, which facilitates discrimination between cancer subjects and healthy subjects (see Examples—Detection of anti-BARD1 autoimmune antibodies in blood of lung cancer patients). Optionally the antigens of the present invention can also be contacted with positive control samples (confirmed cancer blood samples) in order to obtain clear positive results.

In another embodiment, a blood sample from a subject can be contacted with BARD1 isoforms of the invention, preferably isoforms π and κ or fragments thereof. Then the specific binding between autoimmune antibody and said BARD1 isoforms can be detected allowing determination of the presence or absence of lung cancer and/or colorectal cancer based on the amount of the specific binding between autoimmune antibody and said BARD1 isoforms. The detection of autoimmune antibodies is preferably carried out in vitro on a blood sample obtained from a subject, preferably in serum.

Alternatively, according to an embodiment of the present invention, the presence of BARD1 isoforms of the invention is detected by
    detecting the level of mRNA that encodes at least one of the BARD1 isoforms comprising amino acid sequences selected from the group comprising SEQ ID NOs: 1-7, 105-106, biologically active fragments thereof, or sequences having at least 95% homology to SEQ ID NOs: 1-7, 105-106, and
    detecting the presence of autoimmune antibodies specific to said BARD1 isoforms in the blood sample obtained from the subject, and wherein at least four antigens selected from the group comprising SEQ ID NOs: 13-80 are used for detecting said autoimmune antibodies specific to said BARD1 isoforms.

The present invention further provides an isolated and/or purified polypeptide comprising SEQ ID NO: 1, a biologically active fragment thereof, or a sequence having at least 95% homology to SEQ ID NO: 1 for use as a biomarker in the method of the present invention; and an isolated and/or purified polypeptide comprising SEQ ID NO:2, a biologically active fragment thereof, or a sequence having at least 95% homology to SEQ ID NO: 2 for use as a biomarker in the method of the present invention.

The present invention also provides an antibody or fragment thereof which binds to an epitope as set forth in SEQ ID NO: 143 (DTKSRNEVVTPIKGDIPSVEYLLQNGS) on BARD1 isoform π. Preferably the present invention provides an antibody or fragment thereof which binds to an epitope as set forth in SEQ ID NO: 144 (NEVVTPIKG-DIPSVEY).

The present invention further provides an antibody or fragment thereof which binds to an epitope as set forth in SEQ ID NO: 143 for use in a method for treating and/or preventing lung cancer and colorectal cancer. Preferably the present invention provides an antibody or fragment thereof which binds to an epitope as set forth in SEQ ID NO: 144 for use in a method for treating and/or preventing lung cancer and colorectal cancer The present invention also encompasses polyclonal or monoclonal antibody or fragment thereof that specifically bind to at least one of the BARD1 isoforms comprising amino acid sequences selected from the group comprising SEQ ID NOs: 1-7, 105-106, biologically active fragments thereof, or sequences having at least 95% homology to SEQ ID NOs: 1-7, 105-106, for use in a method for treating and/or preventing lung cancer and colorectal cancer, and wherein the following antibodies are excluded N19, C20, H300, PVC, WSF, BL, JH2, JH3, PGP, ELS, KPD, MIQ.

It is also encompassed by the present invention a combination of antibodies or fragments thereof that specifically bind to different epitopes of at least one of the BARD1 isoforms comprising amino acid sequences selected from the group comprising SEQ ID NOs: 1-7, 105-106, biologically active fragments thereof, or sequences having at least 95% homology to SEQ ID NOs: 1-7, 105-106 for use in a method for treating and/or preventing lung cancer and colorectal cancer, and wherein the following antibodies are excluded: N19, C20, H300, PVC, WSF, BL, JH2, JH3, PGP, ELS, KPD, MIQ.

The antibody of the present invention can be also used for detecting the BARD1 isoforms comprising amino acid sequences selected from the group comprising SEQ ID NOs: 1-7, 105-106, biologically active fragment thereof, or sequence having at least 95% homology to SEQ ID NOs: 1-7, 105-106 in tissue samples of a subject, body fluids of a subject, or circulating cells in the blood of a subject.

Preferably said polyclonal or monoclonal antibodies or said combination of antibodies specifically bind to at least one of the BARD1 isoforms comprising amino acid sequences selected from the group comprising SEQ ID NOs: 1 and 2, biologically active fragments thereof, or sequences having at least 95% homology SEQ ID NOs: 1-2.

As used herein, the term "antibody" refers to an immunoglobulin molecule having a specific structure, that interacts (i.e., binds) only with the antigen that was used for synthesizing the antibody (for example BARD1 isoforms of the invention) or with an antigen closely related thereto. Furthermore, an antibody can be a fragment of an antibody or a modified antibody, so long as it binds to one or more of the proteins encoded by the marker genes. For instance, the antibody fragment can be Fab, F(ab')2, Fv, or single chain Fv (scFv), in which Fv fragments from H and L chains are ligated by an appropriate linker (Huston J. S. et al., (1988) Proc. Natl. Acad. Sci. U.S.A. 85:5879-83.). More specifically, an antibody fragment can be generated by treating an antibody with an enzyme, including papain or pepsin. Alternatively, a gene encoding the antibody fragment can be constructed, inserted into an expression vector, and expressed in an appropriate host cell (see, for example, Co M. S. et al., (1994) J. Immunol. 152:2968-76; Better M. and Horwitz A. H. (1989) Methods Enzymol. 178:476-96.; Pluckthun A. and Skerra A. (1989) Methods Enzymol. 178:497-515.; Lamoyi E. (1986) Methods Enzymol. 121: 652-63.; Rousseaux J. et al, (1986) Methods Enzymol. 121:663-9.; Bird R. E. and Walker B. W. (1991) Trends Biotechnol. 9:132-7.).

An antibody can be modified by conjugation with a variety of molecules, for example, polyethylene glycol (PEG). The modified antibody can be obtained by chemically modifying an antibody. Such modification methods are conventional in the field.

Alternatively, an antibody can comprise a chimeric antibody having a variable region from a nonhuman antibody and a constant region from a human antibody, or a humanized antibody, comprising a complementarity determining region (CDR) from a nonhuman antibody, a frame work region (FR) and a constant region from a human antibody. Such antibodies can be prepared by using known technologies. Humanization can be performed by substituting rodent CDRs or CDR sequences for the corresponding sequences of a human antibody {see, e.g., Verhoeyen et al, (1988) Science 239:1534-6). Accordingly, such humanized antibodies are chimeric antibodies, wherein substantially less than an intact human variable domain has been substituted by the corresponding sequence from a non-human species. Fully human antibodies comprising human variable regions in addition to human framework and constant regions can also be used. Such antibodies can be produced using various techniques known in the art. For example in vitro methods involve use of recombinant libraries of human antibody fragments displayed on bacteriophage (e.g., Hoogenboom & Winter, (1992) J. Mol. Biol. 227:381-8). Similarly, human antibodies can be made by introducing of human immunoglobulin loci into transgenic animals, e.g., mice in which the endogenous immunoglobulin genes have been partially or completely inactivated. This approach is described, e.g., in U.S. Pat. Nos. 6,150,584; 5,545,807; 5,545,806; 5,569,825; 5,625,126; 5,633,425; 5,661,016. Such antibodies can be prepared by using known technologies.

The present invention also provides a recombinant siRNA molecule that binds to a single-stranded or double stranded RNA molecule, wherein said single-stranded or double stranded RNA molecule comprises an mRNA that encodes at least one of the BARD1 isoforms comprising amino acid sequences selected from the group comprising SEQ ID NOs: 1-7, 105-106, biologically active fragments thereof, or sequence having at least 95% homology to SEQ ID NOs: 1-7, 105-106 and whereby the expression of said BARD1 isoforms are inhibited, for use in a method for treating and/or preventing lung cancer and colorectal cancer.

Preferably said mRNA encodes at least one of the BARD1 isoforms comprising amino acid sequences selected from the group comprising SEQ ID NOs: 1 and 2, biologically active fragments thereof, or sequences having at least 95% homology to SEQ ID NOs: 1-2.

In the context of the present invention, the siRNA (RNA interferent or small interfering RNA) inhibits or reduces the expression of BARD1 isoforms. Preferably said isoforms are π, π', κ, β, β', δ, and γ; more preferably π, κ, β and the most preferably π and κ. Herein, the term "siRNA" refers to a double stranded RNA molecule which prevents translation of a target mRNA. Usually the siRNA comprises a sense nucleic acid sequence and an anti-sense nucleic acid sequence against expression of one or more of the BARD1 isoforms comprising amino acids sequences selected from the group comprising SEQ ID NOs: 1-7, 105-106, biologically active fragments thereof, or sequences having at least 95% homology to SEQ ID NOs: 1-7, 105-106.

In general, siRNA can be isolated. An "isolated" siRNA is one that is removed from its original environment. For example, a siRNA is considered to be isolated if it is cloned into a vector that is not a part of the natural environment.

The siRNA can be constructed fully synthetically and consisting of two complementary single stranded RNA or biosynthetically. The siRNA is constructed such that a single transcript has both the sense and complementary antisense sequences from the target gene, (e.g. a single hairpin RNA or shRNA). Standard techniques for introducing siRNA into the cell can be used, including those in which DNA is a template from which RNA is transcribed.

Usually, an siRNA that binds to a single-stranded RNA molecule, wherein said single-stranded RNA molecule comprises an mRNA that encodes at least one of the BARD1 isoforms comprising amino acids sequences selected from the group comprising SEQ ID NOs: 1-7, 105-106, biologically active fragments thereof, or sequences having at least 95% homology to SEQ ID NOs: 1-7, 105-106, by associating with the normally single-stranded mRNA transcript, thereby interfering with translation and thus, expression of the BARD1 isoforms. Thus, siRNA molecules of the invention can be defined by their ability to hybridize specifically to mRNA or cDNA that encodes at least one of the BARD1 isoforms comprising amino acids sequences selected from the group comprising SEQ ID NOs: 1-7, 105-106, biologically active fragments thereof, or sequences having at least 95% homology to SEQ ID NOs: 1-7, 105-106.

In the context of the present invention, an siRNA is preferably less than 500, preferably less than 200, more preferably less than 100, even more preferably less than 50, or most preferably less than 25 nucleotides in length. More preferably an siRNA is about 19 to about 25 nucleotides in length. In order to enhance the inhibition activity of the siRNA, one or more uridine ("u") nucleotides can be added to 3' end of the antisense strand of the target sequence. The number of "u's" to be added is at least 2, generally 2 to 10, preferably 2 to 5. The added "u's" form a single strand at the 3' end of the antisense strand of the siRNA.

A siRNA of the present invention can be directly introduced into the cells in a form that is capable of binding to the mRNA transcripts. In these embodiments, the siRNA molecules of the invention are typically modified as know in the art. Other modifications are also possible, for example, cholesterol-conjugated siRNAs have shown improved pharmacological properties. Song, et al, Nature Med. 9:347-51 (2003). Alternatively, a DNA encoding the siRNA can be carried in a vector.

Several useful siRNA have been identified. For example siRNA in exon 9 (please refer to FIG. 1A and FIG. 4E) is efficient and lead to proliferation arrest. In another example, using siRNA within exon 4 is important for BARD1 isoform π (see FIG. 17). Some useful siRNA are:

```
                                       (SEQ ID NO. 107)
K34:  CATTCTGAGAGAGCCTGTG (SEQ ID NO. 108)
K423: GTGCTCAGCAAGACTCATA (SEQ ID NO. 109)
K401: AAGTCTCTTTACCATTGGCTG
```

```
                                       (SEQ ID NO. 110)
K78:  AAGTGTATGCTTGGGATTCTC
```

The present invention further provides a modulator of the biological activity of the BARD1 isoforms comprising amino acid sequences selected from the group comprising SEQ ID NOs: 1-7, 105-106, biologically active fragments thereof, or sequences having at least 95% homology to SEQ ID NOs: 1-7, 105-106, for use in a method for treating and/or preventing lung cancer and colorectal cancer. Preferably said BARD1 isoforms comprise amino acid sequences selected from the group comprising SEQ ID NOs: 1 and 2, biologically active fragments thereof, or sequences having at least 95% homology to SEQ ID NOs: 1-2.

The modulator of the biological activity of the BARD1 isoforms can be a competitor. Preferably said competitor is a compound able to disturb interaction between said BARD1 isoforms and a receptor thereof. For example, the competitor can be also an inhibitor or an antagonist. The term "inhibitor" or "antagonist" refers to molecules that inhibit the function of the protein or polypeptide by binding thereto. The competitor, such as inhibitor or antagonist, can directly inhibit the interaction between BARD1 isoforms of the invention and its natural ligand and/or receptor resulting in disturbed biochemical or biological function of the receptor. Competitive inhibition is a form of inhibition where binding of the inhibitor prevents binding of the ligand and vice versa. In competitive inhibition, the inhibitor binds to the same active site as the natural ligand, without undergoing a reaction. The ligand molecule cannot enter the active site while the inhibitor is there, and the inhibitor cannot enter the site when the ligand is there. The "biological activity or function" of a protein refers to the ability to carry out diverse cellular functions and to bind other molecules specifically and tightly.

Also in the context of the present invention, a modulator of the biological activity of the BARD1 isoforms of the invention can be preferably microRNA (miRNA) which modulates gene expression. Applicants found that BARD1 can be target of many microRNAs. The exogenous expression of specific microRNA represses BARD1 expression (see FIG. 18). More preferably in the context of the present invention, microRNAs are selected from the group comprising: hsa-mir-10a MI0000266: (SEQ ID NO. 111); hsa-mir-10b MI0000267 (SEQ ID NO. 112); hsa-mir-130a MI0000448 (SEQ ID NO. 113); hsa-mir-130b MI0000748 (SEQ ID NO. 114); hsa-mir-134 MI0000474 (SEQ ID NO. 115); hsa-mir-144 MI0000460 (SEQ ID NO. 116); hsa-mir-148a MI0000253 (SEQ ID NO. 117); hsa-mir-148b MI0000811 (SEQ ID NO. 118); hsa-mir-152 MI0000462 (SEQ ID NO. 119); hsa-mir-181a-2 MI0000269 (SEQ ID NO. 120); hsa-mir-181a-1 MI0000289 (SEQ ID NO. 121); hsa-mir-181b-1 MI0000270 (SEQ ID NO. 122); hsa-mir-181b-2 MI0000683 (SEQ ID NO. 123); hsa-mir-19a MI0000073 (SEQ ID NO. 124); hsa-mir-19b-1 MI0000074 (SEQ ID NO. 125); hsa-mir-19b-2 MI0000075 (SEQ ID NO. 126); hsa-mir-203 MI0000283 (SEQ ID NO. 127); hsa-mir-301a MI0000745 (SEQ ID NO. 128); hsa-mir-301b MI0005568 (SEQ ID NO. 129); hsa-mir-452 MI0001733 (SEQ ID NO. 130); hsa-mir-454 MI0003820 (SEQ ID NO. 131); hsa-mir-517a MI0003161 (SEQ ID NO. 132); hsa-mir-517c MI0003174 (SEQ ID NO. 133); hsa-mir-553 MI0003558 (SEQ ID NO. 134); hsa-mir-570 MI0003577 (SEQ ID NO. 135); hsa-mir-576 MI0003583 (SEQ ID NO. 136); hsa-mir-579 MI0003586 (SEQ ID NO. 137); hsa-mir- 580 MI0003587 (SEQ ID NO. 138); hsa-mir-613 MI0003626 (SEQ ID NO. 139); hsa-mir-618 MI0003632 (SEQ ID NO. 140).

Usually microRNAs are short ribonucleic acid (RNA) molecules, having at least about 22 nucleotides, preferably about 60 to about 100 nucleotides, which can bind to complementary sequences on target messenger RNA transcript (mRNAs), usually resulting in translational repression or target degradation and gene silencing.

The present invention also includes a method for discriminating lung cancer and colorectal cancer from gynecological cancers, said method comprising the step of detecting in a biological sample obtained from a subject at least one of the BARD1 isoforms specific to lung cancer and colorectal cancer selected from the group comprising isoform π comprising SEQ ID NO: 1, a biologically active fragment thereof, or a sequence having at least 95% homology to SEQ ID NO: 1, and isoform κ comprising SEQ ID NO:2, a biologically active fragment thereof, or a sequence having at least 95% homology to SEQ ID NO: 2.

wherein the presence of said BARD1 isoforms specific to lung cancer and colorectal cancer is an indication for lung cancer and/or colorectal cancer.

Another feature useful to discriminate lung cancer and colorectal cancer from gynecological cancers, is that BARD1 isoform α is absent in lung cancer and colorectal cancer. The amino acid sequence of BARD1 isoform α is known from PCT/EP2008/053881. Thus optionally, said method further comprises detecting in said sample BARD1 isoform α, a biologically active fragment thereof, or a sequence having at least 95% homology BARD1 isoform α, wherein the absence of said BARD1 isoform α is an indication that said subject is not afflicted with lung cancer and/or colorectal cancer.

Preferably, gynaecological cancers are a group of different malignancies of the female reproductive system. The most common types of gynaecologic malignancies are cervical cancer, ovarian cancer, and endometrial (uterus) cancer. There are other less common gynaecological malignancies including cancer of the vagina, cancer of the vulva, gestational trophoblastic tumours, and fallopian tube cancer. In the context of the present invention, breast cancer is also included in gynaecological cancers.

The present invention further provides a kit for detecting the presence of BARD1 isoforms specific to lung cancer and colorectal cancer in a sample obtained from a subject, comprising at least one polynucleotide primer or probe wherein said polynucleotide primer or probe is specific for a polynucleotide that encodes at least one of the BARD1 isoforms comprising amino acid sequences selected from the group comprising SEQ ID NOs: 1-7, 105-106, biologically active fragments thereof, and/or sequences having at least 95% homology to SEQ ID NOs: 1-7, 105-106, and/or combination of antibodies or fragments thereof that specifically binds to different epitopes of at least one of the BARD1 isoforms comprising amino acid sequences selected from the group comprising SEQ ID NOs: 1-7, 105-106, biologically active fragments thereof, or sequences having at least 95% homology to SEQ ID NOs: 1-7, 105-106, and/or at least one peptide selected from the group comprising SEQ ID NOs: 13 to 80.

Preferably said BARD1 isoforms comprises amino acid sequences selected from the group comprising SEQ ID NOs: 1-22, biologically active fragments thereof, or sequences having at least 95% homology to SEQ ID NO: 1-2.

Polynucleotide that encodes at least one of the BARD1 isoforms is a polynucleotide comprising nucleic acid sequences selected from the group comprising SEQ ID NO: 8 (isoform π), SEQ ID NO: 9 (isoform κ), SEQ ID NO: 10 (isoform β), SEQ ID NO: 11 (isoform δ), SEQ ID NO: 12 (isoform γ), SEQ ID NO: 141 (isoform π'), SEQ ID NO: 142 (isoform β'); preferably nucleic acid sequences selected from the group comprising SEQ ID NO: 8 and 9.

Primers, probes, and/or antibodies can be packaged together along with other necessary detection reagents in the form of a kit. For example, they can be packaged in separate containers, e.g., a nucleic acid or antibody (either bound to a solid matrix or packaged separately with reagents for binding them to the matrix), a control reagent (positive and/or negative), and/or a detectable label. Instructions (e.g., written, tape, VCR, CD-ROM, etc.) for carrying out the detection can also be included in the kit.

The present invention also encompasses vaccines and vaccination methods. For example, methods of treating or preventing lung cancer and/or colorectal cancer in a subject suffering from said cancer can involve administering to the subject a vaccine composition comprising one or more of the BARD1 isoforms comprising amino acids sequences selected from the group comprising SEQ ID NOs: 1-7, 105-106, a biologically active fragment thereof, a sequence having at least 95% homology to SEQ ID NOs: 1-7, 105-106 or an immunologically active fragment thereof, or one or more peptide (antigen) selected from the group comprising SEQ ID NO:13 to 80.

Preferably said BARD1 isoforms comprise amino acids sequences selected from the group comprising SEQ ID NOs: 1-2, a biologically active fragment thereof, a sequence having at least 95% homology to SEQ ID NOs: 1-2 and said peptide are selected from the group comprising SEQ ID NOs: 16, 17, 18, 23, 59-67, 68, 69, 74, 75, 76-80.

In the context of the present invention, an immunologically active fragment is a polypeptide that is shorter in length than the full-length naturally-occurring protein, for example one of BARD1 isoforms, yet which induces an immune response analogous to that induced by the full-length protein. For example, an immunologically active fragment should be at least 8 residues in length and capable of stimulating an immune cell, for example, a T cell or a B cell. Immune cell stimulation can be measured by detecting cell proliferation, elaboration of cytokines (e.g., IL-2), or production of an antibody. See, for example, Harlow and Lane, Using Antibodies: A Laboratory Manual, 1998, Cold Spring Harbor Laboratory Press; and Coligan, et al., Current Protocols in Immunology, 1991-2006, John Wiley & Sons.

The present invention also includes a pharmaceutical composition for the treatment or prevention of lung cancer and/or colorectal cancer in a subject suffering from said cancer, wherein said composition comprises a pharmaceutically effective amount of an antibody of the present invention.

The present invention further includes a pharmaceutical composition for the treatment or prevention of lung cancer and/or colorectal cancer in a subject suffering from said cancer, wherein said composition comprises a pharmaceutically effective amount of a siRNA of the present invention.

The present invention further encompasses a pharmaceutical composition for the treatment or prevention of lung cancer and/or colorectal cancer in a subject suffering from said cancer, wherein said composition comprises a pharmaceutically effective amount of a modulator according to the present invention. Preferably said modulator is microRNA, which modulates gene expression.

"Treatment" refers to both therapeutic treatment and prophylactic or preventative measures. Those in need of treatment include those already with the disorder, such as lung and/or colorectal cancer, as well as those in which the disorder is to be prevented. Hence, the mammal, preferably human to be treated herein may have been diagnosed as having the disorder or may be predisposed or susceptible to the disorder, such as lung and/or colorectal cancer.

"Prevention" as used herein means that the administration of the modulator(s), siRNA and/or antibodies as described in the present invention results in a reduction in the likelihood or probability that a subject at high risk for lung and/or colorectal cancer will indeed develop said cancer.

"A pharmaceutically effective amount" refers to an active ingredient (for example chemical or biological material) which, when administered to a human or animal organism induces a detectable pharmacologic and/or physiologic effect.

The respective pharmaceutically effect amount can depend on the specific subject to be treated, on the disease to be treated and on the method of administration. The treatment usually comprises a multiple administration of the pharmaceutical composition, usually in intervals of several hours, days or weeks. The pharmaceutically effective amount of a dosage unit of the active ingredient, such as antibody, siRNA or a modulator of the present invention, usually is in the range of 0.001 ng to 100 mg per kg of body weight of the subject to be treated. It is understood that the suitable dosage of an active ingredient of the present invention will be dependent upon the age, sex, health, and weight of the recipient, kind of concurrent treatment, if any and the nature of the effect desired.

For systemic administration, a therapeutically effective amount or dose can be estimated initially from in vitro assays. For example, a dose can be formulated in animal models to achieve a circulating concentration range that includes the IC50 as determined in cell culture. Such information can be used to more accurately determine useful doses in humans.

Initial doses can also be estimated from in vivo data, e.g. animal models, using techniques that are well known in the art. One ordinarily skill in the art could readily optimise administration to humans based on animal data and will, of course, depend on the subject being treated, on the subject's weight, the severity of the disorder, the manner of administration and the judgement of the prescribing physician.

"Administering", as it applies in the present invention, refers to contact of the pharmaceutical compositions to the subject, preferably a human.

The pharmaceutical composition may be dissolved or dispersed in a pharmaceutically acceptable carrier well known to those skilled in the art, for parenteral administration by, e.g., intravenous, subcutaneous or intramuscular injection or by intravenous drip infusion.

As to a pharmaceutical composition for parenteral administration, any conventional additives may be used such as excipients, adjuvants, binders, disintegrants, dispersing agents, lubricants, diluents, absorption enhancers, buffering agents, surfactants, solubilizing agents, preservatives, emulsifiers, isotonizers, stabilizers, solubilizers for injection, pH adjusting agents, etc.

Acceptable carriers, diluents and adjuvants which facilitates processing of the active compounds into preparation which can be used pharmaceutically are non-toxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl orbenzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN®, PLURONICS® or polyethylene glycol (PEG).

The form of administration of the pharmaceutical composition may be systemic or topical. For example, administration of such a pharmaceutical composition may be various parenteral routes such as subcutaneous, intravenous, intradermal, intramuscular, intraperitoneal, intranasal, transdermal, buccal routes or via an implanted device, and may also be delivered by peristaltic means.

The pharmaceutical composition comprising an active ingredient of the present invention may also be incorporated or impregnated into a bioabsorbable matrix, with the matrix being administered in the form of a suspension of matrix, a gel or a solid support. In addition the matrix may be comprised of a biopolymer.

Sustained-release preparations may be prepared. Suitable examples of sustained-release preparations include semi permeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and [gamma]ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations to be used for in vivo administration must be sterile. This is readily accomplished for example by filtration through sterile filtration membranes.

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended Claims, and all changes which come within the meaning and range of equivalency are intended to be embraced therein.

The foregoing description will be more fully understood with reference to the following Examples. Such Examples, are, however, exemplary of methods of practising the present invention and are not intended to limit the scope of the invention.

EXAMPLES

I

Patients—Lung Cancer

Tumor tissues from 100 NSCLC patients were collected at two different centres (Table 1). All patients were informed and approval obtained from the local ethics committees. Eight cases with benign lung diseases (five males and three females, ages ranging from 24 to 66 years (median age, 38 years); five cases of pulmonary emphysema, the rest pulmonary tuberculosis and carcinoid dysplasia) were used as control samples for BARD1 expression.

Follow-up records were available for 48 of 60 patients from Napoli; follow-up was from one to 69 months; two patients died during the perioperative period, and data on 10 patients were not available. Of 48 patients with follow-up records, 17 were treated with surgery only, four with chemotherapy post surgery, one with chemotherapy and radiotherapy post surgery, seven patients were treated with chemotherapy and radiotherapy, four with chemotherapy and one with radiotherapy only, and the remaining 14 were without treatment till last follow-up or death. Of these 48 patients, 35 were dead, and 13 were still alive during last follow-up period. Seventeen of 40 patients from Cagliari had follow-up records; follow-up was from five to 95 months; 11 patients were still alive at the last follow-up period (March 2010), and 6 patients died. Overall survival was calculated from the date of surgery, beginning of chemotherapy or radiotherapy, or the date of diagnosis for patients without treatment, to the last follow-up or death.

TABLE 1

| Patient Characteristics - lung cancer | | | | |
|---|---|---|---|---|
| Samples | | Napoli | Cagliari | Total |
| Cases | | 60 | 40 | 100 |
| Gender | Male | 54 | 20 | 74 |
| | Female | 6 | 20 | 26 |
| Age | Range | 34-77 | 33-77 | 33-77 |
| | Median | 63 | 60 | 62 |
| Normal (peri-tumor) | | 0 | 20 | 20 |
| Tumor | | 60 | 40 | 100 |
| Histology | Adenocarcinoma | 26 | 40 | 66 |
| | Squamous Cell Carcinoma | 21 | 0 | 21 |
| | Large Cell Carcinoma | 9 | 0 | 9 |
| | Adenosquamous Carcinoma | 4 | 0 | 4 |
| Grade | Well-differentiated | 2 | 10 | 12 |
| | Moderately differentiated | 20 | 12 | 32 |
| | Poorly differentiated | 26 | 18 | 44 |
| | Undifferentiated | 1 | 0 | 1 |
| | Unspecified | 11 | 0 | 11 |
| Stage | IA | 14 | 18 | 32 |
| | IB | 19 | 8 | 27 |
| | IIA | 1 | 5 | 6 |
| | IIB | 9 | 3 | 12 |
| | IIIA | 11 | 2 | 13 |
| | IIIB | 4 | 1 | 5 |
| | IV | 1 | 3 | 4 |
| | Unknown | 1 | 0 | 1 |

Patients Characteristics—Colorectal Cancer

Pathologic diagnoses were made by experienced pathologists based on WHO criteria and staged according to American Joint Committee on Cancer classification. All patients were informed and compliance was obtained as well as approval of the local ethical committees. A total of 168 cases with colorectal cancer containing 20 cases from Cagliari and 148 cases from Germany were examined (Table 2). Twenty cases from Cagliari including both tumor tissue and their adjacent morphologically normal tissue (peri-tumor) samples were used for reverse-transcriptase PCR detection. 148 cases with colorectal cancer from Germany were used for immunohistochemistry on tissue arrays. These 168 cases were composed of 106 colon cancers and 62 rectal cancers, they were all adenocarcinomas. The patients were 93 males and 75 females, with age at diagnosis ranging from 33 to 78 years (median age, 61 years). 21 patients had stage I disease, 34 stage II, 50 stage III, and 23 stage IV; the remaining 40 patients were of unknown stage since the primary tumor or/and the regional lymph nodes or/and distant metastasis could not be assessed. Ten patients had well differentiated (G1), 116 moderately differentiated (G2), and 38 poorly differentiated (G3) tumors; the remaining 2 patients were unspecified (GX).

The sections used for immunochemical staining were tissue microarrays with tetramerous for each case. 75 of 148 cases had follow-up records, follow-up was from one to 72 months, and remaining 73 patients had no survival data. Of these 75 patients with follow-up records, 22 were dead, 48 were lost, and five were still alive during last follow-up period.

TABLE 2

| Patient characteristics of colorectal cancer | | | | |
|---|---|---|---|---|
| Samples | | Germany | Cagliari | Total |
| Cases | | 148 | 20 | 168 |
| Gender | Male | 83 | 10 | 93 |
| | Female | 65 | 10 | 75 |
| Age | Range | 41-97 | 33-73 | 33-97 |
| | Median | 73 | 60.5 | 71 |
| Normal (peri-tumor) | | 0 | 20 | 20 |
| Tumor | | 148 | 20 | 168 |
| Histology | Adenocarcinoma | 148 | 20 | 168 |
| Grade | Well-differentiated | 10 | 0 | 10 |
| | Moderately differentiated | 105 | 12 | 117 |
| | Poorly differentiated | 32 | 6 | 38 |
| | Undifferentiated | 0 | 0 | 0 |
| | Unspecified | 1 | 2 | 3 |
| Tumor | T1 | 3 | 1 | 4 |
| | T2 | 32 | 4 | 36 |
| | T3 | 69 | 13 | 82 |
| | T4 | 42 | 2 | 44 |
| | TX | 2 | 0 | 2 |
| Node | N0 | 74 | 7 | 81 |
| | N1 | 34 | 7 | 41 |
| | N2 | 36 | 6 | 42 |
| | N3 | 1 | 0 | 1 |
| | NX | 3 | 0 | 3 |
| Metastasis | M0 | 101 | 15 | 116 |
| | M1 | 44 | 5 | 49 |
| | MX | 3 | 0 | 3 |
| Stage | I | 26 | 4 | 30 |
| | II | 38 | 3 | 41 |
| | III | 35 | 9 | 44 |
| | IV | 44 | 4 | 48 |
| | Unknown | 5 | 0 | 5 |

Immunohistochemistry

Immunohistochemistry was performed on adjacent sections with antibodies against different regions of BARD1 and against BRCA1.

Antibodies against different regions of BARD1 used, namely N19 (exon 1) (sc-7373) and C20 (exon 11) (sc-7372), were purchased from Santa Cruz (Santa Cruz Biotechnology, Santa Cruz, Calif.), PVC (exon 3) and WSF (begin of exon 4) were generated and applied as described previously (Irminger-Finger I et al., Mol Cell 8:1255-66, 2001; Feki A et al., Oncogene 24:3726-36, 2005; Hayami R et al., Cancer Res 65:6-10, 2005; Li L et al., Int J Biochem Cell Biol 39:1659-72, 2007; Redente E F et al., Anticancer Res 29:5095-101, 2009; Fabbro M et al., J Biol Chem 277:21315-24, 2002). Antibodies against BRCA1 were from Santa Cruz (D16; Santa Cruz Biotechnology, Santa Cruz, Calif.). Staining was visualized by secondary antibodies (goat antirabbit or rabbit antigoat) conjugated with HRP were applied in 1:100 dilutions at room temperature for 1 hr. DAB staining was for 2 to 15 min at room temperature. Slides were counterstained with hematoxylin before dehydration and mounting. To ascertain sensitivity and specificity, immunohistochemistry was performed omitting the primary antibodies on control sections. To quantify expression of BARD1 or BRCA1, 4 different regions were chosen for each tumor section; the percentage of positive cells and intensity of staining were combined to calculate an average score of each sample. Three persons performed this quantification independently and without any knowledge of clinical data.

For immunohistochemistry performed on mice with induced lung cancer, treated and age-matched untreated mice were sacrificed after 16, 24, and 32 weeks, and tumors dissected and analyzed by immunohistochemistry using antibodies PVC, WFS, and C20 on two control and three tumor bearing mice. Analysis and quantification was as described for human samples.

Formalin-fixed and paraffin-embedded 5 µm tissues sections were de-paraffinized in xylene and re-hydrated through descending ethanol concentrations (100% alcohol, 95% alcohol, 70% alcohol, dH2O). The sections were boiled for 5 min in a microwave for antigen retrieval, and endogenous peroxidases were blocked. Slides were incubated overnight at 4° C. in a humidifying chamber with the first antibody after BSA (bovine serum albumin) blocking of the non-specific epitopes. The primary antibodies used for BARD1 detection were N19 (sc-7373, Santa Cruz Biotechnology) (1:25 diluted), PVC (1:100 diluted), WFS (1:100 diluted), and C20 (sc-7372, Santa Cruz, Calif.) (1:20 diluted), which recognize epitopes in exons 1, 3, 4, and 11, respectively; BRCA1 antibody was C20 (sc-642, Santa Cruz Biotechnology) (1:100 diluted), recognizing BRCA1 C-terminal epitopes. Secondary antibodies (goat anti-rabbit or rabbit anti-goat) conjugated with horse radish peroxidase (HRP) were applied in 1:100 dilutions at room temperature for 1 hour. Then diaminobenzidine (DAB) staining was permitted for maximum 15 minutes at room temperature. Slides were counter-stained with hematoxylin before de-hydration and mounting. To ascertain sensitivity and specificity, immunohistochemistry was performed omitting the primary antibodies on control sections. Expression levels of BARD1 and BRCA1 were measured semi-quantitatively. Staining was scored using intensity and percentage of the stained tumor cells. The value of the staining intensity and positive cell percentage were multiplied to get the final staining score. The total staining score of each antibody is from 0 to 100, 25 or less staining score is definited negative staining ("−"), more than 25 is definited positive staining ("+"), and it was distinguished "+", "++", and "+++" according to the total staining score more than 25 to 50, more than 50 to 75, and more than 75. For statistical analysis, only positive versus negative cases were considered, except the correlation of different antibodies staining using staining score. Four different regions were chosen for each tumor section and scored independently by three observers (Y,Z; L,L and J,W) without knowledge of clinical data.

RNA/RT-PCR Analysis

RT-PCR was performed to qualitatively determine the expression of different isoforms and to investigate their structure. RNA was isolated from frozen tissue sections using Trizol reagent. Chloroform (0.1 ml) was added and samples centrifuged at 14,000 g for 15 min at 4° C. to separate the phases. The aqueous phase was transferred to an RNase-free Eppendorf tube, and an equal volume of isopropanol added for RNA precipitation. The RNA pellet was washed with 75 percent ethanol and dissolved in 20 µl RNase-free water. Concentrations were measured to ascertain that D260/D280 ratios were at least 1.8.

For reverse transcription, 1 µg of RNA was used in 21 µl of reverse transcriptase buffer containing 1 µl of dNTPs (10 mM), 1 µl of oligo dT, 2 µl of DTT (0.1 M), 4 µl of first-stand buffer and 1 µl of Superscript II. Reactions were performed at 65° C. for 5 min, followed by 42° C. for 2 min, 42° C. for 50 min, and 70° C. for 15 min. Two µl cDNA was used as a template for PCR with different primers.

Estrogen Receptor α (ERα) was amplified using annealing temperature 56° C. and extension times 1 min with primers 5'-ACAAGCGCCAGAGAGATGAT-3' (SEQ ID NO: 81) and 5'-GATGTGGGAGAGGATGAGGA-3' (SEQ ID NO: 82). Glyceraldehyde-3-phosphate dehydrogenase (GAPDH) was amplified as internal control with primers 5'-AGCCACATCGCTCAGACACC-3' (SEQ ID NO: 83) and 5'-GTATCTAGCGCCAGCATCG-3' (SEQ ID NO:84). The same volume of PCR product was used on agarose/TBE gels (0.8% for FL, 1% for others) containing 0.1 µg/ml ethidium bromide (EtBr) for analysis the same size fragment of BARD1 (20 µl for exon 1-11, 10 µl for exon 1-4, 5 µl for others) and visualization under UV light.

PCR products (10 µl) were analyzed on 1% of agarose/TAE gels supplemented with ethidium bromide and visualized under UV light. Please refer to Table 3 for a complete list of primers and conditions.

The QIAEX II kit (Qiagen, Hombrechtikon, Switzerland) was used for DNA purification. Sequencing was performed with internal BARD1 primers.

TABLE 3

| Forward primer | | Reverse primer | | | | |
|---|---|---|---|---|---|---|
| Sequence | Position (bp) (Exon) | Sequence | Position (bp) (exon) | PCR product (bp) | Anealing Tem (° C.) | Extension (sec) |
| 5' GAGGAGCCTTTCATCCGAAG 3' (SEQ ID NO: 85) | −28 (Ex 1) | 5' ATTGCAGGCTGGGTTTGCAC TGAAG 3' (SEQ ID NO: 95) | 506 (Ex 4) | 534 | 56 | 60 |
| 5' GAGGAGCCTTTCATCCGAAG 3' (SEQ ID NO: 86) | −28 (Ex 1) | 5' TTTTGATACCCGGTGGTGTT 3' (SEQ ID NO: 96) | 1481 (Ex 6) | 1509 | 56 | 90 |

TABLE 3-continued

| Forward primer | | Reverse primer | | | | |
|---|---|---|---|---|---|---|
| Sequence | Position (bp) (Exon) | Sequence | Position (bp) (exon) | PCR product (bp) | Anealing Tem (° C.) | Extension (sec) |
| 5' GAGGAGCCTTTCATCCGAAG 3' (SEQ ID NO: 87) | -28 (Ex 1) | 5' CGAACCCTCTCTGGGTGATA 3' (SEQ ID NO: 97) | 2252 (Ex 11) | 2280 | 56 | 120 |
| 5' GTTTAGCCCTCGAAGTAAGAAAG 3' (SEQ ID NO: 88) | 438 (Ex 4) | 5' CGAACCCTCTCTGGGTGATA 3' (SEQ ID NO: 98) | 2252 (Ex 11) | 1815 | 56 | 120 |
| 5' GTCAGATATGTTGTGAGTAAAGCTTC 3' (SEQ ID NO: 89) | 461 (Ex 4) | 5' CGAACCCTCTCTGGGTGATA 3' (SEQ ID NO: 99) | 2252 (Ex 11) | 1792 | 56 | 120 |
| 5' AGCAAGTGGCTCCTTGACAG 3' (SEQ ID NO: 90) | 783 (Ex 4) | 5' CGAACCCTCTCTGGGTGATA 3' (SEQ ID NO: 100) | 2252 (Ex 11) | 1470 | 56 | 90 |
| 5' CCAGTCCCATTTCTAAGAGATGTAG 3' (SEQ ID NO: 91) | 986 (Ex 4) | 5' CGAACCCTCTCTGGGTGATA 3' (SEQ ID NO: 101) | 2252 (Ex 11) | 1267 | 56 | 90 |
| 5' GAGGAGAGACTTTGCTCC 3' (SEQ ID NO: 92) | 1280 (Ex 4) | 5' CGAACCCTCTCTGGGTGATA 3' (SEQ ID NO: 102) | 2252 (Ex 11) | 973 | 56 | 60 |
| 5' GCTGGATGGACACCATTG 3' (SEQ ID NO: 93) | 1378 (Ex 5) | 5' CGAACCCTCTCTGGGTGATA 3' (SEQ ID NO: 103) | 2252 (Ex 11) | 875 | 56 | 60 |
| 5' CTCCAGCATAAGGCATTGGT 3' (SEQ ID NO: 94) | 1441 (Ex 6) | 5' CGAACCCTCTCTGGGTGATA 3' (SEQ ID NO: 104) | 2252 (Ex 11) | 812 | 56 | 60 |

Image Analysis for PCR

Images were manipulated by ImageJ, Java-based image processing software (National Institutes of Health, http://rsbweb.nih.gov/ij/). PCR products were subjected to agarose gel, visualized with Ethidium bromide staining and photographed. Images were saved as JPG files before being converted to greyscale for analysis. The image was opened in ImageJ, calibration function was set to un-calibrated OD for each image before measurement. The rectangle tool was used to draw the area for measurement of the same size of PCR bands. The same size of band in DNA ladder closing the size of interest bands in samples were used to get the relative accurate values in different gels based on adjusting the area of rectangle. The area of the peak was outlined. The proportion of the peak area as a percentage of the total area under the curve was used for statistical analysis.

Total RNA Extraction, Reverse Transcription and PCR

RT-PCR was performed to qualitatively show expression of different isoforms and to determine their structure. RNA isolation from frozen tissue sections was obtained using Trizol reagent according to the protocol of RNA isolation. Chloroform (0.1 ml) was added, and samples were centrifuged at 14,000 g for 15 min at 4° C. to separate the phases. The aqueous phase was transferred to an RNase-free Eppendorf tube, and an equal volume of isopropanol was added for RNA precipitation. RNA pellet was washed with 75 percent ethanol and dissolved in 20 µl RNase-free water. Concentrations were measured to ascertain that D260/D280 ratios were at least 1.8.

For reverse transcription, 1.5 µg of RNA was used in final volume of 25 µl, containing M-MLV RT 5× Reaction Buffer 5 µl, 2 µl of oligo dT (500 µg/ml), 1.5 µl of 10 mM dNTP's, Recombinant RNasin Ribonuclease Inhibitor 1 µl (25 u/µl) and 1 µl of M-MLV Reverse Transcriptase (200 u/µl). The reaction was incubated at 70° C. 5 minutes followed by 42° C. 60 minutes and 70° C. 10 minutes. Three µl of cDNA were used as a template for amplification of FL BARD1, and 2 µl of cDNA were used for amplification of various fragments of BARD1. PCR was performed with Taq polymerase in a final volume of 50 µl. Primary denaturation (94° C., 2 min) and final extension (72° C., 10 min) were the same for all PCR reactions. Annealing temperatures and extension times were variable according to different primers and length of the expected product for BARD1 (Table 3).

Estrogen Receptor α (ERα) was amplified using annealing temperature 56° C. and extension times 1 min with primers 5'-ACAAGCGCCAGAGAGATGAT-3' (SEQ ID NO: 81) and 5'-GATGTGGGAGAGGATGAGGA-3' (SEQ ID NO: 82). Glyceraldehyde-3-phosphate dehydrogenase (GAPDH) was amplified as internal control with primers 5'-AGCCACATCGCTCAGACACC-3' (SEQ ID NO:83) and 5'-GTATCTAGCGCCAGCATCG-3' (SEQ ID NO:84). The same volume of PCR product was loaded on agarose/TBE gels (0.8% for FL, 1% for others) containing 0.1 µg/ml ethidium bromide (EtBr) for visualization of fragment of BARD1 (20 µl for exon 1-11, 10 µl for exon 1-4, 5 µl for others) under UV light.

The QIAEX II kit (Qiagen, Hombrechtikon, Switzerland) was used for DNA purification of RT-PCR products according to the manufacturer's instruction followed by sequencing with forward and reverse primers used for PCR, or additional primers within the fragments if no overlapped sequence was produced.

Mouse Model

Lung tumors were chemically induced in BALB/c mice as described in Redente E F, Dwyer-Nield L D, Barrett B S, et al: Lung tumor growth is stimulated in IFN-gamma–/– mice and inhibited in IL-4Ralpha–/– mice. Anticancer Res 29:5095-101, 2009. Male mice, 6-8 weeks of age, were injected intraperitoneally with one mg urethane per g body weight once weekly for seven weeks. Mice were sacrificed 16, 24 and 32 weeks after treatment. Lung tissue and tumors were dissected and processed for immunochemistry analysis. Tissues from three mice were analyzed for each time point.

Statistical Analysis

The Spearman's correlation coefficient ρ was used to assess the correlation between expression levels of BARD1 and BRCA1 epitopes. The χ2 test was used to compare the percentage of positive cases in tumor versus peritumor tissues, and correlation of positive cases of BARD1 expression with clinical variables. The T-test was used to measure the correlation of BARD1 expression level with clinical variables. For associations with survival, patients were further placed into two groups according to their BARD1 expression levels. Survival differences were estimated using Kaplan-Meier method and compared by the log-rank test. For all calculations, the tests were two-sided, and a value of P<0.05 was considered statistically significant. Analyses were performed using Statistical Package for the Social Sciences (SPSS) for Windows version 13 (SPSS Inc, Chicago, Ill.).

II

Results

Immunohistochemistry on sections of tumors was performed, comprising different types, grades, and stages from 100 patients (Table 1). Antibodies recognizing four different epitopes of BARD1 (mapping to exons 1, 3, 4, and 11) were used, which could theoretically result in 16 different staining patterns. Surprisingly, only few distinct patterns were observed, and staining for all four antibodies was observed in the majority of tumors (FIG. 1A-E). Staining of adjacent sections showed that different epitopes were expressed in different regions of tumor sections and in different sub-cellular compartments (FIG. 1B-D), suggesting that different isoforms of BARD1 were expressed within a single tumor. Typically, BARD1-N19 (exon 1) and C20 (exon 11) showed cytoplasmic granular staining and were co-localized to the same regions of a tumor. BARD1 PVC (exons 3) and WFS (exon 4) immunostainings were diffuse and in the cytoplasm. These differences in intensity and intracellular localization of stainings suggested that expression of all four epitopes did not reflect the expression of wild type BARD1, but rather the simultaneous expression of different isoforms.

The expression levels of N19 and C20 strongly correlated with each other, as was the case for PVC and WFS (FIG. 1F), but other antibody staining patterns did not correlate. Thus it could be concluded that N-terminally and C-terminally truncated forms, as well as forms with internal deletions, are expressed in NSCLC. Particularly, the WFS (5' end of exon 4) staining was upregulated in many lung cancers, in contrast to the epitope expression pattern observed for ovarian cancers, where WFS staining was rare.

BRCA1 and BARD1 co-expression in adjacent tissue sections (FIG. 1B-D) was investigated. BRCA1 was expressed in 66.7% of NSCLC samples, but it did not correlate with expression of any the BARD1 epitopes. As BRCA1 is not co-expressed with BARD1, these data suggest that functions of the BRCA1-BARD1 heterodimer are lost in NSCLC.

Figure 2:
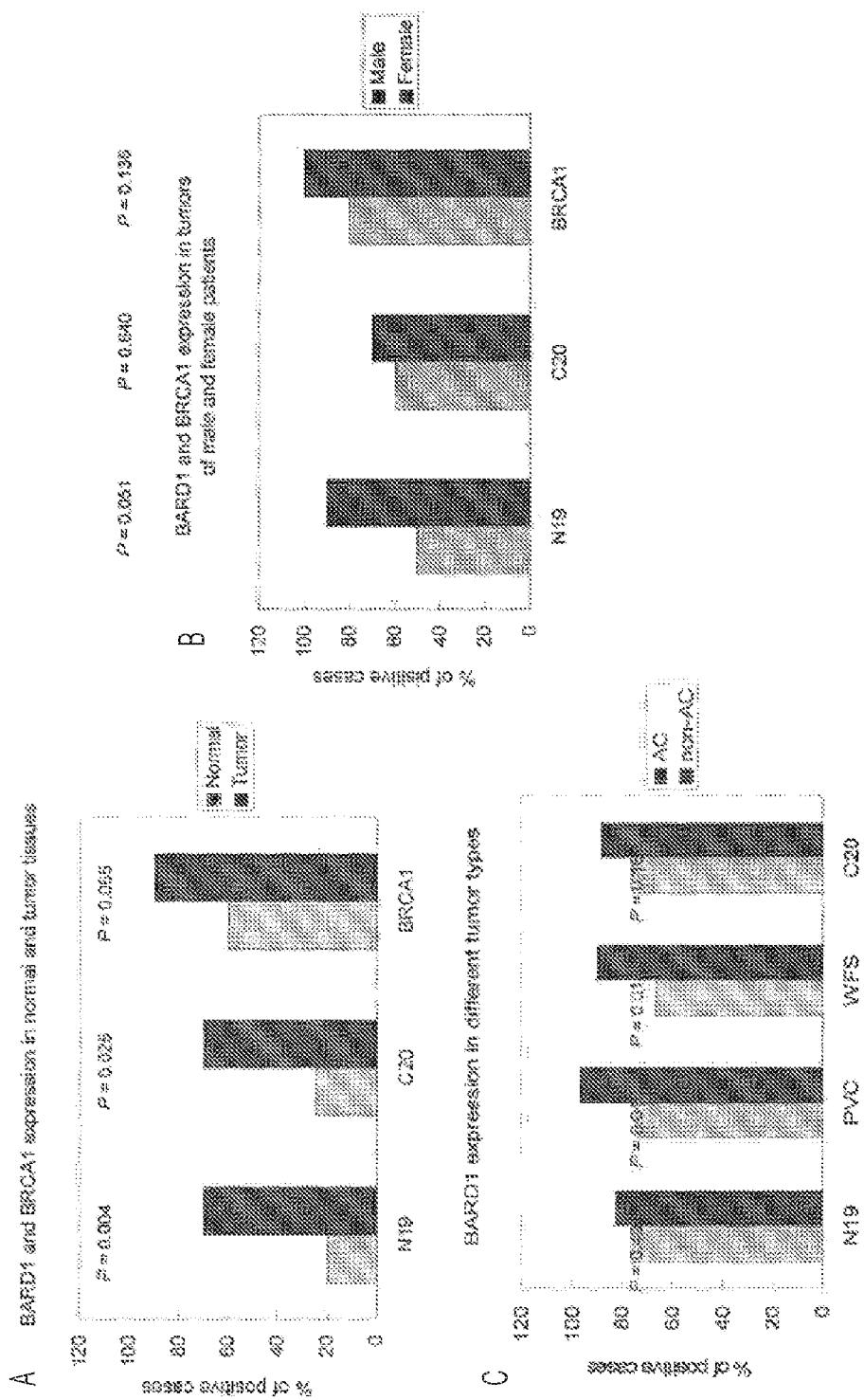
FIG. 2 shows Comparison of BARD1 expression in tumour and peri-tumour tissues and correlation with clinical features. (A) Comparison of BARD1 N19, BARD1 C20, and BRCA1 staining in tumour and peri-tumour tissues of 20 (10 female and 10 male) NSCLC patients. Staining for all antibodies was increased in tumour tissues as compared to "normal" tissues. (B) BARD1 N19, BARD1 C20, and BRCA1 staining were tested in tumour tissues 10 female and 10 male NSCLC patients. Staining for all antibodies was increased in tumours from female as compared to male patients. (C) Comparison of BARD antibody staining and tumour types in 100 NSCLC cases. Positive staining was more frequent in non-adenocarcinoma (AC) (including squamous cell carcinoma and large cell carcinoma) than in AC. Increased PVC and WFS stainings were statistically significant. (D-I) Correlation of BARD1 expression with patient survival. (D, F, H) Kaplan-Meyer analysis of disease free survival (DFS) according to the PVC antibody (D), the WFS antibody (F) or the combination of the PVC antibody and the WFS antibody (H) positive staining, as defined in FIG. 1E. (E, G, I) Kaplan-Meyer analysis of overall survival (OS) according to the PVC antibody (E), the WFS antibody (G) or the combination of the PVC antibody and the WFS antibody (I) positive staining, as defined in FIG. 1E.
Figure 2:
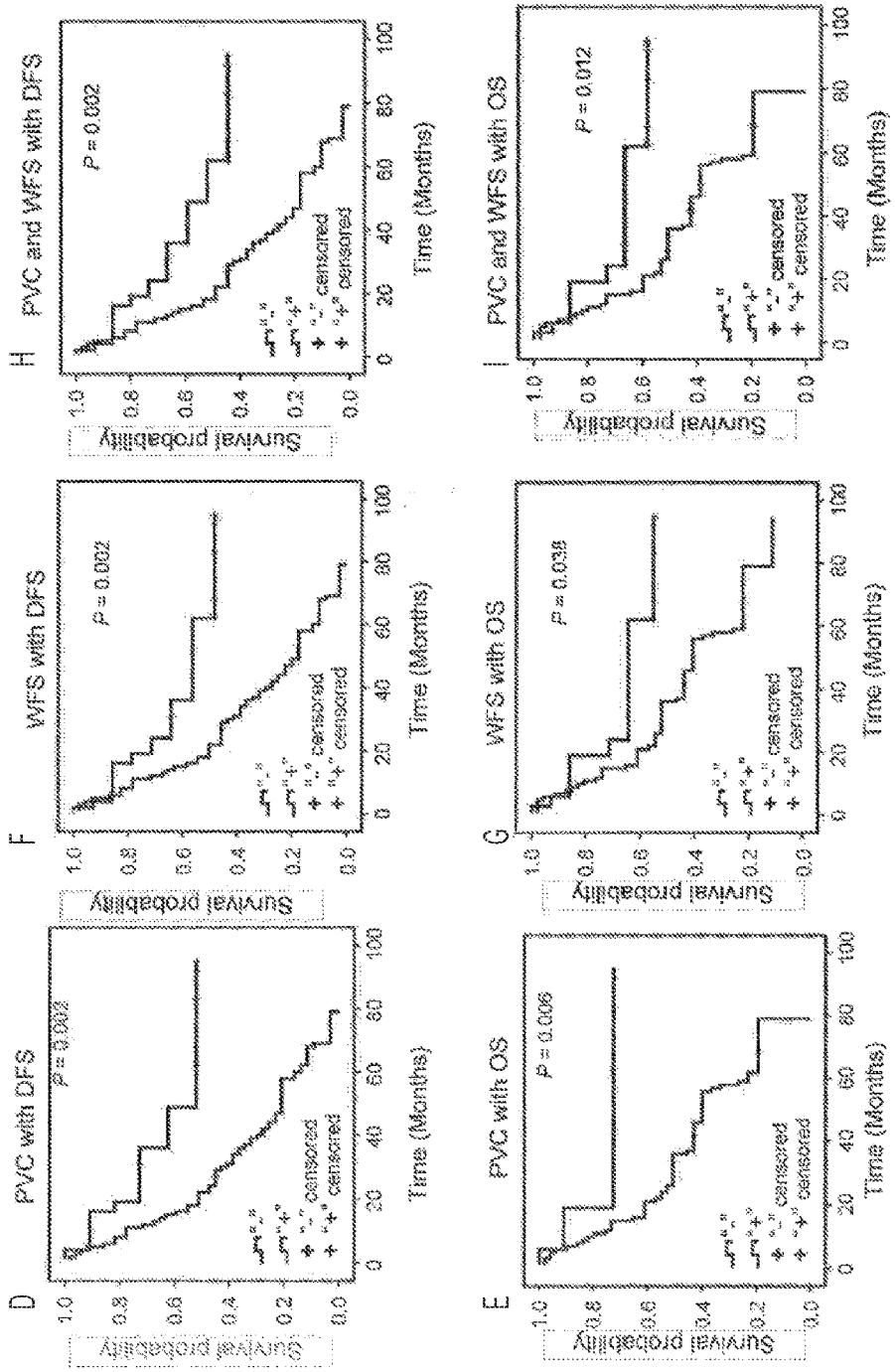

BARD1 expression in tumor and normal peri-tumor tissue was observed, although more elevated in tumors (FIG. 2A; FIG. 5). Expression was generally higher in tumors from female than from male patients (FIG. 2B).

The expression of specific BARD1 epitopes was less frequent in adenocarcinomas than in non-adenocarcinomas (including squamous cell carcinoma and large cell carcinoma) (FIG. 2C). However, no correlation of antibody staining with tumor grade and stage was found (data not shown).

Individual epitopes of BARD1 expression and expression pattern with disease free survival (DFS) and overall survival (OS) in 65 patients with follow-up data was also evaluated. Patients with individual PVC (FIG. 2D, E) and WFS (FIG. 2F, G) positive staining had significantly shorter DFS (FIG. D, F) and shorter OS (FIG. 2E, G) than those with negative staining. Most importantly, patients with PVC and WFS simultaneously positive staining pattern showed a very shorter survival compared with those who had different combinations (FIG. 2H, I). No correlations were observed between N19, C20, and other staining patterns and either DFS or OS.

Univariate and multivariate analysis using Cox's proportional hazards model were performed to evaluate whether the markers analyzed have an independent prognostic significance. In the univariate analysis, pathologic stage also showed prediction of DFS and OS (Table 5). The pathologic stage and another two possible prognostic factors, histologic type and patient gender, were entered into a multivariate model. This latter analysis showed that individual PVC and WFS positive staining, PVC and WFS simultaneously positive staining pattern, and pathologic stage preserve independent prognostic significance for both DFS and OS (Table 5).

TABLE 4

Univariate analysis of survival in 65 NSCLC patients with follow-up data

| Predictors | DFS | | | OS | | |
|---|---|---|---|---|---|---|
| | HR | 95% CI | P | HR | 95% CI | P |
| N19 pos vs neg | 1.08 | 0.50-2.32 | 0.849 | 1.11 | 0.46-2.67 | 0.811 |
| PVC pos vs neg | 3.84 | 1.50-9.87 | 0.005 | 4.79 | 1.41-16.2 | 0.012 |
| WFS pos vs neg | 3.39 | 1.50-7.67 | 0.003 | 2.47 | 1.01-6.00 | 0.047 |
| C20 pos vs neg | 1.26 | 0.53-2.98 | 0.602 | 1.45 | 0.51-4.12 | 0.481 |
| N19 and C20 pos vs others | 1.08 | 0.50-2.32 | 0.849 | 1.11 | 0.46-2.67 | 0.811 |
| PVC and WFS pos vs others | 3.22 | 1.49-6.96 | 0.003 | 3.02 | 1.22-7.46 | 0.017 |
| 4 Abs pos vs others | 2.04 | 1.11-3.77 | 0.123 | 1.86 | 0.91-3.81 | 0.091 |
| Stage III, IV vs I, II | 3.04 | 1.61-5.72 | 0.001 | 3.60 | 1.85-7.02 | 0.000 |
| AC vs non-AC | 0.72 | 0.41-1.24 | 0.232 | 0.62 | 0.33-1.14 | 0.124 |
| Grade 3, 4 vs 1, 2 | 1.50 | 0.84-2.66 | 0.167 | 1.87 | 0.96-3.66 | 0.068 |
| Age (years) ≤60 vs >60 | 1.06 | 0.61-1.83 | 0.837 | 1.21 | 0.64-2.28 | 0.557 |
| Male vs female | 1.35 | 0.65-2.80 | 0.414 | 0.89 | 0.35-2.27 | 0.804 |

Note:
HR, hazard ratio; 95% CI, 95% confidence interval; P, P - value; pos, positive staining; neg, negative staining. AC, adenocarcinoma; non-AC, including squamous cell carcinoma and large cell carcinoma; others, all other combinations.

TABLE 5

Multivariate analysis of survival in 65 NSCLC patients with follow-up data

| Predictors | DFS | | | OS | | |
|---|---|---|---|---|---|---|
| | HR | 95% CI | P | HR | 95% CI | P |
| PVC pos vs neg* | 2.94 | 1.09-7.94 | 0.034 | 3.36 | 0.93-12.1 | 0.064 |
| Stage III, IV vs I, II | 2.47 | 1.26-4.85 | 0.009 | 2.96 | 1.46-6.00 | 0.003 |
| AC vs non-AC | 1.34 | 0.73-2.48 | 0.348 | 1.51 | 0.76-3.01 | 0.238 |
| Male vs female | 1.42 | 0.66-3.03 | 0.367 | 1.09 | 0.41-2.90 | 0.865 |
| WFS pos vs neg* | 3.81 | 1.61-9.04 | 0.002 | 2.52 | 0.98-6.53 | 0.056 |
| Stage III, IV vs I, II | 3.71 | 1.86-7.41 | 0.000 | 3.97 | 1.94-8.15 | 0.000 |
| AC vs non-AC | 1.14 | 0.62-2.11 | 0.668 | 1.41 | 0.70-2.85 | 0.336 |
| Male vs female | 1.58 | 0.74-3.39 | 0.242 | 1.26 | 0.47-3.39 | 0.645 |

TABLE 5-continued

Multivariate analysis of survival in
65 NSCLC patients with follow-up data

| Predictors | DFS | | | OS | | |
|---|---|---|---|---|---|---|
| | HR | 95% CI | P | HR | 95% CI | P |
| PVC and WFS pos vs others* | 3.50 | 1.54-7.95 | 0.003 | 3.03 | 1.16-7.94 | 0.024 |
| Stage III, IV vs I, II | 3.56 | 1.79-7.06 | 0.000 | 3.93 | 1.92-8.04 | 0.000 |
| AC vs non-AC | 1.12 | 0.60-2.08 | 0.718 | 1.31 | 0.65-2.65 | 0.449 |
| Male vs female | 1.52 | 0.70-3.26 | 0.287 | 1.23 | 0.46-3.31 | 0.678 |

Note:
HR, hazard ratio; 95% CI, 95% confidence interval; P, P - value; pos, positive staining; neg, negative staining. AC, adenocarcinoma; non-AC, including squamous cell carcinoma and large cell carcinoma; others, all other combinations.
*HR adjusted for all the other predictors in the model (pathology, stage and sex)

In another example of the present invention, a correlation of BARD1 isoforms with initiation and progression of lung cancer was showed, wherein BARD1 expression in experimentally induced lung cancer was monitored. Multiple injections of urethane into BALB/c mice induce primary lung tumors progressing into adenocarcinomas. This treatment leads to macroscopic tumors at 16 weeks; they become larger at 24 weeks, and invade into normal adjacent tissue after 32 weeks. Normal tissues and tumor regions at all stages were selected and scored the antibody staining (FIG. 3). Consistently, expression of PVC and WFS was weak, and C20 was strong in control animals. This pattern was similar in 16 weeks tumors. However, in 24 week tumors, PVC and WFS expressions increased in comparison to C20 and were highly upregulated in 32 week tumors. These experiments demonstrate that the BARD1 expression pattern changes during different stages of tumorigenesis and suggest that BARD1 epitopes mapping to exons 3 and 4 may be involved in tumor promotion and progression towards an invasive stage.

The structure of different isoforms expressed in NSCLC was determined by RT-PCR with primers amplifying the entire BARD1 coding region from samples of 10 female and 10 male patients. RNA was extracted from tumor tissue and from normal peri-tumor tissue. Normal lung control tissue was obtained from patients with benign respiratory pathologies. BARD1 expression in normal lung was absent or very low; only weak expression of BARD1 was found in controls by RT-PCR (FIG. 4A) and by immunohistochemistry (data not shown). RT-PCR from NSCLC patients showed expression of FL BARD1 and several different isoforms thereof in most tumor and peri-tumor samples. In most cases, the specific expression pattern of FL BARD1 and isoforms were identical in normal peri-tumor and tumor tissues (FIG. 4B).

To distinguish isoforms of similar molecular weight, RT-PCR was performed with primers amplifying the exons 1 and 4, or 1 and 6. It was found, in addition to FL BARD1, the expression of already know isoform β, but not α (WO 2008/119802) and additional two new isoforms κ and π (FIG. 4B, C, E, FIG. 6 and FIG. 7).

The expression of isoforms obtained by RT-PCR in female and male cases was quantified. FL and isoforms were similarly expressed in tumors and in peri-tumor tissue, in contrast to the significant upregulation of BARD1 isoforms at the protein level (FIG. 1A and FIG. 5). Expression of isoforms BARD1β and κ was significantly upregulated in males as compared to females (P<0.05), while expression of isoforms BARD1η, BARD1γ, and BARD1ε was upregulated in females as compared to males (FIG. 7).

In another example of the present invention, ERα expression was found in all lung tissues from females and males, both in normal and peri-tumor tissues (FIG. 4D), which suggests that BARD1 isoforms might be related to estrogen signalling in NSCLC.

III

Results

BARD1 expression in colorectal cancer was investigated by performing IHC on tumor sections from 148 paraffin-embedded tissue samples of colorectal cancer presented as tissue microarray with tetramerous for each of the cases (Table 2). One hundred and forty-five cases were eligible for analysis after IHC assay, and they were analyzed in this study. Four antibodies (N19, PVC, WFS and C20) against different regions of BARD1 (exon 1, exon 3, exon 4 and exon 11, respectively) were used to distinguish different BARD1 epitopes on adjacent tissue sections (FIG. 1A). BRCA1 expression was also investigated using BRCA1 C20 antibody against C-terminal epitope of BRCA1.

The positive staining for each of the four antibodies was variable in colorectal cancer (FIG. 9A). BARD1 N19, PVC, WFS and C20 staining were classified as positive in 36 (24.8%), 122 (84.1%), 129 (89%) and 61 (42.1%) cases of colorectal cancer, respectively. 142 cases were observed with at least one antibody positive staining, and no expression of BARD1 was found in only three cases (FIG. 9B). In other words, 97.9% (142 of 145) of colorectal cancer cases expressed at least one epitope of BARD1.

Although in principle 16 different combinations for expressing of the 4 epitopes are possible, only three major combinations were found (FIG. 9B). These 3 BARD1 expression patterns in colorectal cancer included: expression of only the middle epitopes was the most frequent (38.6%) (FIG. 8B, D), staining for all four antibodies was the second (18.6%) (FIG. 8B, C, E), loss of the N-terminal epitope was third (17.9%) (FIG. 8B, F) most frequently observed expression pattern.

Like BARD1 expression in NSCLC tissues, it was found that all four antibodies staining were cytoplasmic but in different regions. BARD1 N19 and C20 showed granular staining, while PVC and WFS showed diffuse staining, and they were colocalized to the same cells or same regions, respectively (FIG. 8C-F). To investigate this further, the expression pattern obtained with each antibody was quantified and compared the results. Strong correlation was observed between expression levels of N19 and C20 (p=0.71; P=0.000). Others, comparisons such as PVC and WFS (p=0.39; P=0.000), PVC and C20 (p=0.36; P=0.000), and WFS and C20 (p=0.27; P=0.001) showed weak correlations. No correlation was found between N19 and PVC, and N19 and WFS staining (FIG. 10A).

From the different epitope expression levels, the intracellular localization, the intensity of staining with different antibodies, the correlated or uncorrelated expression of different BARD1 epitopes, and the expression patterns with four antibodies against different BARD1 epitopes, it was possible to conclude that N-terminally and C-terminally truncated forms, loss of the N-terminus forms, as well as forms which contain the four epitopes reactive with antibodies used in this study, were expressed in colorectal cancer.

IV

Non-Coordinate Expression of BARD1 and BRCA1

Figure 8C:
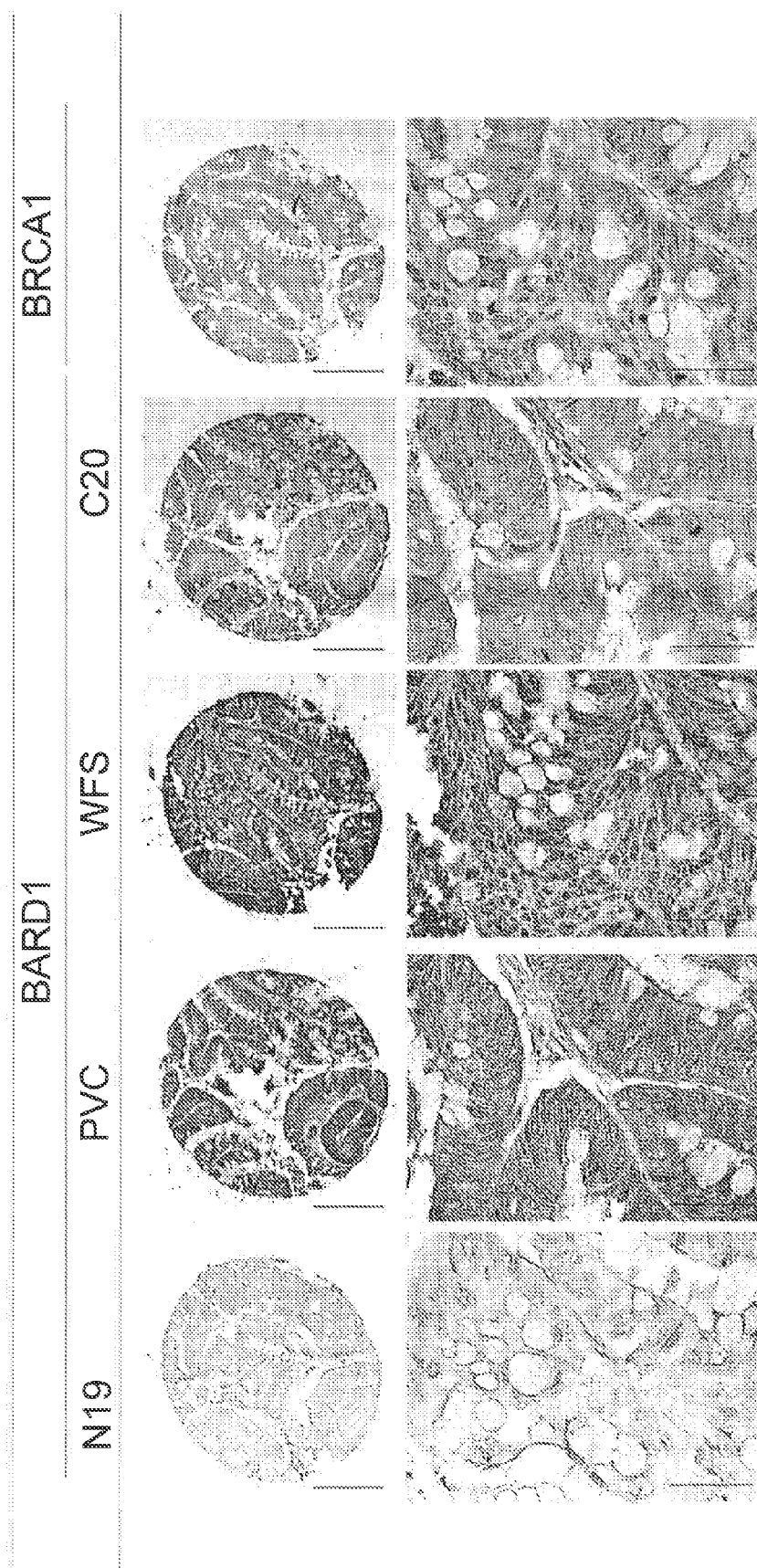
Figure 8D:
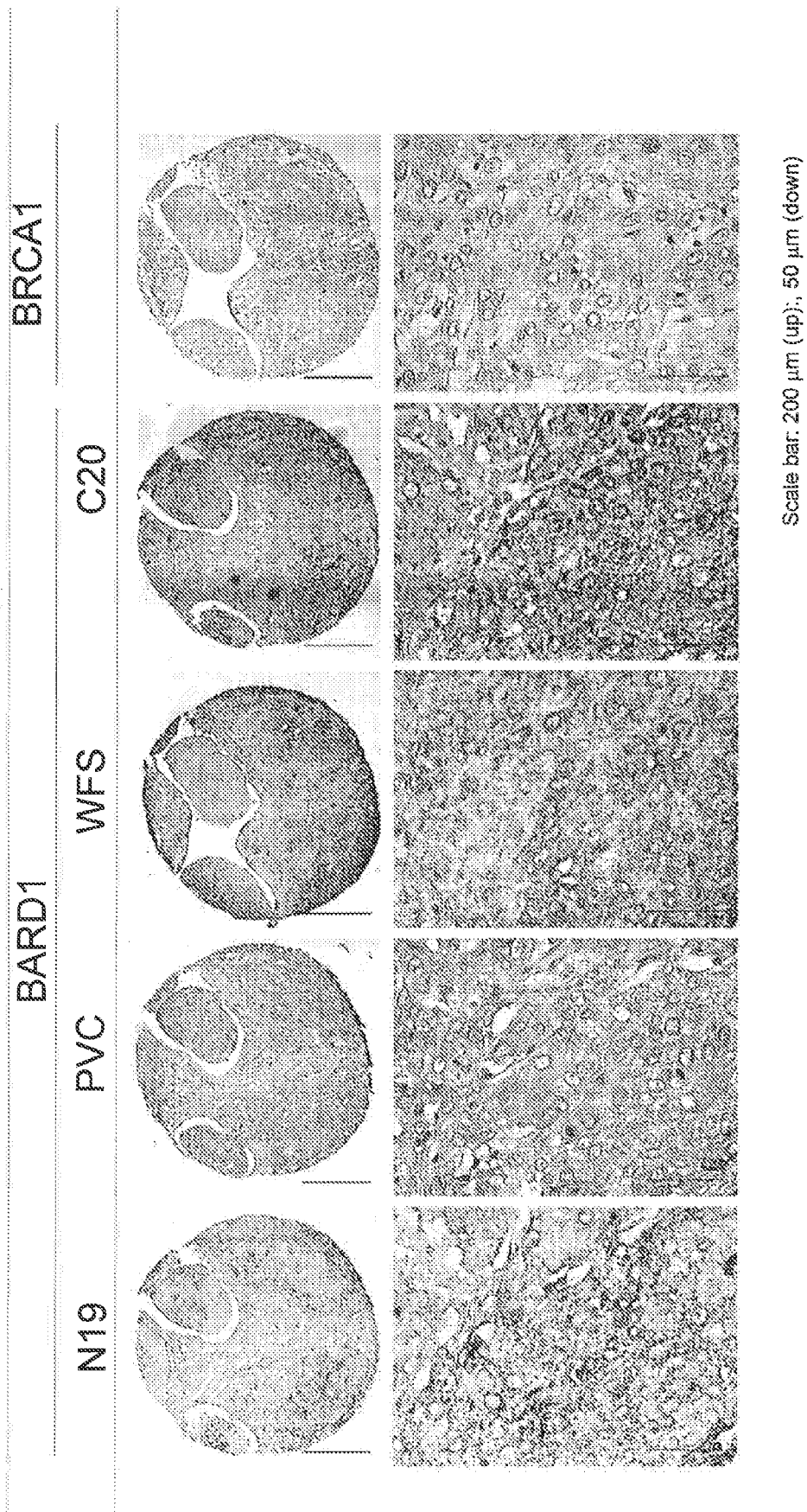

Unlike BARD1, BRCA1 staining showed both cytoplasmic and nuclear granular staining within the same cell (FIG. 8C). BRCA1 positive staining was observed in 22.1% (32 of 145) of colorectal cancer cases, while N19 positive staining was observed in 24.8% (36 of 145) cases. Interestingly, only 7 of 61 cases (11.5%) that were N19 positive were also BRCA1 positive. Moreover, no correlations were found between BRCA1 expression and distinct epitopes of BARD1 expression (FIG. 10B). These results demonstrated that BRCA1 expression was not coordinated with BARD1 in colorectal cancer.

V

Correlation of BARD1 Protein Expression with Clinicopathological Characteristics and Patients Prognosis Frequency of N19 positive staining was significantly associated with female sex (P=0.014) (FIG. 11A), this is consistent with the results that BARD1 N19 over expressed in female than in male in NSCLC (FIG. 2B). BARD1 different epitopes expression and BRCA1 expression were not correlated with any of other clinicopathologic variables, e.g. tumor grade, primary tumor, lymph node and distant metastasis status, and tumor stage (FIG. 4B-F). In addition, no significant correlation was obtained between different expression patterns and clinicopathological variables (data not shown).

The correlation of BARD1 and BRCA1 expression with survival was also assessed by comparing different BARD1 expression patterns (FIG. 9B) and expression of individual four epitopes of BARD1 and BRCA1 with survival in 75 colorectal cancer cases with follow-up data. It was found (Table 6) that patients with BARD1 N19 positive staining had higher 1-year, 2-year and 3-year survival rates, patients with C20 positive staining had higher 1-year and 3-year survival rates, as compared with their negative staining. No differences were obtained from comparison of BARD1 PVC and WFS (negative staining cases were not enough for further analysis), and BRCA1 positive and negative staining with survival.

When expression pattern was used as comparison (Table 7), it was found that the expression pattern of all four antibodies positive staining correlated with higher 1-year, 2-year and 3-year survival rates as compared with expression patterns of only the middle epitopes expression and other expression patterns in group. However, expression pattern of only the middle epitopes expression (detected with PVC and WFS) was correlated with lower 1-year, 2-year and 3-year survival rates as compared with other expression patterns in group, as well as comparison with all four antibodies positive staining pattern. No correlation was found between expression pattern of loss of the N-terminus epitope and other expression patterns, including expression pattern of all four antibodies positive staining (with the exception of 1-year survival rate), only the middle epitopes expression pattern, and all the other expression patterns in group.

Taken together it was possible to conclude that BARD1 expression pattern of all four antibodies positive staining is a positive prognostic factor, as well as expression of N-terminal epitope of BARD1; inversely, only the middle two epitopes simultaneous expression is a negative prognostic factor, but not their individual epitopes expression in colorectal cancer.

TABLE 6

Correlation of distinct epitopes of BARD1 and BRCA1 expression with survival in 75 colorectal cancer patients

| Abs | Expression level | No. of patients | Median survival (m) | 1- Year survival % | P-Value | 2- Year survival % | P-Value | 3- Year survival % | P-Value |
|---|---|---|---|---|---|---|---|---|---|
| N19 | "−":"+" | 55:20 | 11:26 | 47.3:85.0 | 0.0035 | 21.8:50.0 | 0.0178 | 12.7:40.0 | 0.009 |
| PVC | "−":"+" | 14:61 | 14:15 | 57.1:57.4 | 0.9873 | 28.6:29.5 | 0.9446 | 21.4:19.7 | 0.8822 |
| WFS | "−":"+" | 4:71 | | | | | | | |
| C20 | "−":"+" | 42:33 | 9:17 | 45.2:72.7 | 0.0169 | 21.4:39.4 | 0.0898 | 11.9:30.3 | 0.048 |
| BRCA1 | "−":"+" | 60:15 | 16:12 | 60.0:46.7 | 0.3504 | 31.7:20.0 | 0.3747 | 23.3:6.7 | 0.1489 |

Note:
"−", negative staining; "+", positive staining.
For WFS, negative staining cases were not enough for further analysis.

TABLE 7

Correlation of BARD1 expression patterns with survival in 75 colorectal cancer patients

| Expression pattern | No. of patients | Median survival (m) | 1- Year survival % | P-Value | 2- Year survival % | P-Value | 3- Year survival % | P-Value |
|---|---|---|---|---|---|---|---|---|
| ++++:−++− | 17:31 | 27:9 | 88.2:41.9 | 0.0019 | 52.9:16.1 | 0.0073 | 41.2:6.5 | 0.0032 |
| ++++:−+++ | 17:11 | 27:12 | 88.2:45.5 | 0.0144 | 52.9:18.2 | 0.0659 | 41.2:9.1 | 0.0664 |
| ++++:others | 17:58 | 27:12 | 88.2:48.3 | 0.0034 | 52.9:22.4 | 0.0151 | 41.2:13.8 | 0.0131 |
| −++−:−+++ | 31:11 | 9:12 | 41.9:45.5 | 0.839 | 16.1:18.2 | 0.875 | 6.5:9.1 | 0.7702 |

TABLE 7-continued

Correlation of BARD1 expression patterns with survival in 75 colorectal cancer patients

| Expression pattern | No. of patients | Median survival (m) | 1- Year survival % | P-Value | 2- Year survival % | P-Value | 3- Year survival % | P-Value |
|---|---|---|---|---|---|---|---|---|
| −++−:others | 31:44 | 9:16.5 | 41.9:68.2 | 0.0236 | 16.1:38.6 | 0.035 | 6.5:29.5 | 0.0138 |
| −+++:others | 11:64 | 12:15.5 | 45.5:59.4 | 0.3885 | 18.2:31.3 | 0.3792 | 9.1:21.9 | 0.3274 |

Note:
++++, four Abs positive staining; −++−, only PVC and WFS positive staining; −+++, only N19 negative staining; others, other than the expression pattern which is compared.

VI

Structure of BARD1 Isoforms Expressed in Colorectal Cancer

BARD1 mRNA level expression was assessed by RT-PCR in 20 tumor tissues and peri-tumor tissues, including 10 male and 10 female cases. RNA was extracted from frozen tissue sections. RT-PCR was performed using forward primer in exon 1 and reverse primers in exon 11 and exon 4 to amplify the BARD1 coding regions (exon 1 to exon 11, and exon 1 to exon 4), GAPDH was amplified as control. Together, ERα was also amplified from these series of samples, as did in NSCLC (FIG. 11A).

Unlike in NSCLC, BARD1 mRNA expression pattern were quite different in tumor tissues and peri-tumor tissues of the colorectum. FL BARD1 and isoforms were frequently expressed in most of tumor samples (90%, 18 of 20 cases); but in peri-tumor tissues, no BARD1 expression was frequent (65%, 13 of 20 cases), 7 cases (35%) expressed FL BARD1 only and/or less isoforms. This was statistically significant (P=0.0003). The similar results were also observed in males (8/10 vs 4/10, respectively) (P=0.0679) and in females (10/10 vs 3/10, respectively) (P=0.0010) (FIG. 12A). All BARD1 isoforms, which were expressed in NSCLC tissues including new isoform κ, with a deletion of exon 3, and new isoform π with a deletion of 408 bp within the 3' end of exon 4, were also expressed in colorectal cancer tissues. To accentuate, FL BARD1 and all BARD1 isoforms were frequently expressed in tumor tissues, but less or no expression in peri-tumor tissues (P<0.05 for all). (FIG. 12B).

VII

Similar BARD1 Expression Pattern Observed in Tissue from Males and Females

BARD1 isoforms β and κ were significantly up regulated in lung tissue from males and isoforms η, γ and ε were high expressed in lung tissue from females. Unlike in lung tissue, frequency of FL BARD1 and isoforms expression were similar in colorectal tissue from males and females, including in peri-tumor tissues (P>0.05 for all) (FIG. 12C) and in tumor tissues (P>0.05 for all) (FIG. 12D).

No ERα expression was found in colorectal tissues in the series samples, including in peri-tumor tissues and tumor tissues, in males and females (FIG. 11B). This result could, at least partially, explain that there was no correlation of BARD1 expression with males and females in colorectal tissues, as compared BARD1 expression in lung tissues.

VIII

Correlation of BARD1 Isoforms Expression with Clinical Variables

It was found that FL BARD1 and BARD1 isoforms were more frequently expressed in patients with age more than 60 years than equal or less than 60 years. Specially, frequency of BARD1 isoforms ϕ, δ and π expression were significantly associated with older age patients (P<0.01) (FIG. 13A). Moreover, BARD1 isoform κ expression in frequency was significantly associated with large tumor size or nearby tissue invasion (T3 and T4) (P=0.0098), lymph node involvement (N1 and N2) (P=0.0422), and advanced stages (stage III and IV) (P=0.0422) (FIG. 6B-D). No correlation was observed between BARD1 expression and tumor histopathological grade (FIG. 13E).

IX

Detection of Anti-BARD1 Autoimmune Antibodies in Blood of Lung Cancer Patients Method A test was developed based on immune absorption assays using the antigens of the present invention (BARD1 peptides) for capturing autoimmune antibodies in the blood of lung cancer patients. Method used for tests performed is an adaptation of a standard ELISA antibody capturing test. Specifically the following protocol was applied:

Microtiter plates (96 wells) are coated with BARD1 peptides [10 microgram/ml] diluted in PBS and incubation over night at 4° C.

Wells are blocked with Phosphat-buffered saline (PBS) substituted with blocking agent (e.g. 5% BSA) for one hour at room temperature with agitation.

Serum of patients and controls diluted in PBS containing 1% blocking agent is added to wells and incubated for two hours is performed with agitation at room temperature.

Wells are rinsed three times with PBS.

Secondary anti-human antibody coupled to HRP or Sulfo-Tag or equivalent detection reactive, diluted in PBS and 1% blocking agent, is added to wells and incubated for one hour at room temperature with agitation.

Wells are washed with PBS three times.

Read out is performed by adding HRP substrate or substrates for equivalent methods of detection, reactions are measured immediately.

Test

The following antigens (peptides) were tested on serum samples from lung cancer patients and on controls samples from healthy blood donors: SEQ ID NOs: 46, 33, 48, 20, 50, 19, 22, 16, 32, 26

Results

See FIG. 14. Healthy controls were compared with lung cancer patients. Values measured are arbitrary values. Values are generally higher in cancer patients than in controls. Combined values for several peptides results in a clear distinction between controls and cancer cases: sensitivity 100% and specificity 95% if 11 peptides are used.

Test Description

For example it is possible to use serum from patients to detect autoimmune antibodies against BARD1 isoforms. In control samples (healthy blood donors) the reaction values are significantly lower than in the cancer samples. Individual peptides can give high values for one control, but the use of a combination of peptides leads to exclusion of false positives.

The invention claimed is:

1. A method for detecting the presence of a BARD1 isoform specific to lung cancer and colorectal cancer, the method comprising the steps of:
   obtaining a biological sample from a subject;
   providing at least one polynucleotide primer or probe, wherein said polynucleotide primer or probe is specific for an mRNA that encodes the BARD1 isoform π consisting of SEQ ID NO:1 or a sequence having at least 99% homology to SEQ ID NO:1 and for an mRNA that encodes BARD1 isoform π' consisting of SEQ ID NO: 105 or a sequence having at least 99% homology to SEQ ID NO:105, wherein said BARD1 isoform π consisting of SEQ ID NO:1, said sequence having at least 99% homology to SEQ ID NO:1, said BARD1 isoform π' consisting of SEQ ID NO:105, and said sequence having at least 99% homology to SEQ ID NO:105 comprise a deletion within exon 4 of said BARD1 isoform, and wherein said primer or probe specifically binds to said mRNA at the deletion junction of said deletion within exon 4; and
   detecting in said sample the mRNA encoding said sequence by detecting specific binding of said polynucleotide primer or probe to said mRNA, thereby detecting the presence of said BARD1 isoform specific to lung cancer and colorectal cancer,
   wherein the presence of said BARD1 isoform π or isoform π' specific to lung cancer and colorectal cancer in a sample from said subject is an indication that said subject is afflicted with lung cancer and/or colorectal cancer, has an increased risk of lung cancer and/or colorectal cancer, a risk of recurrence after a treatment for lung cancer and/or colorectal cancer, and/or is an indication of reduced survival of a patient afflicted with lung cancer.

2. The method of claim 1, wherein said method comprises the step of detecting in said biological sample BARD1 isoform π consisting of SEQ ID NO:1 and BARD1 isoform κ consisting of SEQ ID NO:2.

3. The method of claim 1, wherein said method further comprises detecting in said biological sample at least one of the BARD1 isoforms selected from the group comprising
   isoform π' comprising SEQ ID NO:105, a biologically active fragment thereof, or a sequence having at least 95% homology to SEQ ID NO:105,
   isoform β comprising SEQ ID NO:5, a biologically active fragment thereof, or a sequence having at least 95% homology to SEQ ID NO:5,
   isoform δ comprising SEQ ID NO:6, a biologically active fragment thereof, or a sequence having at least 95% homology to SEQ ID NO:6, and
   isoform γ comprising SEQ ID NO:7, a biologically active fragment thereof, or a sequence having at least 95% homology to SEQ ID NO:7,
   isoform β' comprising SEQ ID NO:106, a biologically active fragment thereof, or a sequence having at least 95% homology to SEQ ID NO:106.

4. The method of claim 3, wherein said method comprises detecting in said biological sample BARD1 isoform π consisting of SEQ ID NO:1, BARD1 isoform κ consisting of SEQ ID NO:2 and BARD1 isoform β consisting of SEQ ID NO:5.

5. The method according to claim 1, wherein said biological sample is selected from the group comprising a biopsy sample, a histology sample, lung liquids, frozen tissue sample, tumor tissue sample, feces sample, cerebrospinal fluid (CSF), circulating tumour cells (CTC) and blood sample.

6. The method according to claim 1, wherein said subject is a human.

7. The method of claim 1, wherein the presence of said BARD1 isoforms is detected by using antibodies specific to said BARD1 isoforms.

8. The method of claim 7, wherein said antibodies are a combination of antibodies or fragments thereof that specifically bind to different epitopes of at least one of the BARD1 isoforms comprising amino acid sequences selected from the group comprising SEQ ID NOs:1-7, 105-106 biologically active fragments thereof, or sequences having at least 95% homology to SEQ ID NOs:1-7, 105-106.

9. The method of claim 1, wherein the presence of said BARD1 isoforms is detected by detecting the level of mRNA that encodes at least one of the BARD1 isoforms comprising amino acid sequences selected from the group comprising SEQ ID NOs:1-7, 105-106, biologically active fragments thereof, or sequences having at least 95% homology to SEQ ID NOs:1-7, 105-106.

10. A method for discriminating lung cancer and colorectal cancer from gynecological cancers, said method comprising the steps of:
obtaining a biological sample from a subject;
providing at least one polynucleotide primer or probe, wherein said polynucleotide primer or probe is specific for an mRNA that encodes the BARD1 isoform π consisting of SEQ ID NO:1 or a sequence having at least 99% homology to SEQ ID NO:1 and for an mRNA that encodes BARD1 isoform π' consisting of SEQ ID NO:105 or a sequence having at least 99% homology to SEQ ID NO:105, wherein said BARD1 isoform π consisting of SEQ ID NO:1, said sequence having at least 99% homology to SEQ ID NO:1, said BARD1 isoform π' consisting of SEQ ID NO:105, and said sequence having at least 99% homology to SEQ ID NO:105 comprise a deletion within exon 4 of said BARD1 isoform, and wherein said primer or probe specifically binds to a deletion junction of said deletion within exon 4; and
detecting in said sample the mRNA encoding said sequence by detecting specific binding of said polynucleotide primer or probe to said mRNA, thereby detecting the presence of said BARD1 isoform π or π' specific to lung cancer and colorectal cancer, wherein the presence of said BARD1 isoform π or π' specific to lung cancer and colorectal cancer is an indication for lung cancer and/or colorectal cancer.

11. The method of claim 1, wherein said mRNA that encodes said sequence is detected in circulating tumor cells present in said sample.

12. A method for detecting the presence of a BARD1 isoform specific to lung cancer and colorectal cancer, the method comprising the steps of:
obtaining a biological sample from a subject;
detecting in said biological sample autoantibodies specific for a BARD1 isoform π consisting of sequence SEQ ID NO:1 or a sequence having at least 99% homology to SEQ ID NO:1 by performing an immunoassay, wherein said step of performing an immunoassay comprises the steps:
a) providing at least four different antigen peptides selected from the group consisting of SEQ ID NOs:16, 17, 18, 23, 68, 69, 74 and 75, wherein said antigen peptides are immobilized on a solid support,
b) bringing said biological sample into contact with said immobilized solid support, and
c) detecting complexes formed between autoimmune antibodies and antigen peptides, thereby detecting the presence of a BARD1 isoform specific to lung cancer and colorectal cancer,
wherein the presence of said BARD1 isoform π specific to lung cancer and colorectal cancer in a sample from said subject is an indication that said subject is afflicted with lung cancer and/or colorectal cancer, has an increased risk of lung cancer and/or colorectal cancer, a risk of recurrence after a treatment for lung cancer and/or colorectal cancer, and/or is an indication of reduced survival of a patient afflicted with lung cancer.

13. The method of claim 1, wherein said primer or probe is specific for a nucleotide sequence of SEQ ID NO:8 encoding BARD1 isoform n or an nucleotide sequence having 95% homology to SEQ ID NO:8, and for a nucleotide sequence of SEQ ID NO:141 encoding BARD1 isoform n' or an nucleotide sequence having 95% homology to SEQ ID NO:141.

14. The method of claim 1, wherein said primer or probe specifically binds to said mRNA at said deletion junction at an annealing temperature of 56° C. and at salt conditions conducive for binding of a primer or probe to said mRNA.

* * * * *

SEQUENCE LISTING

<160> NUMBER OF SEQ ID NOS: 144

<210> SEQ ID NO 1
<211> LENGTH: 641
<212> TYPE: PRT
<213> ORGANISM: Homo sapiens

<400> SEQUENCE: 1

```
Met Pro Asp Asn Arg Gln Pro Arg Asn Arg Gln Pro Arg Ile Arg Ser
1               5                   10                  15

Gly Asn Glu Pro Arg Ser Ala Pro Ala Met Glu Pro Asp Gly Arg Gly
            20                  25                  30

Ala Trp Ala His Ser Arg Ala Ala Leu Asp Arg Leu Glu Lys Leu Leu
        35                  40                  45

Arg Cys Ser Arg Cys Thr Asn Ile Leu Arg Glu Pro Val Cys Leu Gly
    50                  55                  60

Gly Cys Glu His Ile Phe Cys Ser Asn Cys Val Ser Asp Cys Ile Gly
65                  70                  75                  80

Thr Gly Cys Pro Val Cys Tyr Thr Pro Ala Trp Ile Gln Asp Leu Lys
                85                  90                  95

Ile Asn Arg Gln Leu Asp Ser Met Ile Gln Leu Cys Ser Lys Leu Arg
            100                 105                 110

Asn Leu Leu His Asp Asn Glu Leu Ser Asp Leu Lys Glu Asp Lys Pro
        115                 120                 125

Arg Lys Ser Leu Phe Asn Asp Ala Gly Asn Lys Lys Asn Ser Ile Lys
    130                 135                 140

Met Trp Phe Ser Pro Arg Ser Lys Lys Val Arg Tyr Val Val Ser Lys
145                 150                 155                 160

Ala Ser Val Gln Thr Gln Pro Ala Ile Lys Lys Asp Ala Ser Ala Gln
                165                 170                 175

Gln Asp Ser Tyr Glu Phe Val Ser Pro Ser Pro Ala Asp Val Ser
            180                 185                 190

Glu Arg Ala Lys Lys Ala Ser Ala Arg Ser Gly Lys Lys Gln Lys Lys
        195                 200                 205

Lys Thr Leu Ala Glu Ile Asn Gln Lys Trp Asn Leu Glu Ala Glu Lys
    210                 215                 220

Glu Asp Gly Glu Phe Asp Ser Lys Glu Glu Ser Lys Gln Lys Leu Val
225                 230                 235                 240

Ser Phe Cys Ser Gln Pro Ser Val Ile Ser Ser Pro Gln Ile Asn Gly
                245                 250                 255

Glu Ile Asp Leu Leu Ala Ser Gly Ser Leu Thr Glu Ser Glu Cys Phe
            260                 265                 270

Gly Ser Leu Thr Glu Val Ser Leu Pro Leu Ala Glu Gln Ile Glu Ser
        275                 280                 285

Pro Asp Thr Lys Ser Arg Asn Glu Val Val Thr Pro Ile Lys Gly Asp
    290                 295                 300

Ile Pro Ser Val Glu Tyr Leu Leu Gln Asn Gly Ser Asp Pro Asn Val
305                 310                 315                 320

Lys Asp His Ala Gly Trp Thr Pro Leu His Glu Ala Cys Asn His Gly
                325                 330                 335
```

His Leu Lys Val Val Glu Leu Leu Gln His Lys Ala Leu Val Asn
            340                 345                 350
Thr Thr Gly Tyr Gln Asn Asp Ser Pro Leu His Asp Ala Ala Lys Asn
        355                 360                 365
Gly His Val Asp Ile Val Lys Leu Leu Leu Ser Tyr Gly Ala Ser Arg
    370                 375                 380
Asn Ala Val Asn Ile Phe Gly Leu Arg Pro Val Asp Tyr Thr Asp Asp
385                 390                 395                 400
Glu Ser Met Lys Ser Leu Leu Leu Leu Pro Glu Lys Asn Glu Ser Ser
                405                 410                 415
Ser Ala Ser His Cys Ser Val Met Asn Thr Gly Gln Arg Arg Asp Gly
            420                 425                 430
Pro Leu Val Leu Ile Gly Ser Gly Leu Ser Ser Glu Gln Gln Lys Met
        435                 440                 445
Leu Ser Glu Leu Ala Val Ile Leu Lys Ala Lys Lys Tyr Thr Glu Phe
    450                 455                 460
Asp Ser Thr Val Thr His Val Val Pro Gly Asp Ala Val Gln Ser
465                 470                 475                 480
Thr Leu Lys Cys Met Leu Gly Ile Leu Asn Gly Cys Trp Ile Leu Lys
                485                 490                 495
Phe Glu Trp Val Lys Ala Cys Leu Arg Arg Lys Val Cys Glu Gln Glu
            500                 505                 510
Glu Lys Tyr Glu Ile Pro Glu Gly Pro Arg Arg Ser Arg Leu Asn Arg
        515                 520                 525
Glu Gln Leu Leu Pro Lys Leu Phe Asp Gly Cys Tyr Phe Tyr Leu Trp
    530                 535                 540
Gly Thr Phe Lys His His Pro Lys Asp Asn Leu Ile Lys Leu Val Thr
545                 550                 555                 560
Ala Gly Gly Gly Gln Ile Leu Ser Arg Lys Pro Lys Pro Asp Ser Asp
                565                 570                 575
Val Thr Gln Thr Ile Asn Thr Val Ala Tyr His Ala Arg Pro Asp Ser
            580                 585                 590
Asp Gln Arg Phe Cys Thr Gln Tyr Ile Ile Tyr Glu Asp Leu Cys Asn
        595                 600                 605
Tyr His Pro Glu Arg Val Arg Gln Gly Lys Val Trp Lys Ala Pro Ser
    610                 615                 620
Ser Trp Phe Ile Asp Cys Val Met Ser Phe Glu Leu Leu Pro Leu Asp
625                 630                 635                 640
Ser

<210> SEQ ID NO 2
<211> LENGTH: 633
<212> TYPE: PRT
<213> ORGANISM: Homo sapiens

<400> SEQUENCE: 2

Met Trp Phe Ser Pro Arg Ser Lys Lys Val Arg Tyr Val Val Ser Lys
1               5                   10                  15
Ala Ser Val Gln Thr Gln Pro Ala Ile Lys Lys Asp Ala Ser Ala Gln
            20                  25                  30
Gln Asp Ser Tyr Glu Phe Val Ser Pro Ser Pro Ala Asp Val Ser
        35                  40                  45
Glu Arg Ala Lys Lys Ala Ser Ala Arg Ser Gly Lys Lys Gln Lys Lys
    50                  55                  60

-continued

Lys Thr Leu Ala Glu Ile Asn Gln Lys Trp Asn Leu Glu Ala Glu Lys
 65                  70                  75                  80

Glu Asp Gly Glu Phe Asp Ser Lys Glu Ser Lys Gln Lys Leu Val
             85                  90                  95

Ser Phe Cys Ser Gln Pro Ser Val Ile Ser Pro Gln Ile Asn Gly
            100                 105                 110

Glu Ile Asp Leu Leu Ala Ser Gly Ser Leu Thr Glu Ser Glu Cys Phe
            115                 120                 125

Gly Ser Leu Thr Glu Val Ser Leu Pro Leu Ala Glu Gln Ile Glu Ser
130                 135                 140

Pro Asp Thr Lys Ser Arg Asn Glu Val Val Thr Pro Glu Lys Val Cys
145                 150                 155                 160

Lys Asn Tyr Leu Thr Ser Lys Lys Ser Leu Pro Leu Glu Asn Asn Gly
                165                 170                 175

Lys Arg Gly His His Asn Arg Leu Ser Ser Pro Ile Ser Lys Arg Cys
            180                 185                 190

Arg Thr Ser Ile Leu Ser Thr Ser Gly Asp Phe Val Lys Gln Thr Val
            195                 200                 205

Pro Ser Glu Asn Ile Pro Leu Pro Glu Cys Ser Ser Pro Pro Ser Cys
210                 215                 220

Lys Arg Lys Val Gly Gly Thr Ser Gly Arg Lys Asn Ser Asn Met Ser
225                 230                 235                 240

Asp Glu Phe Ile Ser Leu Ser Pro Gly Thr Pro Ser Thr Leu Ser
                245                 250                 255

Ser Ser Ser Tyr Arg Arg Val Met Ser Ser Pro Ser Ala Met Lys Leu
            260                 265                 270

Leu Pro Asn Met Ala Val Lys Arg Asn His Arg Gly Glu Thr Leu Leu
            275                 280                 285

His Ile Ala Ser Ile Lys Gly Asp Ile Pro Ser Val Glu Tyr Leu Leu
            290                 295                 300

Gln Asn Gly Ser Asp Pro Asn Val Lys Asp His Ala Gly Trp Thr Pro
305                 310                 315                 320

Leu His Glu Ala Cys Asn His Gly His Leu Lys Val Val Glu Leu Leu
                325                 330                 335

Leu Gln His Lys Ala Leu Val Asn Thr Thr Gly Tyr Gln Asn Asp Ser
                340                 345                 350

Pro Leu His Asp Ala Ala Lys Asn Gly His Val Asp Ile Val Lys Leu
            355                 360                 365

Leu Leu Ser Tyr Gly Ala Ser Arg Asn Ala Val Asn Ile Phe Gly Leu
            370                 375                 380

Arg Pro Val Asp Tyr Thr Asp Asp Glu Ser Met Lys Ser Leu Leu Leu
385                 390                 395                 400

Leu Pro Glu Lys Asn Glu Ser Ser Ala Ser His Cys Ser Val Met
                405                 410                 415

Asn Thr Gly Gln Arg Arg Asp Gly Pro Leu Val Leu Ile Gly Ser Gly
            420                 425                 430

Leu Ser Ser Glu Gln Gln Lys Met Leu Ser Glu Leu Ala Val Ile Leu
            435                 440                 445

Lys Ala Lys Lys Tyr Thr Glu Phe Asp Ser Thr Val Thr His Val Val
            450                 455                 460

Val Pro Gly Asp Ala Val Gln Ser Thr Leu Lys Cys Met Leu Gly Ile
465                 470                 475                 480

Leu Asn Gly Cys Trp Ile Leu Lys Phe Glu Trp Val Lys Ala Cys Leu

```
                        485                 490                 495
Arg Arg Lys Val Cys Glu Gln Glu Glu Lys Tyr Glu Ile Pro Glu Gly
                500                 505                 510

Pro Arg Arg Ser Arg Leu Asn Arg Glu Gln Leu Leu Pro Lys Leu Phe
            515                 520                 525

Asp Gly Cys Tyr Phe Tyr Leu Trp Gly Thr Phe Lys His His Pro Lys
        530                 535                 540

Asp Asn Leu Ile Lys Leu Val Thr Ala Gly Gly Gln Ile Leu Ser
545                 550                 555                 560

Arg Lys Pro Lys Pro Asp Ser Asp Val Thr Gln Thr Ile Asn Thr Val
                565                 570                 575

Ala Tyr His Ala Arg Pro Asp Ser Asp Gln Arg Phe Cys Thr Gln Tyr
            580                 585                 590

Ile Ile Tyr Glu Asp Leu Cys Asn Tyr His Pro Glu Arg Val Arg Gln
        595                 600                 605

Gly Lys Val Trp Lys Ala Pro Ser Ser Trp Phe Ile Asp Cys Val Met
    610                 615                 620

Ser Phe Glu Leu Leu Pro Leu Asp Ser
625                 630

<210> SEQ ID NO 3
<211> LENGTH: 300
<212> TYPE: PRT
<213> ORGANISM: Homo sapiens

<400> SEQUENCE: 3

Met Pro Asp Asn Arg Gln Pro Arg Asn Arg Gln Pro Arg Ile Arg Ser
1               5                   10                  15

Gly Asn Glu Pro Arg Ser Ala Pro Ala Met Glu Pro Asp Gly Arg Gly
            20                  25                  30

Ala Trp Ala His Ser Arg Ala Ala Leu Asp Arg Leu Glu Lys Leu Leu
        35                  40                  45

Arg Cys Ser Arg Cys Thr Asn Ile Leu Arg Glu Pro Val Cys Leu Gly
    50                  55                  60

Gly Cys Glu His Ile Phe Cys Ser Asn Cys Val Ser Asp Cys Ile Gly
65                  70                  75                  80

Thr Gly Cys Pro Val Cys Tyr Thr Pro Ala Trp Ile Gln Asp Leu Lys
                85                  90                  95

Ile Asn Arg Gln Leu Asp Ser Met Ile Gln Leu Cys Ser Lys Leu Arg
            100                 105                 110

Asn Leu Leu His Asp Asn Glu Leu Ser Asp Leu Lys Glu Asp Lys Pro
        115                 120                 125

Arg Lys Ser Leu Phe Asn Asp Ala Gly Asn Lys Lys Asn Ser Ile Lys
    130                 135                 140

Met Trp Phe Ser Pro Arg Ser Lys Lys Val Arg Tyr Val Val Ser Lys
145                 150                 155                 160

Ala Ser Val Gln Thr Gln Pro Ala Ile Lys Lys Asp Ala Ser Ala Gln
                165                 170                 175

Gln Asp Ser Tyr Glu Phe Val Ser Pro Ser Pro Pro Ala Asp Val Ser
            180                 185                 190

Glu Arg Ala Lys Lys Ala Ser Ala Arg Ser Gly Lys Lys Gln Lys Lys
        195                 200                 205

Lys Thr Leu Ala Glu Ile Asn Gln Lys Trp Asn Leu Glu Ala Glu Lys
    210                 215                 220
```

```
Glu Asp Gly Glu Phe Asp Ser Lys Glu Glu Ser Lys Gln Lys Leu Val
225                 230                 235                 240

Ser Phe Cys Ser Gln Pro Ser Val Ile Ser Ser Pro Gln Ile Asn Gly
                245                 250                 255

Glu Ile Asp Leu Leu Ala Ser Gly Ser Leu Thr Glu Ser Glu Cys Phe
            260                 265                 270

Gly Ser Leu Thr Glu Val Ser Leu Pro Leu Ala Glu Gln Ile Glu Ser
        275                 280                 285

Pro Asp Thr Lys Ser Arg Asn Glu Val Val Thr Pro
    290                 295                 300

<210> SEQ ID NO 4
<211> LENGTH: 300
<212> TYPE: PRT
<213> ORGANISM: Homo sapiens

<400> SEQUENCE: 4

Met Trp Phe Ser Pro Arg Ser Lys Lys Val Arg Tyr Val Val Ser Lys
1               5                   10                  15

Ala Ser Val Gln Thr Gln Pro Ala Ile Lys Lys Asp Ala Ser Ala Gln
            20                  25                  30

Gln Asp Ser Tyr Glu Phe Val Ser Pro Ser Pro Ala Asp Val Ser
        35                  40                  45

Glu Arg Ala Lys Lys Ala Ser Ala Arg Ser Gly Lys Lys Gln Lys Lys
50                  55                  60

Lys Thr Leu Ala Glu Ile Asn Gln Lys Trp Asn Leu Glu Ala Glu Lys
65                  70                  75                  80

Glu Asp Gly Glu Phe Asp Ser Lys Glu Glu Ser Lys Gln Lys Leu Val
                85                  90                  95

Ser Phe Cys Ser Gln Pro Ser Val Ile Ser Ser Pro Gln Ile Asn Gly
            100                 105                 110

Glu Ile Asp Leu Leu Ala Ser Gly Ser Leu Thr Glu Ser Glu Cys Phe
        115                 120                 125

Gly Ser Leu Thr Glu Val Ser Leu Pro Leu Ala Glu Gln Ile Glu Ser
    130                 135                 140

Pro Asp Thr Lys Ser Arg Asn Glu Val Val Thr Pro Glu Lys Val Cys
145                 150                 155                 160

Lys Asn Tyr Leu Thr Ser Lys Lys Ser Leu Pro Leu Glu Asn Asn Gly
                165                 170                 175

Lys Arg Gly His His Asn Arg Leu Ser Ser Pro Ile Ser Lys Arg Cys
            180                 185                 190

Arg Thr Ser Ile Leu Ser Thr Ser Gly Asp Phe Val Lys Gln Thr Val
        195                 200                 205

Pro Ser Glu Asn Ile Pro Leu Pro Glu Cys Ser Ser Pro Pro Ser Cys
    210                 215                 220

Lys Arg Lys Val Gly Gly Thr Ser Gly Arg Lys Asn Ser Asn Met Ser
225                 230                 235                 240

Asp Glu Phe Ile Ser Leu Ser Pro Gly Thr Pro Pro Ser Thr Leu Ser
                245                 250                 255

Ser Ser Ser Tyr Arg Arg Val Met Ser Ser Pro Ser Ala Met Lys Leu
            260                 265                 270

Leu Pro Asn Met Ala Val Lys Arg Asn His Arg Gly Glu Thr Leu Leu
        275                 280                 285

His Ile Ala Ser Ile Lys Gly Asp Ile Pro Ser Val
    290                 295                 300
```

<210> SEQ ID NO 5
<211> LENGTH: 680
<212> TYPE: PRT
<213> ORGANISM: Homo sapiens

<400> SEQUENCE: 5

Met Val Ala Val Pro Gly Pro Thr Val Ala Pro Arg Ser Thr Ala Trp
1               5                   10                  15

Arg Ser Cys Cys Ala Ala Arg Val Asp Leu Lys Glu Asp Lys Pro Arg
            20                  25                  30

Lys Ser Leu Phe Asn Asp Ala Gly Asn Lys Lys Asn Ser Ile Lys Met
        35                  40                  45

Trp Phe Ser Pro Arg Ser Lys Lys Val Arg Tyr Val Val Ser Lys Ala
    50                  55                  60

Ser Val Gln Thr Gln Pro Ala Ile Lys Lys Asp Ala Ser Ala Gln Gln
65                  70                  75                  80

Asp Ser Tyr Glu Phe Val Ser Pro Ser Pro Ala Asp Val Ser Glu
                85                  90                  95

Arg Ala Lys Lys Ala Ser Ala Arg Ser Gly Lys Lys Gln Lys Lys Lys
            100                 105                 110

Thr Leu Ala Glu Ile Asn Gln Lys Trp Asn Leu Glu Ala Glu Lys Glu
        115                 120                 125

Asp Gly Glu Phe Asp Ser Lys Glu Glu Ser Lys Gln Lys Leu Val Ser
    130                 135                 140

Phe Cys Ser Gln Pro Ser Val Ile Ser Ser Pro Gln Ile Asn Gly Glu
145                 150                 155                 160

Ile Asp Leu Leu Ala Ser Gly Ser Leu Thr Glu Ser Glu Cys Phe Gly
                165                 170                 175

Ser Leu Thr Glu Val Ser Leu Pro Leu Ala Glu Gln Ile Glu Ser Pro
            180                 185                 190

Asp Thr Lys Ser Arg Asn Glu Val Val Thr Pro Glu Lys Val Cys Lys
        195                 200                 205

Asn Tyr Leu Thr Ser Lys Lys Ser Leu Pro Leu Glu Asn Asn Gly Lys
    210                 215                 220

Arg Gly His His Asn Arg Leu Ser Ser Pro Ile Ser Lys Arg Cys Arg
225                 230                 235                 240

Thr Ser Ile Leu Ser Thr Ser Gly Asp Phe Val Lys Gln Thr Val Pro
                245                 250                 255

Ser Glu Asn Ile Pro Leu Pro Glu Cys Ser Ser Pro Ser Cys Lys
            260                 265                 270

Arg Lys Val Gly Gly Thr Ser Gly Arg Lys Asn Ser Asn Met Ser Asp
        275                 280                 285

Glu Phe Ile Ser Leu Ser Pro Gly Thr Pro Ser Thr Leu Ser Ser
    290                 295                 300

Ser Ser Tyr Arg Gln Val Met Ser Ser Pro Ser Ala Met Lys Leu Leu
305                 310                 315                 320

Pro Asn Met Ala Val Lys Arg Asn His Arg Gly Glu Thr Leu Leu His
                325                 330                 335

Ile Ala Ser Ile Lys Gly Asp Ile Pro Ser Val Glu Tyr Leu Leu Gln
            340                 345                 350

Asn Gly Ser Asp Pro Asn Val Lys Asp His Ala Gly Trp Thr Pro Leu
        355                 360                 365

His Glu Ala Cys Asn His Gly His Leu Lys Val Val Glu Leu Leu Leu

-continued

```
                370                 375                 380
Gln His Lys Ala Leu Val Asn Thr Thr Gly Tyr Gln Asn Asp Ser Pro
385                 390                 395                 400

Leu His Asp Ala Ala Lys Asn Gly His Val Asp Ile Val Lys Leu Leu
                405                 410                 415

Leu Ser Tyr Gly Ala Ser Arg Asn Ala Val Asn Ile Phe Gly Leu Arg
            420                 425                 430

Pro Val Asp Tyr Thr Asp Glu Ser Met Lys Ser Leu Leu Leu Leu
            435                 440                 445

Pro Glu Lys Asn Glu Ser Ser Ser Ala Ser His Cys Ser Val Met Asn
        450                 455                 460

Thr Gly Gln Arg Arg Asp Gly Pro Leu Val Leu Ile Gly Ser Gly Leu
465                 470                 475                 480

Ser Ser Glu Gln Gln Lys Met Leu Ser Glu Leu Ala Val Ile Leu Lys
                485                 490                 495

Ala Lys Lys Tyr Thr Glu Phe Asp Ser Thr Val Thr His Val Val Val
            500                 505                 510

Pro Gly Asp Ala Val Gln Ser Thr Leu Lys Cys Met Leu Gly Ile Leu
            515                 520                 525

Asn Gly Cys Trp Ile Leu Lys Phe Glu Trp Val Lys Ala Cys Leu Arg
        530                 535                 540

Arg Lys Val Cys Glu Gln Glu Lys Tyr Glu Ile Pro Glu Gly Pro
545                 550                 555                 560

Arg Arg Ser Arg Leu Asn Arg Glu Gln Leu Leu Pro Lys Leu Phe Asp
                565                 570                 575

Gly Cys Tyr Phe Tyr Leu Trp Gly Thr Phe Lys His His Pro Lys Asp
            580                 585                 590

Asn Leu Ile Lys Leu Val Thr Ala Gly Gly Gln Ile Leu Ser Arg
            595                 600                 605

Lys Pro Lys Pro Asp Ser Asp Val Thr Gln Thr Ile Asn Thr Val Ala
        610                 615                 620

Tyr His Ala Arg Pro Asp Ser Asp Gln Arg Phe Cys Thr Gln Tyr Ile
625                 630                 635                 640

Ile Tyr Glu Asp Leu Cys Asn Tyr His Pro Glu Arg Val Arg Gln Gly
                645                 650                 655

Lys Val Trp Lys Ala Pro Ser Ser Trp Phe Ile Asp Cys Val Met Ser
            660                 665                 670

Phe Glu Leu Leu Pro Leu Asp Ser
            675                 680

<210> SEQ ID NO 6
<211> LENGTH: 307
<212> TYPE: PRT
<213> ORGANISM: Homo sapiens

<400> SEQUENCE: 6

Met Pro Asp Asn Arg Gln Pro Arg Asn Arg Gln Pro Arg Ile Arg Ser
1               5                   10                  15

Gly Asn Glu Pro Arg Ser Ala Ser Ala Met Glu Pro Asp Gly Arg Gly
                20                  25                  30

Ala Trp Ala His Ser Arg Ala Ala Leu Asp Arg Leu Glu Lys Leu Leu
            35                  40                  45

Arg Cys Ser Arg Cys Asn Ile Phe Gly Leu Arg Pro Val Asp Tyr Thr
        50                  55                  60
```

Asp Asp Glu Ser Met Lys Ser Leu Leu Leu Pro Glu Lys Asn Glu
65                  70                  75                  80

Ser Ser Ser Ala Ser His Cys Ser Val Met Asn Thr Gly Gln Arg Arg
                85                  90                  95

Asp Gly Pro Leu Val Leu Ile Gly Ser Gly Leu Ser Ser Glu Gln Gln
            100                 105                 110

Lys Met Leu Ser Glu Leu Ala Val Ile Leu Lys Ala Lys Lys Tyr Thr
            115                 120                 125

Glu Phe Asp Ser Thr Val Thr His Val Val Pro Gly Asp Ala Val
130                 135                 140

Gln Ser Thr Leu Lys Cys Met Leu Gly Ile Leu Asn Gly Cys Trp Ile
145                 150                 155                 160

Leu Lys Phe Glu Trp Val Lys Ala Cys Leu Arg Arg Lys Val Cys Glu
                165                 170                 175

Gln Glu Glu Lys Tyr Glu Ile Pro Glu Gly Pro Arg Arg Ser Arg Leu
            180                 185                 190

Asn Arg Glu Gln Leu Leu Pro Lys Leu Phe Asp Gly Cys Tyr Phe Tyr
        195                 200                 205

Leu Trp Gly Thr Phe Lys His His Pro Lys Asp Asn Leu Ile Lys Leu
210                 215                 220

Val Thr Ala Gly Gly Gly Gln Ile Leu Ser Arg Lys Pro Lys Pro Asp
225                 230                 235                 240

Ser Asp Val Thr Gln Thr Ile Asn Thr Val Ala Tyr His Ala Arg Pro
                245                 250                 255

Asp Ser Asp Gln Arg Phe Cys Thr Gln Tyr Ile Ile Tyr Glu Asp Leu
            260                 265                 270

Cys Asn Tyr His Pro Glu Arg Val Arg Gln Gly Lys Val Trp Lys Ala
        275                 280                 285

Pro Ser Ser Trp Phe Ile Asp Cys Val Met Ser Phe Glu Leu Leu Pro
290                 295                 300

Leu Asp Ser
305

<210> SEQ ID NO 7
<211> LENGTH: 345
<212> TYPE: PRT
<213> ORGANISM: Homo sapiens

<400> SEQUENCE: 7

Met Thr Met Ser Cys Gln Gly Asp Ile Pro Ser Val Glu Tyr Leu Leu
1               5                   10                  15

Gln Asn Gly Ser Asp Pro Asn Val Lys Asp His Ala Gly Trp Thr Pro
            20                  25                  30

Leu His Glu Ala Cys Asn His Gly His Leu Glu Val Val Glu Leu Leu
        35                  40                  45

Leu Gln His Lys Ala Leu Val Asn Thr Thr Gly Tyr Gln Asn Asp Ser
    50                  55                  60

Pro Leu His Asp Ala Ala Lys Asn Gly His Met Asp Ile Val Lys Leu
65                  70                  75                  80

Leu Leu Ser Tyr Gly Ala Ser Arg Asn Ala Val Asn Ile Phe Gly Leu
                85                  90                  95

Arg Pro Val Asp Tyr Thr Asp Asp Glu Ser Met Lys Ser Leu Leu Leu
            100                 105                 110

Leu Pro Glu Lys Asn Glu Ser Ser Ser Ala Ser His Cys Ser Val Met
        115                 120                 125

Asn Thr Gly Gln Arg Arg Asp Gly Pro Leu Val Leu Ile Gly Ser Gly
130                 135                 140

Leu Ser Ser Glu Gln Gln Lys Met Leu Ser Glu Ala Val Ile Leu
145                 150                 155                 160

Lys Ala Lys Tyr Thr Glu Phe Asp Ser Thr Val Thr His Val Val
                165                 170                 175

Val Pro Gly Asp Ala Val Gln Ser Thr Leu Lys Cys Met Leu Gly Ile
            180                 185                 190

Leu Asn Gly Cys Trp Ile Leu Lys Phe Glu Trp Val Lys Ala Cys Leu
        195                 200                 205

Arg Arg Lys Val Cys Glu Gln Glu Lys Tyr Glu Ile Pro Glu Gly
210                 215                 220

Pro Arg Arg Ser Arg Leu Asn Arg Glu Gln Leu Leu Pro Lys Leu Phe
225                 230                 235                 240

Asp Gly Cys Tyr Phe Tyr Leu Trp Gly Thr Phe Lys His His Pro Lys
                245                 250                 255

Asp Asn Leu Ile Lys Leu Val Thr Ala Gly Gly Gly Gln Ile Leu Ser
                260                 265                 270

Arg Lys Pro Lys Pro Asp Ser Asp Val Thr Gln Thr Ile Asn Thr Val
        275                 280                 285

Ala Tyr His Ala Arg Pro Asp Ser Asp Gln Arg Phe Cys Thr Gln Tyr
290                 295                 300

Ile Ile Tyr Glu Asp Leu Cys Asn Tyr His Pro Glu Arg Val Arg Gln
305                 310                 315                 320

Gly Lys Val Trp Lys Ala Pro Ser Ser Trp Phe Ile Asp Cys Val Met
                325                 330                 335

Ser Phe Glu Leu Leu Pro Leu Asp Ser
                340                 345

<210> SEQ ID NO 8
<211> LENGTH: 2202
<212> TYPE: DNA
<213> ORGANISM: Homo sapiens

<400> SEQUENCE: 8

```
cctctggcgg cccgccgtcc cagacgcggg aagagcttgg ccggtttcga gtcgctggcc      60
tgcagcttcc ctgtggtttc ccgaggcttc cttgcttccc gctctgcgag gagccttca     120 tccgaaggcg ggacgatgcc ggataatcgg cagccgagga accggcagcc gaggatccgc    180
tccgggaacg agcctcgttc cgcgcccgcc atggaaccgg atggtcgcgg tgcctgggcc    240
cacagtcgcg ccgcgctcga ccgcctggag aagctgctgc gctgctcgcg ttgtactaac    300
attctgagag agcctgtgtg tttaggagga tgtgagcaca tcttctgtag taattgtgta    360
agtgactgca ttggaactgg atgtccagtg tgttacaccc cggcctggat acaagacttg    420
aagataaata gacaactgga cagcatgatt caactttgta gtaagcttcg aaatttgcta    480
catgacaatg agctgtcaga tttgaaagaa gataaaccta ggaaaagttt gtttaatgat    540
gcaggaaaca agaagaattc aattaaaatg tggtttagcc ctcgaagtaa gaaagtcaga    600
tatgttgtga gtaaagcttc agtgcaaacc cagcctgcaa taaaaaaga tgcaagtgct    660 cagcaagact catatgaatt tgtttcccca agtcctcctg cagatgtttc tgagagggct    720
aaaaaggctt ctgcaagatc tggaaaaaag caaaaaaaga aactttagc tgaaatcaac    780 caaaaatgga atttagaggc agaaaaagaa gatggtgaat ttgactccaa agaggaatct    840
```

```
aagcaaaagc tggtatcctt ctgtagccaa ccatctgtta tctccagtcc tcagataaat    900
ggtgaaatag acttactagc aagtggctcc ttgacagaat ctgaatgttt tggaagttta    960
actgaagtct ctttaccatt ggctgagcaa atagagtctc cagacactaa gagcaggaat   1020
gaagtagtga ctcctattaa gggcgacata ccttctgttg aataccttt acaaaatgga    1080 agtgatccaa atgttaaaga ccatgctgga tggacaccat tgcatgaagc ttgcaatcat   1140
gggcacctga aggtagtgga attattgctc cagcataagg cattggtgaa caccaccggg   1200
tatcaaaatg actcaccact tcacgatgca gccaagaatg ggcatgtgga tatagtcaag   1260
ctgttacttt cctatggagc ctccagaaat gctgttaata tatttggtct gcggcctgtc   1320
gattatacag atgatgaaag tatgaaatcg ctattgctgc taccagagaa gaatgaatca   1380
tcctcagcta gccactgctc agtaatgaac actgggcagc gtagggatgg acctcttgta   1440
cttataggca gtgggctgtc ttcagaacaa cagaaaatgc tcagtgagct tgcagtaatt   1500
cttaaggcta aaaatatac tgagtttgac agtacagtaa ctcatgttgt tgttcctggt    1560
gatgcagttc aaagtacctt gaagtgtatg cttgggattc tcaatggatg ctggattcta   1620
aaatttgaat gggtaaaagc atgtctacga agaaaagtat gtgaacagga gaaaagtat    1680 gaaattcctg aaggtccacg cagaagcagg ctcaacagag aacagctgtt gccaaagctg   1740
tttgatggat gctacttcta tttgtgggga accttcaaac accatccaaa ggacaacctt   1800
attaagctcg tcactgcagg tggggggccag atcctcagta gaaagcccaa gccagacagt   1860
gacgtgactc agaccatcaa tacagtcgca taccatgcga gacccgattc tgatcagcgc   1920
ttctgcacac agtatatcat ctatgaagat tgtgtaatt atcacccaga gagggttcgg    1980
cagggcaaag tctggaaggc tccttcgagc tggtttatag actgtgtgat gtcctttgag   2040
ttgcttcctc ttgacagctg aatattatac cagatgaaca tttcaaattg aatttgcacg   2100
gtttgtgaga gcccagtcat tgtactgttt ttaatgttca cattttttaca aataggtaga   2160 gtcattcata tttgtctttg aatcaaaaaa aaaaaaaaaa aa                      2202
```

<210> SEQ ID NO 9
<211> LENGTH: 2461
<212> TYPE: DNA
<213> ORGANISM: Homo sapiens

<400> SEQUENCE: 9

```
cctctggcgg cccgccgtcc cagacgcggg aagagcttgg ccggtttcga gtcgctggcc     60
tgcagcttcc ctgtggtttc ccgaggcttc cttgcttccc gctctgcgag gagcctttca    120
tccgaaggcg ggacgatgcc ggataatcgg cagccgagga accggcagcc gaggatccgc    180
tccgggaacg agcctcgttc cgcgcccgcc atggaaccgg atggtcgcgg tgcctgggcc    240
cacagtcgcg ccgcgctcga ccgcctggag aagctgctgc gctgctcgcg ttgtactaac    300
attctgagag agcctgtgtg tttaggagga tgtgagcaca tcttctgtag atttgaaaga    360
agataaacct aggaaaagtt tgtttaatga tgcaggaaac aagaagaatt caattaaaat    420
gtggtttagc cctcgaagta agaaagtcag atatgttgtg agtaaagctt cagtgcaaac    480
ccagcctgca ataaaaaaag atgcaagtgc tcagcaagac tcatatgaat tgtttcccc     540 aagtcctcct gcagatgttt ctgagagggc taaaaaggct tctgcaagat ctggaaaaaa    600
gcaaaaaaag aaaactttag ctgaaatcaa ccaaaaatgg aatttagagg cagaaaaaga    660
agatggtgaa tttgactcca agaggaatc taagcaaaag ctggtatcct tctgtagcca     720
accatctgtt atctccagtc ctcagataaa tggtgaaata gacttactag caagtggctc    780
```

```
cttgacagaa tctgaatgtt ttggaagttt aactgaagtc tctttaccat tggctgagca      840
aatagagtct ccagacacta agagcaggaa tgaagtagtg actcctgaga aggtctgcaa      900
aaattatctt acatctaaga aatctttgcc attagaaaat aatggaaaac gtggccatca      960
caatagactt tccagtccca tttctaagag atgtagaacc agcattctga gcaccagtgg     1020
agattttgtt aagcaaacgg tgccctcaga aaatatacca ttgcctgaat gttcttcacc     1080
accttcatgc aaacgtaaag ttggtggtac atcaggagg aaaaacagta acatgtccga      1140
tgaattcatt agtctttcac caggtacacc accttctaca ttaagtagtt caagttacag     1200
gcgagtgatg tctagtccct cagcaatgaa gctgttgccc aatatggctg tgaaaagaaa     1260
tcatagagga gagactttgc tccatattgc ttctattaag ggcgacatac cttctgttga     1320 ataccttta caaatggaa gtgatccaaa tgttaaagac catgctggat ggacaccatt       1380
gcatgaagct tgcaatcatg ggcacctgaa ggtagtggaa ttattgctcc agcataaggc     1440
attggtgaac accaccgggt atcaaaatga ctcaccactt cacgatgcag ccaagaatgg     1500
gcatgtggat atagtcaagc tgttactttc ctatggagcc tccagaaatg ctgttaatat     1560
atttggtctg cggcctgtcg attatacaga tgatgaaagt atgaaatcgc tattgctgct     1620
accagagaag aatgaatcat cctcagctag ccactgctca gtaatgaaca ctgggcagcg     1680
tagggatgga cctcttgtac ttataggcag tgggctgtct tcagaacaac agaaaatgct     1740
cagtgagctt gcagtaattc ttaaggctaa aaaatatact gagtttgaca gtacagtaac     1800
tcatgttgtt gttcctggtg atgcagttca aagtaccttg aagtgtatgc ttgggattct     1860
caatggatgc tggattctaa aatttgaatg ggtaaaagca tgtctacgaa gaaaagtatg     1920
tgaacaggaa gaaaagtatg aaattcctga aggtccacgc agaagcaggc tcaacagaga     1980
acagctgttg ccaaagctgt tgatggatg ctacttctat ttgtggggaa ccttcaaaca      2040
ccatccaaag acaaccttta ttaagctcgt cactgcaggt gggggccaga tcctcagtag     2100
aaagcccaag ccagacagtg acgtgactca gaccatcaat acagtcgcat accatgcgag     2160
acccgattct gatcagcgct tctgcacaca gtatatcatc tatgaagatt tgtgtaatta     2220
tcacccagag agggttcggc agggcaaagt ctggaaggct ccttcgagct ggtttataga     2280
ctgtgtgatg tcctttgagt tgcttcctct tgacagctga atattatacc agatgaacat     2340
ttcaaattga atttgcacgg tttgtgagag cccagtcatt gtactgtttt taatgttcac     2400 attttacaa ataggtagag tcattcatat ttgtctttga atcaaaaaaa aaaaaaaaa      2460 a                                                                    2461

<210> SEQ ID NO 10
<211> LENGTH: 2324
<212> TYPE: DNA
<213> ORGANISM: Homo sapiens

<400> SEQUENCE: 10
cagcttccct gtggtttccc gaggcttcct tgcttcccgc tctgcgagga gcctttcatc       60
cgaaggcggg acgatgccgg ataatcggca gccgaggaac cggcagccga ggatccgctc      120
cgggaacgag cctcgttccg cgcccgccat ggaaccggat ggtcgcggtg cctgggccca      180
cagtcgcgcc gcgctcgacc gcctggagaa gctgctgcgc tgctcgcgtt gatttgaaag      240
aagataaacc taggaaaagt ttgtttaatg atgcaggaaa caagaagaat tcaattaaaa      300
tgtggtttag ccctcgaagt aagaaagtca gatatgttgt gagtaaagct tcagtgcaaa      360
```

| | |
|---|---|
| cccagcctgc aataaaaaaa gatgcaagtg ctcagcaaga ctcatatgaa tttgtttccc | 420 |
| caagtcctcc tgcagatgtt tctgagaggg ctaaaaaggc ttctgcaaga tctggaaaaa | 480 |
| agcaaaaaaa gaaaacttta gctgaaatca accaaaaatg gaatttagag gcagaaaaag | 540 |
| aagatggtga atttgactcc aaagaggaat ctaagcaaaa gctggtatcc ttctgtagcc | 600 |
| aaccatctgt tatctccagt cctcagataa atggtgaaat agacttacta gcaagtggct | 660 |
| ccttgacaga atctgaatgt tttggaagtt taactgaagt ctcttttacca ttggctgagc | 720 |
| aaatagagtc tccagacact aagagcagga atgaagtagt gactcctgag aaggtctgca | 780 |
| aaaattatct tacatctaag aaatctttgc cattagaaaa taatgaaaaa cgtggccatc | 840 |
| acaatagact ttccagtccc atttctaaga gatgtagaac cagcattctg agcaccagtg | 900 |
| gagattttgt taagcaaacc gtgccctcag aaaatatacc attgcctgaa tgttcttcac | 960 |
| caccttcatg caaacgtaaa gttggtggta catcagggag gaaaaacagt aacatgtccg | 1020 |
| atgaattcat tagtctttca ccaggtacac caccttctac attaagtagt tcaagttaca | 1080 |
| ggcaagtgat gtctagtccc tcagcaatga agctgttgcc caatatggct gtgaaaagaa | 1140 |
| atcatagagg agagactttg ctccatattg cttctattaa gggcgacata ccttctgttg | 1200 |
| aatacctttt acaaaatgga agtgatccaa atgttaaaga ccatgctgga tggacaccat | 1260 |
| tgcatgaagc ttgcaatcat gggcacctga aggtagtgga attattgctc cagcataagg | 1320 |
| cattggtgaa caccaccggg tatcaaaatg actcaccact tcacgatgca gccaagaatg | 1380 |
| ggcacgtgga tatagtcaag ctgttacttt cctatggagc ctccagaaat gctgttaata | 1440 |
| tatttggtct gcggcctgtc gattatacag atgatgaaaa tatgaaatcg ctattgctgc | 1500 |
| taccagagaa gaatgaatca tcctcagcta gccactgctc agtaatgaac actgggcagc | 1560 |
| gtagggatgg aacctcttgta cttataggca gtgggctgtc ttcagaacaa cagaaaatgc | 1620 |
| tcagtgagct tgcagtaatt cttaaggcta aaaaatatac tgagtttgac agtacagtaa | 1680 |
| ctcatgttgt tgttcctggt gatgcagttc aaagtacctt gaagtgtatg cttgggattc | 1740 |
| tcaatggatg ctggattcta aaatttgaat gggtaaaagc atgtctacga agaaaagtat | 1800 |
| gtgaacagga agaaaagtat gaaattcctg aaggtccacg cagaagcagg ctcaacagag | 1860 |
| aacagctgtt gccaaagctg tttgatggat gctacttcta tttgtgggga accttcaaac | 1920 |
| accatccaaa ggacaacctt attaagctcg tcactgcagg tggggccag atcctcagta | 1980 |
| gaaagcccaa gccagacagt gacgtgactc agaccatcaa tacagtcgca taccatgcga | 2040 |
| gacccgattc tgatcagcgc ttctgcacac agtatatcat ctatgaagat tgtgtaattt | 2100 |
| atcacccaga gagggttcgg cagggcaaag tctggaaggc tccttcgagc tggtttatag | 2160 |
| actgtgtgat gtcctttgag ttgcttcctc ttgacagctg aatattatac cagatgaaca | 2220 |
| tttcaaattg aatttgcacg gtttgtgaga gcccagtcat tgtactgttt ttaatgttca | 2280 |
| cattttaca aataggtaga gtcattcata tttgtctttg aatc | 2324 |

<210> SEQ ID NO 11
<211> LENGTH: 953
<212> TYPE: DNA
<213> ORGANISM: Homo sapiens

<400> SEQUENCE: 11

| | |
|---|---|
| gaggagcctt tcatccgaag gcgggacgat gccggataat cggcagccga ggaaccggca | 60 |
| gccgaggatc cgctccggga acgagcctcg ttccgcgtcc gccatggaac cggatggtcg | 120 |
| cggtgcctgg gcccacagtc gcgccgcgct cgaccgcctg gagaagctgc tgcgctgctc | 180 |

```
gcgttgtaat atatttggtc tgcggcctgt cgattataca gatgatgaaa gtatgaaatc      240
gctattgctg ctaccagaga agaatgaatc atcctcagct agccactgct cagtaatgaa      300
cactgggcag cgtagggatg gacctcttgt acttataggc agtgggctgt cttcagaaca      360
acagaaaatg ctcagtgagc ttgcagtaat tcttaaggct aaaaaatata ctgagtttga      420
cagtacagta actcatgttg ttgttcctgg tgatgcagtt caaagtacct gaagtgtat       480 gcttgggatt ctcaatggat gctggattct aaaatttgaa tgggtaaaag catgtctacg      540
aagaaaagta tgtgaacagg aagaaaagta tgaaattcct gaaggtccac gcagaagcag      600
gctcaacaga gaacagctgt tgccaaagct gtttgatgga tgctacttct atttgtgggg      660
aaccttcaaa caccatccaa aggacaacct tattaagctc gtcactgcag gtggggccca      720
gatcctcagt agaaagccca agccagacag tgacgtgact cagaccatca atacagtcgc      780
ataccatgcg agacccgatt ctgatcagcg cttctgcaca cagtatatca tctatgaaga      840
tttgtgtaat tatcacccag agagggttcg gcagggcaaa gtctggaagg ctccttcgag      900
ctggtttata gactgtgtga tgtcctttga gttgcttcct cttgacagct gaa            953
```

<210> SEQ ID NO 12
<211> LENGTH: 1037
<212> TYPE: DNA
<213> ORGANISM: Homo sapiens

<400> SEQUENCE: 12

```
atgacaatga gctgtcaggg cgacatacct tctgttgaat accttttaca aaatggaagt       60
gatccaaatg ttaaagacca tgctggatgg acaccattgc atgaagcttg caatcatggg      120
cacctggagg tagtggaatt attgctccag cataaggcat tggtgaacac caccgggtat      180
caaaatgact caccacttca cgatgcagcc aagaatgggc acatggatat agtcaagctg      240
ttactttcct atggagcctc cagaaatgct gttaatatat ttggtctgcg gcctgtcgat      300
tatacagatg atgaaagtat gaaatcgcta ttgctgctac cagagaagaa tgaatcatcc      360
tcagctagcc actgctcagt aatgaacact gggcagcgta gggatggacc tcttgtactt      420
ataggcagtg ggctgtcttc agaacaacag aaaatgctca gtgagcttgc agtaattctt      480
aaggctaaaa aatatactga gtttgacagt acagtaactc atgttgttgt tcctggtgat      540
gcagttcaaa gtaccttgaa gtgtatgctt gggattctca atggatgctg gattctaaaa      600
tttgaatggg taaaagcatg tctacgaaga aaagtatgtg aacaggaaga aaagtatgaa      660
attcctgaag gtccacgcag aagcaggctc aacagagaac agctgttgcc aaagctgttt      720
gatggatgct acttctattt gtggggaacc ttcaaacacc atccaaagga caaccttatt      780
aagctcgtca ctgcaggtgg gggccagatc ctcagtagaa agcccaagcc agacagtgac      840
gtgactcaga ccatcaatac agtcgcatac catgcgagac ccgattctga tcagcgcttc      900
tgcacacagt atatcatcta tgaagatttg tgtaattatc acccagagag ggttcggcag      960
ggcaaagtct ggaaggctcc ttcgagctgg tttatagact gtgtgatgtc ctttgagttg     1020
cttcctcttg acagctg                                                    1037
```

<210> SEQ ID NO 13
<211> LENGTH: 15
<212> TYPE: PRT
<213> ORGANISM: Artificial
<220> FEATURE:
<223> OTHER INFORMATION: synthetic peptide

```
<400> SEQUENCE: 13

Met Pro Asp Asn Arg Gln Pro Arg Asn Arg Gln Pro Arg Ile Pro
1               5                   10                  15

<210> SEQ ID NO 14
<211> LENGTH: 11
<212> TYPE: PRT
<213> ORGANISM: Artificial
<220> FEATURE:
<223> OTHER INFORMATION: synthetic peptide

<400> SEQUENCE: 14

Met Glu Pro Asp Gly Arg Gly Ala Trp Ala His
1               5                   10

<210> SEQ ID NO 15
<211> LENGTH: 12
<212> TYPE: PRT
<213> ORGANISM: Artificial
<220> FEATURE:
<223> OTHER INFORMATION: synthetic peptide

<400> SEQUENCE: 15

Asp Arg Leu Glu Lys Leu Leu Arg Cys Ser Arg Cys
1               5                   10

<210> SEQ ID NO 16
<211> LENGTH: 14
<212> TYPE: PRT
<213> ORGANISM: Artificial
<220> FEATURE:
<223> OTHER INFORMATION: synthetic peptide

<400> SEQUENCE: 16

Arg Cys Ser Arg Cys Thr Asn Ile Leu Arg Glu Pro Val Cys
1               5                   10

<210> SEQ ID NO 17
<211> LENGTH: 11
<212> TYPE: PRT
<213> ORGANISM: Artificial
<220> FEATURE:
<223> OTHER INFORMATION: synthetic peptide

<400> SEQUENCE: 17

Cys Leu Gly Gly Cys Glu His Ile Phe Cys Ser
1               5                   10

<210> SEQ ID NO 18
<211> LENGTH: 11
<212> TYPE: PRT
<213> ORGANISM: Artificial
<220> FEATURE:
<223> OTHER INFORMATION: synthetic peptide

<400> SEQUENCE: 18

His Ile Phe Cys Ser Asn Cys Val Ser Asp Cys
1               5                   10

<210> SEQ ID NO 19
<211> LENGTH: 12
<212> TYPE: PRT
<213> ORGANISM: Artificial
<220> FEATURE:
<223> OTHER INFORMATION: synthetic peptide

<400> SEQUENCE: 19
```

```
Gly Thr Gly Cys Pro Val Cys Tyr Thr Pro Ala Trp
1               5                   10
```

<210> SEQ ID NO 20
<211> LENGTH: 14
<212> TYPE: PRT
<213> ORGANISM: Artificial
<220> FEATURE:
<223> OTHER INFORMATION: synthetic peptide

<400> SEQUENCE: 20

```
Pro Ala Trp Ile Gln Asp Leu Lys Ile Asn Arg Gln Leu Asp
1               5                   10
```

<210> SEQ ID NO 21
<211> LENGTH: 14
<212> TYPE: PRT
<213> ORGANISM: Artificial
<220> FEATURE:
<223> OTHER INFORMATION: synthetic peptide

<400> SEQUENCE: 21

```
Cys Ser Lys Leu Arg Asn Leu Leu His Asp Asn Glu Leu Ser
1               5                   10
```

<210> SEQ ID NO 22
<211> LENGTH: 11
<212> TYPE: PRT
<213> ORGANISM: Artificial
<220> FEATURE:
<223> OTHER INFORMATION: synthetic peptide

<400> SEQUENCE: 22

```
Asp Asn Glu Leu Ser Asp Leu Lys Glu Asp Lys
1               5                   10
```

<210> SEQ ID NO 23
<211> LENGTH: 10
<212> TYPE: PRT
<213> ORGANISM: Artificial
<220> FEATURE:
<223> OTHER INFORMATION: synthetic peptide

<400> SEQUENCE: 23

```
Asp Ala Gly Asn Lys Lys Asn Ser Ile Lys
1               5                   10
```

<210> SEQ ID NO 24
<211> LENGTH: 12
<212> TYPE: PRT
<213> ORGANISM: Artificial
<220> FEATURE:
<223> OTHER INFORMATION: synthetic peptide

<400> SEQUENCE: 24

```
Met Trp Phe Ser Pro Arg Ser Lys Lys Val Arg Tyr
1               5                   10
```

<210> SEQ ID NO 25
<211> LENGTH: 12
<212> TYPE: PRT
<213> ORGANISM: Artificial
<220> FEATURE:
<223> OTHER INFORMATION: synthetic peptide

<400> SEQUENCE: 25

Arg Tyr Val Val Ser Lys Ala Ser Val Gln Thr Gln
1               5                   10

<210> SEQ ID NO 26
<211> LENGTH: 13
<212> TYPE: PRT
<213> ORGANISM: Artificial
<220> FEATURE:
<223> OTHER INFORMATION: synthetic peptide

<400> SEQUENCE: 26

Lys Lys Asp Ala Ser Ala Gln Gln Asp Ser Tyr Glu Phe
1               5                   10

<210> SEQ ID NO 27
<211> LENGTH: 12
<212> TYPE: PRT
<213> ORGANISM: Artificial
<220> FEATURE:
<223> OTHER INFORMATION: synthetic peptide

<400> SEQUENCE: 27

Asp Val Ser Glu Arg Ala Lys Lys Ala Ser Ala Arg
1               5                   10

<210> SEQ ID NO 28
<211> LENGTH: 11
<212> TYPE: PRT
<213> ORGANISM: Artificial
<220> FEATURE:
<223> OTHER INFORMATION: synthetic peptide

<400> SEQUENCE: 28

Lys Lys Lys Thr Leu Ala Glu Ile Asn Gln Lys
1               5                   10

<210> SEQ ID NO 29
<211> LENGTH: 12
<212> TYPE: PRT
<213> ORGANISM: Artificial
<220> FEATURE:
<223> OTHER INFORMATION: synthetic peptide

<400> SEQUENCE: 29

Trp Asn Leu Glu Ala Glu Lys Glu Asp Gly Glu Phe
1               5                   10

<210> SEQ ID NO 30
<211> LENGTH: 12
<212> TYPE: PRT
<213> ORGANISM: Artificial
<220> FEATURE:
<223> OTHER INFORMATION: synthetic peptide

<400> SEQUENCE: 30

Lys Glu Glu Ser Lys Gln Lys Leu Val Ser Phe Cys
1               5                   10

<210> SEQ ID NO 31
<211> LENGTH: 14
<212> TYPE: PRT
<213> ORGANISM: Artificial
<220> FEATURE:
<223> OTHER INFORMATION: synthetic peptide

<400> SEQUENCE: 31

Pro Ser Val Ile Ser Ser Pro Gln Ile Asn Gly Glu Ile Asp

```
<210> SEQ ID NO 32
<211> LENGTH: 11
<212> TYPE: PRT
<213> ORGANISM: Artificial
<220> FEATURE:
<223> OTHER INFORMATION: synthetic peptide

<400> SEQUENCE: 32

Thr Glu Ser Glu Cys Phe Gly Ser Leu Thr Glu
1               5                   10

<210> SEQ ID NO 33
<211> LENGTH: 12
<212> TYPE: PRT
<213> ORGANISM: Artificial
<220> FEATURE:
<223> OTHER INFORMATION: synthetic peptide

<400> SEQUENCE: 33

Pro Leu Ala Glu Gln Ile Glu Ser Pro Asp Thr Lys
1               5                   10

<210> SEQ ID NO 34
<211> LENGTH: 11
<212> TYPE: PRT
<213> ORGANISM: Artificial
<220> FEATURE:
<223> OTHER INFORMATION: synthetic peptide

<400> SEQUENCE: 34

Arg Asn Glu Val Val Thr Pro Glu Lys Val Cys
1               5                   10

<210> SEQ ID NO 35
<211> LENGTH: 15
<212> TYPE: PRT
<213> ORGANISM: Artificial
<220> FEATURE:
<223> OTHER INFORMATION: synthetic peptide

<400> SEQUENCE: 35

Lys Lys Ser Leu Pro Leu Glu Asn Asn Gly Lys Arg Gly His His
1               5                   10                  15

<210> SEQ ID NO 36
<211> LENGTH: 11
<212> TYPE: PRT
<213> ORGANISM: Artificial
<220> FEATURE:
<223> OTHER INFORMATION: synthetic peptide

<400> SEQUENCE: 36

Pro Ile Ser Lys Arg Cys Arg Thr Ser Ile Leu
1               5                   10

<210> SEQ ID NO 37
<211> LENGTH: 11
<212> TYPE: PRT
<213> ORGANISM: Artificial
<220> FEATURE:
<223> OTHER INFORMATION: synthetic peptide

<400> SEQUENCE: 37

Asp Phe Val Lys Gln Thr Val Pro Ser Glu Asn
1               5                   10
```

```
<210> SEQ ID NO 38
<211> LENGTH: 12
<212> TYPE: PRT
<213> ORGANISM: Artificial
<220> FEATURE:
<223> OTHER INFORMATION: synthetic peptide

<400> SEQUENCE: 38

Pro Glu Cys Ser Ser Pro Pro Ser Cys Lys Arg Lys
1               5                  10

<210> SEQ ID NO 39
<211> LENGTH: 11
<212> TYPE: PRT
<213> ORGANISM: Artificial
<220> FEATURE:
<223> OTHER INFORMATION: synthetic peptide

<400> SEQUENCE: 39

Met Ser Asp Glu Phe Ile Ser Leu Ser Pro Gly
1               5                  10

<210> SEQ ID NO 40
<211> LENGTH: 11
<212> TYPE: PRT
<213> ORGANISM: Artificial
<220> FEATURE:
<223> OTHER INFORMATION: synthetic peptide

<400> SEQUENCE: 40

Met Ser Ser Pro Ser Ala Met Lys Leu Leu Pro
1               5                  10

<210> SEQ ID NO 41
<211> LENGTH: 11
<212> TYPE: PRT
<213> ORGANISM: Artificial
<220> FEATURE:
<223> OTHER INFORMATION: synthetic peptide

<400> SEQUENCE: 41

Met Lys Leu Leu Pro Asn Met Ala Val Lys Arg
1               5                  10

<210> SEQ ID NO 42
<211> LENGTH: 14
<212> TYPE: PRT
<213> ORGANISM: Artificial
<220> FEATURE:
<223> OTHER INFORMATION: synthetic peptide

<400> SEQUENCE: 42

Met Ala Val Lys Arg Asn His Arg Gly Glu Thr Leu Leu His
1               5                  10

<210> SEQ ID NO 43
<211> LENGTH: 10
<212> TYPE: PRT
<213> ORGANISM: Artificial
<220> FEATURE:
<223> OTHER INFORMATION: synthetic peptide

<400> SEQUENCE: 43

His Ile Ala Ser Ile Lys Gly Asp Ile Pro
1               5                  10
```

```
<210> SEQ ID NO 44
<211> LENGTH: 12
<212> TYPE: PRT
<213> ORGANISM: Artificial
<220> FEATURE:
<223> OTHER INFORMATION: synthetic peptide

<400> SEQUENCE: 44

Lys Gly Asp Ile Pro Ser Val Glu Tyr Leu Leu Gln
1               5                   10

<210> SEQ ID NO 45
<211> LENGTH: 11
<212> TYPE: PRT
<213> ORGANISM: Artificial
<220> FEATURE:
<223> OTHER INFORMATION: synthetic peptide

<400> SEQUENCE: 45

His Ala Gly Trp Thr Pro Leu His Glu Ala Cys
1               5                   10

<210> SEQ ID NO 46
<211> LENGTH: 12
<212> TYPE: PRT
<213> ORGANISM: Artificial
<220> FEATURE:
<223> OTHER INFORMATION: synthetic peptide

<400> SEQUENCE: 46

His Leu Lys Val Val Glu Leu Leu Leu Gln His Lys
1               5                   10

<210> SEQ ID NO 47
<211> LENGTH: 13
<212> TYPE: PRT
<213> ORGANISM: Artificial
<220> FEATURE:
<223> OTHER INFORMATION: synthetic peptide

<400> SEQUENCE: 47

Gly Tyr Gln Asn Asp Ser Pro Leu His Asp Ala Ala Lys
1               5                   10

<210> SEQ ID NO 48
<211> LENGTH: 12
<212> TYPE: PRT
<213> ORGANISM: Artificial
<220> FEATURE:
<223> OTHER INFORMATION: synthetic peptide

<400> SEQUENCE: 48

Lys Leu Leu Leu Ser Tyr Gly Ala Ser Arg Asn Ala
1               5                   10

<210> SEQ ID NO 49
<211> LENGTH: 10
<212> TYPE: PRT
<213> ORGANISM: Artificial
<220> FEATURE:
<223> OTHER INFORMATION: synthetic peptide

<400> SEQUENCE: 49

Arg Asn Ala Val Asn Ile Phe Gly Leu Arg
1               5                   10
```

```
<210> SEQ ID NO 50
<211> LENGTH: 10
<212> TYPE: PRT
<213> ORGANISM: Artificial
<220> FEATURE:
<223> OTHER INFORMATION: synthetic peptide

<400> SEQUENCE: 50

Asn Ile Phe Gly Leu Arg Pro Val Asp Tyr
1               5                   10

<210> SEQ ID NO 51
<211> LENGTH: 12
<212> TYPE: PRT
<213> ORGANISM: Artificial
<220> FEATURE:
<223> OTHER INFORMATION: synthetic peptide

<400> SEQUENCE: 51

Met Lys Ser Leu Leu Leu Leu Pro Glu Lys Asn Glu
1               5                   10

<210> SEQ ID NO 52
<211> LENGTH: 12
<212> TYPE: PRT
<213> ORGANISM: Artificial
<220> FEATURE:
<223> OTHER INFORMATION: synthetic peptide

<400> SEQUENCE: 52

Lys Asn Glu Ser Ser Ser Ala Ser His Cys Ser Val
1               5                   10

<210> SEQ ID NO 53
<211> LENGTH: 11
<212> TYPE: PRT
<213> ORGANISM: Artificial
<220> FEATURE:
<223> OTHER INFORMATION: synthetic peptide

<400> SEQUENCE: 53

His Cys Ser Val Met Asn Thr Gly Gln Arg Arg
1               5                   10

<210> SEQ ID NO 54
<211> LENGTH: 11
<212> TYPE: PRT
<213> ORGANISM: Artificial
<220> FEATURE:
<223> OTHER INFORMATION: synthetic peptide

<400> SEQUENCE: 54

Met Asn Thr Gly Gln Arg Arg Asp Gly Pro Leu
1               5                   10

<210> SEQ ID NO 55
<211> LENGTH: 14
<212> TYPE: PRT
<213> ORGANISM: Artificial
<220> FEATURE:
<223> OTHER INFORMATION: synthetic peptide

<400> SEQUENCE: 55

Met Leu Ser Glu Leu Ala Val Ile Leu Lys Ala Lys Lys Tyr
1               5                   10

<210> SEQ ID NO 56
```

```
<211> LENGTH: 14
<212> TYPE: PRT
<213> ORGANISM: Artificial
<220> FEATURE:
<223> OTHER INFORMATION: synthetic peptide

<400> SEQUENCE: 56

Glu Phe Asp Ser Thr Val Thr His Val Val Pro Gly Asp
1               5                   10

<210> SEQ ID NO 57
<211> LENGTH: 12
<212> TYPE: PRT
<213> ORGANISM: Artificial
<220> FEATURE:
<223> OTHER INFORMATION: synthetic peptide

<400> SEQUENCE: 57

Met Leu Gly Ile Leu Asn Gly Cys Trp Ile Leu Lys
1               5                   10

<210> SEQ ID NO 58
<211> LENGTH: 14
<212> TYPE: PRT
<213> ORGANISM: Artificial
<220> FEATURE:
<223> OTHER INFORMATION: synthetic peptide

<400> SEQUENCE: 58

Lys Phe Glu Trp Val Lys Ala Cys Leu Arg Arg Lys Val Cys
1               5                   10

<210> SEQ ID NO 59
<211> LENGTH: 13
<212> TYPE: PRT
<213> ORGANISM: Artificial
<220> FEATURE:
<223> OTHER INFORMATION: synthetic peptide

<400> SEQUENCE: 59

Lys Val Cys Glu Gln Glu Glu Lys Tyr Glu Ile Pro Glu
1               5                   10

<210> SEQ ID NO 60
<211> LENGTH: 12
<212> TYPE: PRT
<213> ORGANISM: Artificial
<220> FEATURE:
<223> OTHER INFORMATION: synthetic peptide

<400> SEQUENCE: 60

Arg Glu Gln Leu Leu Pro Lys Leu Phe Asp Gly Cys
1               5                   10

<210> SEQ ID NO 61
<211> LENGTH: 12
<212> TYPE: PRT
<213> ORGANISM: Artificial
<220> FEATURE:
<223> OTHER INFORMATION: synthetic peptide

<400> SEQUENCE: 61

Phe Tyr Leu Trp Gly Thr Phe Lys His His Pro Lys
1               5                   10

<210> SEQ ID NO 62
<211> LENGTH: 14
```

<212> TYPE: PRT
<213> ORGANISM: Artificial
<220> FEATURE:
<223> OTHER INFORMATION: synthetic peptide

<400> SEQUENCE: 62

Lys Leu Val Thr Ala Gly Gly Gly Gln Ile Leu Ser Arg Lys
1               5                   10

<210> SEQ ID NO 63
<211> LENGTH: 16
<212> TYPE: PRT
<213> ORGANISM: Artificial
<220> FEATURE:
<223> OTHER INFORMATION: synthetic peptide

<400> SEQUENCE: 63

Asp Ser Asp Val Thr Gln Thr Ile Asn Thr Val Ala Tyr His Ala Arg
1               5                   10                  15

<210> SEQ ID NO 64
<211> LENGTH: 13
<212> TYPE: PRT
<213> ORGANISM: Artificial
<220> FEATURE:
<223> OTHER INFORMATION: synthetic peptide

<400> SEQUENCE: 64

Arg Cys Phe Thr Gln Tyr Ile Ile Tyr Glu Asp Leu Cys
1               5                   10

<210> SEQ ID NO 65
<211> LENGTH: 11
<212> TYPE: PRT
<213> ORGANISM: Artificial
<220> FEATURE:
<223> OTHER INFORMATION: synthetic peptide

<400> SEQUENCE: 65

Asn Tyr His Pro Glu Arg Val Arg Gln Gly Lys
1               5                   10

<210> SEQ ID NO 66
<211> LENGTH: 13
<212> TYPE: PRT
<213> ORGANISM: Artificial
<220> FEATURE:
<223> OTHER INFORMATION: synthetic peptide

<400> SEQUENCE: 66

Lys Val Trp Lys Ala Pro Ser Ser Trp Phe Ile Asp Cys
1               5                   10

<210> SEQ ID NO 67
<211> LENGTH: 10
<212> TYPE: PRT
<213> ORGANISM: Artificial
<220> FEATURE:
<223> OTHER INFORMATION: synthetic peptide

<400> SEQUENCE: 67

Met Ser Phe Glu Leu Leu Pro Leu Asp Ser
1               5                   10

<210> SEQ ID NO 68
<211> LENGTH: 14
<212> TYPE: PRT

<213> ORGANISM: Artificial
<220> FEATURE:
<223> OTHER INFORMATION: synthetic peptide

<400> SEQUENCE: 68

Lys Leu Leu Arg Cys Ser Arg Cys Asn Cys Val Ser Asp Cys
1               5                   10

<210> SEQ ID NO 69
<211> LENGTH: 11
<212> TYPE: PRT
<213> ORGANISM: Artificial
<220> FEATURE:
<223> OTHER INFORMATION: synthetic peptide

<400> SEQUENCE: 69

Cys Ala Ala Arg Val Asp Leu Lys Glu Asp Lys
1               5                   10

<210> SEQ ID NO 70
<211> LENGTH: 10
<212> TYPE: PRT
<213> ORGANISM: Artificial
<220> FEATURE:
<223> OTHER INFORMATION: synthetic peptide

<400> SEQUENCE: 70

His Ile Ala Ser Ile Lys His Glu Ala Cys
1               5                   10

<210> SEQ ID NO 71
<211> LENGTH: 10
<212> TYPE: PRT
<213> ORGANISM: Artificial
<220> FEATURE:
<223> OTHER INFORMATION: synthetic peptide

<400> SEQUENCE: 71

Glu Phe Asp Ser Thr Gly Val Lys Ala Cys
1               5                   10

<210> SEQ ID NO 72
<211> LENGTH: 12
<212> TYPE: PRT
<213> ORGANISM: Artificial
<220> FEATURE:
<223> OTHER INFORMATION: synthetic peptide

<400> SEQUENCE: 72

His Asp Asn Glu Leu Ser Gly Arg His Thr Phe Cys
1               5                   10

<210> SEQ ID NO 73
<211> LENGTH: 14
<212> TYPE: PRT
<213> ORGANISM: Artificial
<220> FEATURE:
<223> OTHER INFORMATION: synthetic peptide

<400> SEQUENCE: 73

Met Thr Met Ser Cys Gln Gly Asp Ile Pro Ser Val Glu Tyr
1               5                   10

<210> SEQ ID NO 74
<211> LENGTH: 12
<212> TYPE: PRT
<213> ORGANISM: Artificial

```
<220> FEATURE:
<223> OTHER INFORMATION: synthetic peptide

<400> SEQUENCE: 74

Thr Pro Glu Lys Gly Asp Ile Pro Ser Val Glu Tyr
1               5                   10

<210> SEQ ID NO 75
<211> LENGTH: 14
<212> TYPE: PRT
<213> ORGANISM: Artificial
<220> FEATURE:
<223> OTHER INFORMATION: synthetic peptide

<400> SEQUENCE: 75

Lys Leu Leu Arg Cys Ser Arg Cys Asn Ile Phe Gly Leu Arg
1               5                   10

<210> SEQ ID NO 76
<211> LENGTH: 13
<212> TYPE: PRT
<213> ORGANISM: Artificial
<220> FEATURE:
<223> OTHER INFORMATION: synthetic peptide

<400> SEQUENCE: 76

Cys Glu His Ile Phe Cys Ser Asn Ile Phe Gly Leu Arg
1               5                   10

<210> SEQ ID NO 77
<211> LENGTH: 11
<212> TYPE: PRT
<213> ORGANISM: Artificial
<220> FEATURE:
<223> OTHER INFORMATION: synthetic peptide

<400> SEQUENCE: 77

His Asp Asn Glu Leu Ser Gly Val Lys Ala Cys
1               5                   10

<210> SEQ ID NO 78
<211> LENGTH: 15
<212> TYPE: PRT
<213> ORGANISM: Artificial
<220> FEATURE:
<223> OTHER INFORMATION: synthetic peptide

<400> SEQUENCE: 78

His Asp Asn Glu Leu Ser Val Thr His Val Val Val Pro Gly Asp
1               5                   10                  15

<210> SEQ ID NO 79
<211> LENGTH: 10
<212> TYPE: PRT
<213> ORGANISM: Artificial
<220> FEATURE:
<223> OTHER INFORMATION: synthetic peptide

<400> SEQUENCE: 79

Cys Ala Ala Arg Val Gly Val Lys Ala Cys
1               5                   10

<210> SEQ ID NO 80
<211> LENGTH: 14
<212> TYPE: PRT
<213> ORGANISM: Artificial
<220> FEATURE:
```

<223> OTHER INFORMATION: synthetic peptide

<400> SEQUENCE: 80

Cys Ala Ala Arg Val Val Thr His Val Val Val Pro Gly Asp
1               5                   10

<210> SEQ ID NO 81
<211> LENGTH: 20
<212> TYPE: DNA
<213> ORGANISM: Artificial
<220> FEATURE:
<223> OTHER INFORMATION: synthetic nucleotide

<400> SEQUENCE: 81
acaagcgcca gagagatgat                                                   20

<210> SEQ ID NO 82
<211> LENGTH: 20
<212> TYPE: DNA
<213> ORGANISM: Artificial
<220> FEATURE:
<223> OTHER INFORMATION: synthetic nucleotide

<400> SEQUENCE: 82
gatgtgggag aggatgagga                                                   20

<210> SEQ ID NO 83
<211> LENGTH: 20
<212> TYPE: DNA
<213> ORGANISM: Artificial
<220> FEATURE:
<223> OTHER INFORMATION: synthetic nucleotide

<400> SEQUENCE: 83
agccacatcg ctcagacacc                                                   20

<210> SEQ ID NO 84
<211> LENGTH: 19
<212> TYPE: DNA
<213> ORGANISM: Artificial
<220> FEATURE:
<223> OTHER INFORMATION: synthetic nucleotide

<400> SEQUENCE: 84
gtatctagcg ccagcatcg                                                    19

<210> SEQ ID NO 85
<211> LENGTH: 20
<212> TYPE: DNA
<213> ORGANISM: Artificial
<220> FEATURE:
<223> OTHER INFORMATION: synthetic nucleotide

<400> SEQUENCE: 85
gaggagcctt tcatccgaag                                                   20

<210> SEQ ID NO 86
<211> LENGTH: 20
<212> TYPE: DNA
<213> ORGANISM: Artificial
<220> FEATURE:
<223> OTHER INFORMATION: synthetic nucleotide

<400> SEQUENCE: 86
gaggagcctt tcatccgaag                                                   20

```
<210> SEQ ID NO 87
<211> LENGTH: 20
<212> TYPE: DNA
<213> ORGANISM: Artificial
<220> FEATURE:
<223> OTHER INFORMATION: synthetic nucleotide

<400> SEQUENCE: 87
gaggagcctt tcatccgaag                                                  20

<210> SEQ ID NO 88
<211> LENGTH: 23
<212> TYPE: DNA
<213> ORGANISM: Artificial
<220> FEATURE:
<223> OTHER INFORMATION: synthetic nucleotide

<400> SEQUENCE: 88
gtttagccct cgaagtaaga aag                                              23

<210> SEQ ID NO 89
<211> LENGTH: 26
<212> TYPE: DNA
<213> ORGANISM: Artificial
<220> FEATURE:
<223> OTHER INFORMATION: synthetic nucleotide

<400> SEQUENCE: 89
gtcagatatg ttgtgagtaa agcttc                                           26

<210> SEQ ID NO 90
<211> LENGTH: 20
<212> TYPE: DNA
<213> ORGANISM: Artificial
<220> FEATURE:
<223> OTHER INFORMATION: synthetic nucleotide

<400> SEQUENCE: 90
agcaagtggc tccttgacag                                                  20

<210> SEQ ID NO 91
<211> LENGTH: 25
<212> TYPE: DNA
<213> ORGANISM: Artificial
<220> FEATURE:
<223> OTHER INFORMATION: synthetic nucleotide

<400> SEQUENCE: 91
ccagtcccat ttctaagaga tgtag                                            25

<210> SEQ ID NO 92
<211> LENGTH: 18
<212> TYPE: DNA
<213> ORGANISM: Artificial
<220> FEATURE:
<223> OTHER INFORMATION: synthetic nucleotide

<400> SEQUENCE: 92
gaggagagac tttgctcc                                                    18

<210> SEQ ID NO 93
<211> LENGTH: 18
<212> TYPE: DNA
<213> ORGANISM: Artificial
<220> FEATURE:
<223> OTHER INFORMATION: synthetic nucleotide
```

<400> SEQUENCE: 93
gctggatgga caccattg                                                    18

<210> SEQ ID NO 94
<211> LENGTH: 20
<212> TYPE: DNA
<213> ORGANISM: Artificial
<220> FEATURE:
<223> OTHER INFORMATION: synthetic nucleotide

<400> SEQUENCE: 94
ctccagcata aggcattggt                                                  20

<210> SEQ ID NO 95
<211> LENGTH: 25
<212> TYPE: DNA
<213> ORGANISM: Artificial
<220> FEATURE:
<223> OTHER INFORMATION: synthetic nucleotide

<400> SEQUENCE: 95
attgcaggct gggtttgcac tgaag                                            25

<210> SEQ ID NO 96
<211> LENGTH: 20
<212> TYPE: DNA
<213> ORGANISM: Artificial
<220> FEATURE:
<223> OTHER INFORMATION: synthetic nucleotide

<400> SEQUENCE: 96
ttttgatacc cggtggtgtt                                                  20

<210> SEQ ID NO 97
<211> LENGTH: 20
<212> TYPE: DNA
<213> ORGANISM: Artificial
<220> FEATURE:
<223> OTHER INFORMATION: synthetic nucleotide

<400> SEQUENCE: 97
cgaaccctct ctgggtgata                                                  20

<210> SEQ ID NO 98
<211> LENGTH: 20
<212> TYPE: DNA
<213> ORGANISM: Artificial
<220> FEATURE:
<223> OTHER INFORMATION: synthetic nucleotide

<400> SEQUENCE: 98
cgaaccctct ctgggtgata                                                  20

<210> SEQ ID NO 99
<211> LENGTH: 20
<212> TYPE: DNA
<213> ORGANISM: Artificial
<220> FEATURE:
<223> OTHER INFORMATION: synthetic nucleotide

<400> SEQUENCE: 99
cgaaccctct ctgggtgata                                                  20

<210> SEQ ID NO 100

<211> LENGTH: 20
<212> TYPE: DNA
<213> ORGANISM: Artificial
<220> FEATURE:
<223> OTHER INFORMATION: synthetic nucleotide

<400> SEQUENCE: 100
cgaaccctct ctgggtgata                                         20

<210> SEQ ID NO 101
<211> LENGTH: 20
<212> TYPE: DNA
<213> ORGANISM: Artificial
<220> FEATURE:
<223> OTHER INFORMATION: synthetic nucleotide

<400> SEQUENCE: 101
cgaaccctct ctgggtgata                                         20

<210> SEQ ID NO 102
<211> LENGTH: 20
<212> TYPE: DNA
<213> ORGANISM: Artificial
<220> FEATURE:
<223> OTHER INFORMATION: synthetic peptide

<400> SEQUENCE: 102
cgaaccctct ctgggtgata                                         20

<210> SEQ ID NO 103
<211> LENGTH: 20
<212> TYPE: DNA
<213> ORGANISM: Artificial
<220> FEATURE:
<223> OTHER INFORMATION: synthetic nucleotide

<400> SEQUENCE: 103
cgaaccctct ctgggtgata                                         20

<210> SEQ ID NO 104
<211> LENGTH: 20
<212> TYPE: DNA
<213> ORGANISM: Artificial
<220> FEATURE:
<223> OTHER INFORMATION: synthetic nucleotide

<400> SEQUENCE: 104
cgaaccctct ctgggtgata                                         20

<210> SEQ ID NO 105
<211> LENGTH: 622
<212> TYPE: PRT
<213> ORGANISM: Homo sapiens

<400> SEQUENCE: 105

Met Pro Asp Asn Arg Gln Pro Arg Asn Arg Gln Pro Arg Ile Arg Ser
 1               5                  10                  15

Gly Asn Glu Pro Arg Ser Ala Pro Ala Met Glu Pro Asp Gly Arg Gly
            20                  25                  30

Ala Trp Ala His Ser Arg Ala Ala Leu Asp Arg Leu Glu Lys Leu Leu
        35                  40                  45

Arg Cys Ser Arg Cys Asn Cys Val Ser Asp Cys Ile Gly Thr Gly Cys
    50                  55                  60

Pro Val Cys Tyr Thr Pro Ala Trp Ile Gln Asp Leu Lys Ile Asn Arg

```
            65                  70                  75                  80
        Gln Leu Asp Ser Met Ile Gln Leu Cys Ser Lys Leu Arg Asn Leu Leu
                         85                  90                  95

His Asp Asn Glu Leu Ser Asp Leu Lys Glu Asp Lys Pro Arg Lys Ser
                        100                 105                 110

Leu Phe Asn Asp Ala Gly Asn Lys Asn Ser Ile Lys Met Trp Phe
                        115                 120                 125

Ser Pro Arg Ser Lys Lys Val Arg Tyr Val Ser Lys Ala Ser Val
                        130                 135                 140

Gln Thr Gln Pro Ala Ile Lys Lys Asp Ala Ser Ala Gln Gln Asp Ser
        145                 150                 155                 160

Tyr Glu Phe Val Ser Pro Ser Pro Ala Asp Val Ser Glu Arg Ala
                        165                 170                 175

Lys Lys Ala Ser Ala Arg Ser Gly Lys Lys Gln Lys Lys Lys Thr Leu
                        180                 185                 190

Ala Glu Ile Asn Gln Lys Trp Asn Leu Glu Ala Glu Lys Glu Asp Gly
                        195                 200                 205

Glu Phe Asp Ser Lys Glu Glu Ser Lys Gln Lys Leu Val Ser Phe Cys
                        210                 215                 220

Ser Gln Pro Ser Val Ile Ser Ser Pro Gln Ile Asn Gly Glu Ile Asp
        225                 230                 235                 240

Leu Leu Ala Ser Gly Ser Leu Thr Glu Ser Glu Cys Phe Gly Ser Leu
                        245                 250                 255

Thr Glu Val Ser Leu Pro Leu Ala Glu Gln Ile Glu Ser Pro Asp Thr
                        260                 265                 270

Lys Ser Arg Asn Glu Val Val Thr Pro Ile Lys Gly Asp Ile Pro Ser
                        275                 280                 285

Val Glu Tyr Leu Leu Gln Asn Gly Ser Asp Pro Asn Val Lys Asp His
                        290                 295                 300

Ala Gly Trp Thr Pro Leu His Glu Ala Cys Asn His Gly His Leu Lys
        305                 310                 315                 320

Val Val Glu Leu Leu Leu Gln His Lys Ala Leu Val Asn Thr Thr Gly
                        325                 330                 335

Tyr Gln Asn Asp Ser Pro Leu His Asp Ala Ala Lys Asn Gly His Val
                        340                 345                 350

Asp Ile Val Lys Leu Leu Leu Ser Tyr Gly Ala Ser Arg Asn Ala Val
                        355                 360                 365

Asn Ile Phe Gly Leu Arg Pro Val Asp Tyr Thr Asp Asp Glu Ser Met
                        370                 375                 380

Lys Ser Leu Leu Leu Leu Pro Glu Lys Asn Glu Ser Ser Ser Ala Ser
        385                 390                 395                 400

His Cys Ser Val Met Asn Thr Gly Gln Arg Arg Asp Gly Pro Leu Val
                        405                 410                 415

Leu Ile Gly Ser Gly Leu Ser Ser Glu Gln Gln Lys Met Leu Ser Glu
                        420                 425                 430

Leu Ala Val Ile Leu Lys Ala Lys Lys Tyr Thr Glu Phe Asp Ser Thr
                        435                 440                 445

Val Thr His Val Val Pro Gly Asp Ala Val Gln Ser Thr Leu Lys
                        450                 455                 460

Cys Met Leu Gly Ile Leu Asn Gly Cys Trp Ile Leu Lys Phe Glu Trp
        465                 470                 475                 480

Val Lys Ala Cys Leu Arg Arg Lys Val Cys Glu Gln Glu Glu Lys Tyr
                        485                 490                 495
```

```
Glu Ile Pro Glu Gly Pro Arg Ser Arg Leu Asn Arg Glu Gln Leu
            500                 505                 510

Leu Pro Lys Leu Phe Asp Gly Cys Tyr Phe Tyr Leu Trp Gly Thr Phe
        515                 520                 525

Lys His His Pro Lys Asp Asn Leu Ile Lys Leu Val Thr Ala Gly Gly
        530                 535                 540

Gly Gln Ile Leu Ser Arg Lys Pro Lys Pro Asp Ser Asp Val Thr Gln
545                 550                 555                 560

Thr Ile Asn Thr Val Ala Tyr His Ala Arg Pro Asp Ser Asp Gln Arg
                565                 570                 575

Phe Cys Thr Gln Tyr Ile Ile Tyr Glu Asp Leu Cys Asn Tyr His Pro
            580                 585                 590

Glu Arg Val Arg Gln Gly Lys Val Trp Lys Ala Pro Ser Ser Trp Phe
            595                 600                 605

Ile Asp Cys Val Met Ser Phe Glu Leu Leu Pro Leu Asp Ser
        610                 615                 620

<210> SEQ ID NO 106
<211> LENGTH: 705
<212> TYPE: PRT
<213> ORGANISM: Homo sapiens

<400> SEQUENCE: 106

Ala Ser Leu Trp Phe Pro Glu Ala Ser Leu Leu Pro Ala Leu Arg Gly
1               5                   10                  15

Ala Phe His Pro Lys Ala Gly Arg Cys Arg Ile Ile Gly Ser Arg Gly
            20                  25                  30

Thr Gly Ser Arg Gly Ser Ala Pro Gly Thr Ser Leu Val Pro Arg Pro
        35                  40                  45

Pro Trp Asn Arg Met Val Ala Val Pro Gly Pro Thr Val Ala Pro Arg
    50                  55                  60

Ser Thr Ala Trp Arg Ser Cys Cys Ala Ala Arg Val Asp Leu Lys Glu
65                  70                  75                  80

Asp Lys Pro Arg Lys Ser Leu Phe Asn Asp Ala Gly Asn Lys Lys Asn
                85                  90                  95

Ser Ile Lys Met Trp Phe Ser Pro Arg Ser Lys Lys Val Arg Tyr Val
            100                 105                 110

Val Ser Lys Ala Ser Val Gln Thr Gln Pro Ala Ile Lys Lys Asp Ala
        115                 120                 125

Ser Ala Gln Gln Asp Ser Tyr Glu Phe Val Ser Pro Ser Pro Ala
    130                 135                 140

Asp Val Ser Glu Arg Ala Lys Lys Ala Ser Ala Arg Ser Gly Lys Lys
145                 150                 155                 160

Gln Lys Lys Lys Thr Leu Ala Glu Ile Asn Gln Lys Trp Asn Leu Glu
                165                 170                 175

Ala Glu Lys Glu Asp Gly Glu Phe Asp Ser Lys Glu Ser Lys Gln
            180                 185                 190

Lys Leu Val Ser Phe Cys Ser Gln Pro Ser Val Ile Ser Ser Pro Gln
        195                 200                 205

Ile Asn Gly Glu Ile Asp Leu Leu Ala Ser Gly Ser Leu Thr Glu Ser
    210                 215                 220

Glu Cys Phe Gly Ser Leu Thr Glu Val Ser Leu Pro Leu Ala Glu Gln
225                 230                 235                 240

Ile Glu Ser Pro Asp Thr Lys Ser Arg Asn Glu Val Val Thr Pro Glu
```

-continued

```
                245                 250                 255
Lys Val Cys Lys Asn Tyr Leu Thr Ser Lys Lys Ser Leu Pro Leu Glu
            260                 265                 270

Asn Asn Gly Lys Arg Gly His His Asn Arg Leu Ser Ser Pro Ile Ser
            275                 280                 285

Lys Arg Cys Arg Thr Ser Ile Leu Ser Thr Ser Gly Asp Phe Val Lys
        290                 295                 300

Gln Thr Val Pro Ser Glu Asn Ile Pro Leu Pro Glu Cys Ser Ser Pro
305                 310                 315                 320

Pro Ser Cys Lys Arg Lys Val Gly Gly Thr Ser Gly Arg Lys Asn Ser
            325                 330                 335

Asn Met Ser Asp Glu Phe Ile Ser Leu Ser Pro Gly Thr Pro Pro Ser
            340                 345                 350

Thr Leu Ser Ser Ser Ser Tyr Arg Gln Val Met Ser Ser Pro Ser Ala
            355                 360                 365

Met Lys Leu Leu Pro Asn Met Ala Val Lys Arg Asn His Arg Gly Glu
        370                 375                 380

Thr Leu Leu His Ile Ala Ser Ile Lys His Glu Ala Cys Asn His Gly
385                 390                 395                 400

His Leu Lys Val Val Glu Leu Leu Leu Gln His Lys Ala Leu Val Asn
            405                 410                 415

Thr Thr Gly Tyr Gln Asn Asp Ser Pro Leu His Asp Ala Ala Lys Asn
            420                 425                 430

Gly His Val Asp Ile Val Lys Leu Leu Leu Ser Tyr Gly Ala Ser Arg
        435                 440                 445

Asn Ala Val Asn Ile Phe Gly Leu Arg Pro Val Asp Tyr Thr Asp Asp
450                 455                 460

Glu Ser Met Lys Ser Leu Leu Leu Pro Glu Lys Asn Glu Ser Ser
465                 470                 475                 480

Ser Ala Ser His Cys Ser Val Met Asn Thr Gly Gln Arg Arg Asp Gly
            485                 490                 495

Pro Leu Val Leu Ile Gly Ser Gly Leu Ser Ser Glu Gln Gln Lys Met
            500                 505                 510

Leu Ser Glu Leu Ala Val Ile Leu Lys Ala Lys Lys Tyr Thr Glu Phe
        515                 520                 525

Asp Ser Thr Val Thr His Val Val Pro Gly Asp Ala Val Gln Ser
            530                 535                 540

Thr Leu Lys Cys Met Leu Gly Ile Leu Asn Gly Cys Trp Ile Leu Lys
545                 550                 555                 560

Phe Glu Trp Val Lys Ala Cys Leu Arg Arg Lys Val Cys Glu Gln Glu
            565                 570                 575

Glu Lys Tyr Glu Ile Pro Glu Gly Pro Arg Arg Ser Arg Leu Asn Arg
        580                 585                 590

Glu Gln Leu Leu Pro Lys Leu Phe Asp Gly Cys Tyr Phe Tyr Leu Trp
            595                 600                 605

Gly Thr Phe Lys His His Pro Lys Asp Asn Leu Ile Lys Leu Val Thr
        610                 615                 620

Ala Gly Gly Gly Gln Ile Leu Ser Arg Lys Pro Lys Pro Asp Ser Asp
625                 630                 635                 640

Val Thr Gln Thr Ile Asn Thr Val Ala Tyr His Ala Arg Pro Asp Ser
            645                 650                 655

Asp Gln Arg Phe Cys Thr Gln Tyr Ile Ile Tyr Glu Asp Leu Cys Asn
            660                 665                 670
```

```
Tyr His Pro Glu Arg Val Arg Gln Gly Lys Val Trp Lys Ala Pro Ser
        675                 680                 685

Ser Trp Phe Ile Asp Cys Val Met Ser Phe Glu Leu Leu Pro Leu Asp
    690                 695                 700

Ser
705

<210> SEQ ID NO 107
<211> LENGTH: 19
<212> TYPE: DNA
<213> ORGANISM: Artificial
<220> FEATURE:
<223> OTHER INFORMATION: synthetic nucleotide

<400> SEQUENCE: 107
cattctgaga gagcctgtg                                                   19

<210> SEQ ID NO 108
<211> LENGTH: 19
<212> TYPE: DNA
<213> ORGANISM: Artificial
<220> FEATURE:
<223> OTHER INFORMATION: synthetic nucleotide

<400> SEQUENCE: 108
gtgctcagca agactcata                                                   19

<210> SEQ ID NO 109
<211> LENGTH: 21
<212> TYPE: DNA
<213> ORGANISM: Artificial
<220> FEATURE:
<223> OTHER INFORMATION: synthetic nucleotide

<400> SEQUENCE: 109
aagtctcttt accattggct g                                                21

<210> SEQ ID NO 110
<211> LENGTH: 21
<212> TYPE: DNA
<213> ORGANISM: Artificial
<220> FEATURE:
<223> OTHER INFORMATION: synthetic nucleotide

<400> SEQUENCE: 110
aagtgtatgc ttgggattct c                                                21

<210> SEQ ID NO 111
<211> LENGTH: 110
<212> TYPE: RNA
<213> ORGANISM: Artificial
<220> FEATURE:
<223> OTHER INFORMATION: synthetic nucleotide

<400> SEQUENCE: 111
gaucugucug ucuucuguau auacccugua gauccgaauu uguguaagga auuuuguggu       60
cacaaauucg uaucuagggg aauauguagu ugacauaaac acuccgcucu                110

<210> SEQ ID NO 112
<211> LENGTH: 110
<212> TYPE: RNA
<213> ORGANISM: Artificial
<220> FEATURE:
<223> OTHER INFORMATION: synthetic nucleotide
```

<400> SEQUENCE: 112
ccagagguug uaacguuguc uauauauacc cuguagaacc gaauuugugu gguauccgua    60
uagucacaga uucgauucua ggggaauaua uggucgaugc aaaaacuuca              110

<210> SEQ ID NO 113
<211> LENGTH: 89
<212> TYPE: RNA
<213> ORGANISM: Artificial
<220> FEATURE:
<223> OTHER INFORMATION: synthetic nucleotide

<400> SEQUENCE: 113
ugcugcuggc cagagcucuu uucacauugu gcuacugucu gcaccuguca cuagcagugc    60
aauguuaaaa gggcauuggc cguguagug                                     89

<210> SEQ ID NO 114
<211> LENGTH: 82
<212> TYPE: RNA
<213> ORGANISM: Artificial
<220> FEATURE:
<223> OTHER INFORMATION: synthetic nucleotide

<400> SEQUENCE: 114
ggccugcccg acacucuuuc ccuguugcac uacuauaggc cgcugggaag cagugcaaug    60
augaaagggc aucggucagg uc                                            82

<210> SEQ ID NO 115
<211> LENGTH: 73
<212> TYPE: RNA
<213> ORGANISM: Artificial
<220> FEATURE:
<223> OTHER INFORMATION: synthetic nucleotide

<400> SEQUENCE: 115 caggugugu gacugguuga ccagaggggc augcacugug uucacccugu gggccaccua     60
gucaccaacc cuc                                                      73

<210> SEQ ID NO 116
<211> LENGTH: 86
<212> TYPE: RNA
<213> ORGANISM: Artificial
<220> FEATURE:
<223> OTHER INFORMATION: synthetic nucleotide

<400> SEQUENCE: 116
uggggcccug gcugggauau caucauauac uguaaguuug cgaugagaca cuacaguaua    60
gaugauguac uagaccgggc acccccc                                       86

<210> SEQ ID NO 117
<211> LENGTH: 68
<212> TYPE: RNA
<213> ORGANISM: Artificial
<220> FEATURE:
<223> OTHER INFORMATION: synthetic nucleotide

<400> SEQUENCE: 117
gaggcaaagu ucugagacac uccgacucug aguaugauag aagucagugc acuacagaac    60
uuugucuc                                                            68

<210> SEQ ID NO 118

```
<211> LENGTH: 99
<212> TYPE: RNA
<213> ORGANISM: Artificial
<220> FEATURE:
<223> OTHER INFORMATION: synthetic nucleotide

<400> SEQUENCE: 118
caagcacgau uagcauuuga ggugaaguuc uguuauacac ucaggcugug gcucucugaa    60
agucagugca ucacagaacu uugucucgaa agcuuucua                          99

<210> SEQ ID NO 119
<211> LENGTH: 87
<212> TYPE: RNA
<213> ORGANISM: Artificial
<220> FEATURE:
<223> OTHER INFORMATION: synthetic nucleotide

<400> SEQUENCE: 119 ugucccccc ggcccagguu cugugauaca cuccgacucg ggcucuggag cagucagugc    60
augacagaac uugggcccgg aaggacc                                       87

<210> SEQ ID NO 120
<211> LENGTH: 110
<212> TYPE: RNA
<213> ORGANISM: Artificial
<220> FEATURE:
<223> OTHER INFORMATION: synthetic nucleotide

<400> SEQUENCE: 120
agaagggcua ucaggccagc cuucagagga cuccaaggaa cauucaacgc ugucggugag   60
uuugggauuu gaaaaaacca cugaccguug acuguaccuu ggggucuua              110

<210> SEQ ID NO 121
<211> LENGTH: 110
<212> TYPE: RNA
<213> ORGANISM: Artificial
<220> FEATURE:
<223> OTHER INFORMATION: synthetic nucleotide

<400> SEQUENCE: 121
ugaguuuuga gguugcuuca gugaacauuc aacgcugucg gugaguuugg aauuaaaauc   60
aaaaccaucg accguugauu guacccuaug gcuaaccauc aucuacucca             110

<210> SEQ ID NO 122
<211> LENGTH: 110
<212> TYPE: RNA
<213> ORGANISM: Artificial
<220> FEATURE:
<223> OTHER INFORMATION: synthetic nucleotide

<400> SEQUENCE: 122
ccugugcaga gauuauuuuu uaaaagguca caaucaacau ucauugcugu cgguggguug   60
aacugugugg acaagcucac ugaacaauga augcaacugu ggccccgcuu             110

<210> SEQ ID NO 123
<211> LENGTH: 89
<212> TYPE: RNA
<213> ORGANISM: Artificial
<220> FEATURE:
<223> OTHER INFORMATION: synthetic nucleotide

<400> SEQUENCE: 123
cugauggcug cacucaacau ucauugcugu cgguggguuu gagucugaau caacucacug   60
```
aucaaugaau gcaaacugcg gaccaaaca						89

<210> SEQ ID NO 124
<211> LENGTH: 82
<212> TYPE: RNA
<213> ORGANISM: Artificial
<220> FEATURE:
<223> OTHER INFORMATION: synthetic nucleotide

<400> SEQUENCE: 124
gcaguccucu guuaguuuug cauaguugca cuacaagaag aauguaguug ugcaaaucua		60 ugcaaaacug augguggccu gc						82

<210> SEQ ID NO 125
<211> LENGTH: 87
<212> TYPE: RNA
<213> ORGANISM: Artificial
<220> FEATURE:
<223> OTHER INFORMATION: synthetic nucleotide

<400> SEQUENCE: 125
cacuguucua ugguuaguuu ugcagguuug cauccagcug ugugauauuc ugcugugcaa		60 auccaugcaa aacugacugu gguagug						87

<210> SEQ ID NO 126
<211> LENGTH: 96
<212> TYPE: RNA
<213> ORGANISM: Artificial
<220> FEATURE:
<223> OTHER INFORMATION: synthetic nucleotide

<400> SEQUENCE: 126
acauugcuac uuacaauuag uuuugcaggu uugcauuuca gcguauauau guauaugugg		60 cugugcaaau ccaugcaaaa cugauuguga uaaugu						96

<210> SEQ ID NO 127
<211> LENGTH: 110
<212> TYPE: RNA
<213> ORGANISM: Artificial
<220> FEATURE:
<223> OTHER INFORMATION: synthetic nucleotide

<400> SEQUENCE: 127 guguuggga cucgcgcgcu ggguccagug guucuuaaca guucaacagu ucguagcgc		60 aaugugaaa uguuuaggac cacuagaccc ggcgggcgcg gcgacagcga				110

<210> SEQ ID NO 128
<211> LENGTH: 86
<212> TYPE: RNA
<213> ORGANISM: Artificial
<220> FEATURE:
<223> OTHER INFORMATION: synthetic nucleotide

<400> SEQUENCE: 128
acugcuaacg aaugcucuga cuuuauugca cuacuguacu uuacagcuag cagugcaaua		60 guauugucaa agcaucugaa agcagg						86

<210> SEQ ID NO 129
<211> LENGTH: 78
<212> TYPE: RNA
<213> ORGANISM: Artificial
<220> FEATURE:

<223> OTHER INFORMATION: synthetic nucleotide

<400> SEQUENCE: 129
gccgcaggug cucugacgag guugcacuac ugugcucuga gaagcagugc aaugauauug    60
ucaaagcauc ugggacca    78

<210> SEQ ID NO 130
<211> LENGTH: 85
<212> TYPE: RNA
<213> ORGANISM: Artificial
<220> FEATURE:
<223> OTHER INFORMATION: synthetic nucleotide

<400> SEQUENCE: 130
gcuaagcacu uacaacuguu ugcagaggaa acugagacuu uguaacuaug ucucagucuc    60
aucugcaaag aaguaagugc uuugc    85

<210> SEQ ID NO 131
<211> LENGTH: 115
<212> TYPE: RNA
<213> ORGANISM: Artificial
<220> FEATURE:
<223> OTHER INFORMATION: synthetic nucleotide

<400> SEQUENCE: 131
ucuguuuauc accagauccu agaacccuau caauauuguc ucugcugugu aaauaguucu    60
gaguagugca auauugcuua uaggguuuug guguuuggaa agaacaaugg gcagg    115

<210> SEQ ID NO 132
<211> LENGTH: 87
<212> TYPE: RNA
<213> ORGANISM: Artificial
<220> FEATURE:
<223> OTHER INFORMATION: synthetic nucleotide

<400> SEQUENCE: 132
ucucaggcag ugacccucua gauggaagca cugucuguug uauaaaagaa aagaucgugc    60
aucccuuuag aguguuacug uuugaga    87

<210> SEQ ID NO 133
<211> LENGTH: 95
<212> TYPE: RNA
<213> ORGANISM: Artificial
<220> FEATURE:
<223> OTHER INFORMATION: synthetic nucleotide

<400> SEQUENCE: 133
gaagaucuca ggcagugacc cucuagaugg aagcacuguc uguugcuaa gaaaagaucg    60 ugcauccuuu uagaguguua cuguuugaga aaauc    95

<210> SEQ ID NO 134
<211> LENGTH: 68
<212> TYPE: RNA
<213> ORGANISM: Artificial
<220> FEATURE:
<223> OTHER INFORMATION: synthetic nucleotide

<400> SEQUENCE: 134
cuucaauuuu auuuuaaaac ggugagauuu uguuugucu gagaaaaucu cgcuguuuua    60
gacugagg    68

```
<210> SEQ ID NO 135
<211> LENGTH: 97
<212> TYPE: RNA
<213> ORGANISM: Artificial
<220> FEATURE:
<223> OTHER INFORMATION: synthetic nucleotide

<400> SEQUENCE: 135
cuagauaagu uauuaggugg gugcaaaggu aauugcaguu uuucccauua uuuuaauugc    60
gaaaacagca auuaccuuug caccaaccug auggagu                            97

<210> SEQ ID NO 136
<211> LENGTH: 98
<212> TYPE: RNA
<213> ORGANISM: Artificial
<220> FEATURE:
<223> OTHER INFORMATION: synthetic nucleotide

<400> SEQUENCE: 136
uacaauccaa cgaggauucu aauuucucca cgucuuuggu aauaagguuu ggcaaagaug    60
uggaaaaauu ggaauccuca uucgauuggu auaaccca                           98

<210> SEQ ID NO 137
<211> LENGTH: 98
<212> TYPE: RNA
<213> ORGANISM: Artificial
<220> FEATURE:
<223> OTHER INFORMATION: synthetic nucleotide

<400> SEQUENCE: 137
cauauuaggu uaaugcaaaa guaaucgcgg uuugugccag augacgauuu gaauuaauaa    60
auucauuugg uauaaaccgc gauuauuuuu gcaucaac                           98

<210> SEQ ID NO 138
<211> LENGTH: 97
<212> TYPE: RNA
<213> ORGANISM: Artificial
<220> FEATURE:
<223> OTHER INFORMATION: synthetic nucleotide

<400> SEQUENCE: 138
auaaaauuuc caauuggaac cuaaugauuc aucagacuca gauauuuaag uuaacaguau    60
uugagaauga ugaaucauua gguuccgguc agaaauu                            97

<210> SEQ ID NO 139
<211> LENGTH: 95
<212> TYPE: RNA
<213> ORGANISM: Artificial
<220> FEATURE:
<223> OTHER INFORMATION: synthetic nucleotide

<400> SEQUENCE: 139
ggugagugcg uuuccaagug ugaagggacc cuuccuguag ugucuuauau acaauacagu    60
aggaauguuc cuucuuugcc acucauacac cuuua                              95

<210> SEQ ID NO 140
<211> LENGTH: 98
<212> TYPE: RNA
<213> ORGANISM: Artificial
<220> FEATURE:
<223> OTHER INFORMATION: synthetic nucleotide

<400> SEQUENCE: 140
```

| | |
|---|---|
| cucuuguuca cagccaaacu cuacuugucc uucugagugu aauuacguac augcaguagc | 60 |
| ucaggagaca agcagguuua cccuguggau gagucuga | 98 |

<210> SEQ ID NO 141
<211> LENGTH: 2145
<212> TYPE: DNA
<213> ORGANISM: Homo sapiens

<400> SEQUENCE: 141

| | |
|---|---|
| cctctggcgg cccgccgtcc cagacgcggg aagagcttgg ccggtttcga gtcgctggcc | 60 |
| tgcagcttcc ctgtggtttc ccgaggcttc cttgcttccc gctctgcgag gagcctttca | 120 |
| tccgaaggcg ggacgatgcc ggataatcgg cagccgagga accggcagcc gaggatccgc | 180 |
| tccgggaacg agcctcgttc cgcgcccgcc atggaaccgg atggtcgcgg tgcctgggcc | 240 |
| cacagtcgcg ccgcgctcga ccgcctggag aagctgctgc gctgctcgcg ttgtaattgt | 300 |
| gtaagtgact gcattggaac tggatgtcca gtgtgttaca ccccggcctg gatacaagac | 360 |
| ttgaagataa atagacaact ggacagcatg attcaacttt gtagtaagct tcgaaatttg | 420 |
| ctacatgaca atgagctgtc agatttgaaa gaagataaac ctaggaaaag tttgttttaat | 480 |
| gatgcaggaa acaagaagaa ttcaattaaa atgtggttta gccctcgaag taagaaagtc | 540 |
| agatatgttg tgagtaaagc ttcagtgcaa acccagcctg caataaaaaa agatgcaagt | 600 |
| gctcagcaag actcatatga atttgtttcc ccaagtcctc ctgcagatgt ttctgagagg | 660 |
| gctaaaaagg cttctgcaag atctggaaaa agcaaaaaa agaaaacttt agctgaaatc | 720 |
| aaccaaaaat ggaatttaga ggcagaaaaa gaagatggtg aatttgactc caaagaggaa | 780 |
| tctaagcaaa agctggtatc cttctgtagc caaccatctg ttatctccag tcctcagata | 840 |
| aatggtgaaa tagacttact agcaagtggc tccttgacag aatctgaatg ttttggaagt | 900 |
| ttaactgaag tctctttacc attggctgag caaatagagt ctccagacac taagagcagg | 960 |
| aatgaagtag tgactcctat taagggcgac ataccttctg ttgaatacct tttacaaaat | 1020 |
| ggaagtgatc caaatgttaa agaccatgct ggatggacac cattgcatga agcttgcaat | 1080 |
| catgggcacc tgaaggtagt ggaattattg ctccagcata aggcattggt gaacaccacc | 1140 |
| gggtatcaaa atgactcacc acttcacgat gcagccaaga tgggcatgt ggatatagtc | 1200 |
| aagctgttac tttcctatgg agcctccaga atgctgtta atatatttgg tctgcggcct | 1260 |
| gtcgattata cagatgatga agtatgaaa tcgctattgc tgctaccaga aagaatgaa | 1320 |
| tcatcctcag ctagccactg ctcagtaatg aacactgggc agcgtaggga tggacctctt | 1380 |
| gtacttatag gcagtgggct gtcttcagaa caacagaaaa tgctcagtga gcttgcagta | 1440 |
| attcttaagg ctaaaaaata tactgagttt gacagtacag taactcatgt tgttgttcct | 1500 |
| ggtgatgcag ttcaaagtac cttgaagtgt atgcttggga ttctcaatgg atgctggatt | 1560 |
| ctaaaatttg aatgggtaaa agcatgtcta cgaagaaaag tatgtgaaca ggaagaaaag | 1620 |
| tatgaaattc ctgaaggtcc acgcagaagc aggctcaaca gagaacagct gttgccaaag | 1680 |
| ctgtttgatg gatgctactt ctatttgtgg ggaaccttca acaccatcc aaaggacaac | 1740 |
| cttattaagc tcgtcactgc aggtgggggc cagatcctca gtagaaagcc caagccagac | 1800 |
| agtgacgtga ctcagaccat caatacagtc gcataccatg cgagacccga ttctgatcag | 1860 |
| cgcttctgca cacagtatat catctatgaa gatttgtgta attatcaccc agagagggtt | 1920 |
| cggcagggca agtctggaa ggctccttcg agctggttta tagactgtgt gatgtccttt | 1980 |
| gagttgcttc ctcttgacag ctgaatatta taccagatga acatttcaaa ttgaatttgc | 2040 |

| | | |
|---|---|---|
| acggtttgtg agagcccagt cattgtactg ttttttaatgt tcacattttt acaaataggt | 2100 | |
| agagtcattc atatttgtct ttgaatcaaa aaaaaaaaaa aaaaa | 2145 | |

<210> SEQ ID NO 142
<211> LENGTH: 2243
<212> TYPE: DNA
<213> ORGANISM: Homo sapiens

<400> SEQUENCE: 142

| | |
|---|---|
| cagcttccct gtggtttccc gaggcttcct tgcttcccgc tctgcgagga gcctttcatc | 60 |
| cgaaggcggg acgatgccgg ataatcggca gccgaggaac cggcagccga ggatccgctc | 120 |
| cgggaacgag cctcgttccg cgcccgccat ggaaccggat ggtcgcggtg cctgggccca | 180 |
| cagtcgcgcc gcgctcgacc gcctggagaa gctgctgcgc tgctcgcgtt gatttgaaag | 240 |
| aagataaacc taggaaaagt ttgtttaatg atgcaggaaa caagaagaat tcaattaaaa | 300 |
| tgtggtttag ccctcgaagt aagaaagtca gatatgttgt gagtaaagct tcagtgcaaa | 360 |
| cccagcctgc aataaaaaaa gatgcaagtg ctcagcaaga ctcatatgaa tttgtttccc | 420 |
| caagtcctcc tgcagatgtt tctgagaggg ctaaaaaggc ttctgcaaga tctgaaaaaa | 480 |
| agcaaaaaaa gaaaacttta gctgaaatca accaaaaatg gaatttagag cagaaaaag | 540 |
| aagatggtga atttgactcc aaagaggaat ctaagcaaaa gctggtatcc ttctgtagcc | 600 |
| aaccatctgt tatctccagt cctcagataa atggtgaaat agacttacta gcaagtggct | 660 |
| ccttgacaga atctgaatgt tttggaagtt taactgaagt ctctttacca ttggctgagc | 720 |
| aaatagagtc tccagacact aagagcagga atgaagtagt gactcctgag aaggtctgca | 780 |
| aaaattatct tacatctaag aaatctttgc cattagaaaa taatgaaaaa cgtggccatc | 840 |
| acaatagact ttccagtccc atttctaaga gatgtagaac cagcattctg agcaccagtg | 900 |
| gagattttgt taagcaaacc gtgccctcag aaaatatacc attgcctgaa tgttcttcac | 960 |
| caccttcatg caaacgtaaa gttggtggta catcagggag gaaaaacagt aacatgtccg | 1020 |
| atgaattcat tagtctttca ccaggtacac caccttctac attaagtagt tcaagttaca | 1080 |
| ggcaagtgat gtctagtccc tcagcaatga agctgttgcc caatatggct gtgaaaagaa | 1140 |
| atcatagagg agagacttg ctccatattg cttctattaa gcatgaagct tgcaatcatg | 1200 |
| ggcacctgaa ggtagtggaa ttattgctcc agcataaggc attggtgaac accaccgggt | 1260 |
| atcaaaatga ctcaccactt cacgatgcag ccaagaatgg gcacgtggat atagtcaagc | 1320 |
| tgttactttc ctatggagcc tccagaaatg ctgttaatat atttggtctg cggcctgtcg | 1380 |
| attatacaga tgatgaaagt atgaaatcgc tattgctgct accagagaag aatgaatcat | 1440 |
| cctcagctag ccactgctca gtaatgaaca ctgggcagcg tagggatgga cctcttgtac | 1500 |
| ttataggcag tgggctgtct tcagaacaac agaaaatgct cagtgagctt gcagtaattc | 1560 |
| ttaaggctaa aaaatatact gagtttgaca gtacagtaac tcatgttgtt gttcctggtg | 1620 |
| atgcagttca aagtaccttg aagtgtatgc ttgggattct caatggatgc tggattctaa | 1680 |
| aatttgaatg ggtaaaagca tgtctacgaa gaaaagtatg tgaacaggaa gaaaagtatg | 1740 |
| aaattcctga aggtccacgc agaagcaggc tcaacagaga cagctgttg ccaaagctgt | 1800 |
| ttgatggatg ctacttctat ttgtggggaa ccttcaaaca ccatccaaag gacaacctta | 1860 |
| ttaagctcgt cactgcaggt gggggccaga tcctcagtag aaagcccaag ccagacagtg | 1920 |
| acgtgactca gaccatcaat acagtcgcat accatgcgag acccgattct gatcagcgct | 1980 |

```
tctgcacaca gtatatcatc tatgaagatt tgtgtaatta tcacccagag agggttcggc    2040
agggcaaagt ctggaaggct ccttcgagct ggtttataga ctgtgtgatg tcctttgagt    2100
tgcttcctct tgacagctga atattatacc agatgaacat ttcaaattga atttgcacgg    2160
tttgtgagag cccagtcatt gtactgtttt taatgttcac atttttacaa ataggtagag    2220
tcattcatat ttgtctttga atc                                            2243

<210> SEQ ID NO 143
<211> LENGTH: 27
<212> TYPE: PRT
<213> ORGANISM: Homo sapiens

<400> SEQUENCE: 143

Asp Thr Lys Ser Arg Asn Glu Val Val Thr Pro Ile Lys Gly Asp Ile
1               5                   10                  15

Pro Ser Val Glu Tyr Leu Leu Gln Asn Gly Ser
            20                  25

<210> SEQ ID NO 144
<211> LENGTH: 16
<212> TYPE: PRT
<213> ORGANISM: Homo sapiens

<400> SEQUENCE: 144

Asn Glu Val Val Thr Pro Ile Lys Gly Asp Ile Pro Ser Val Glu Tyr
1               5                   10                  15
```